(12) United States Patent
Chancellor et al.

(10) Patent No.: US 8,805,510 B2
(45) Date of Patent: Aug. 12, 2014

(54) METHODS AND SYSTEMS FOR ACHIEVING A PHYSIOLOGICAL RESPONSE BY PUDENDAL NERVE STIMULATION AND BLOCKADE

(75) Inventors: Michael B. Chancellor, Pittsburgh, PA (US); Changfeng Tai, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1706 days.

(21) Appl. No.: 12/184,518

(22) Filed: Aug. 1, 2008

(65) Prior Publication Data

US 2009/0036945 A1 Feb. 5, 2009

Related U.S. Application Data

(60) Provisional application No. 60/953,502, filed on Aug. 2, 2007, provisional application No. 60/955,212, filed on Aug. 10, 2007.

(51) Int. Cl.
*A61N 1/39* (2006.01)

(52) U.S. Cl.
USPC .......................................................... 607/41

(58) Field of Classification Search
USPC .......................................................... 607/41
See application file for complete search history.

(56) References Cited

U.S. PATENT DOCUMENTS

| | | | |
|---|---|---|---|
| 4,152,545 A | 5/1979 | Gilbreath, Jr. et al. | |
| 6,701,185 B2 | 3/2004 | Burnett et al. | |
| 6,907,293 B2 | 6/2005 | Grill et al. | |
| 6,928,320 B2 * | 8/2005 | King | 607/5 |
| 7,047,078 B2 | 5/2006 | Boggs, II et al. | |
| 7,054,689 B1 | 5/2006 | Whitehurst et al. | |
| 7,328,069 B2 * | 2/2008 | Gerber | 607/39 |
| 8,435,166 B2 | 5/2013 | Burnett et al. | |
| 2003/0004554 A1 * | 1/2003 | Riff et al. | 607/62 |
| 2003/0144710 A1 | 7/2003 | Haugland et al. | |
| 2005/0143783 A1 | 6/2005 | Boveja et al. | |
| 2006/0149333 A1 | 7/2006 | Tanagho et al. | |
| 2006/0184208 A1 | 8/2006 | Boggs et al. | |
| 2006/0195153 A1 | 8/2006 | DiUbaldi et al. | |
| 2006/0212096 A1 | 9/2006 | Stevenson | |

OTHER PUBLICATIONS

Agnew WF, McCreery DB. Neural Prostheses: Fundamental Studies. Englewood Cliffs, NJ: Prentice-Hall; 1990.

Barrington FJF. The component reflexes of micturition in the cat, Parts I and II. Brain 54:177-188, 1931.

Barrington FJF. The component reflexes of micturition in the cat III. Brain 64: 239-243, 1941.

Bhadra N, Kilgore KL. High-frequency electrical conduction block of mammalian peripheral motor nerve. Muscle Nerve. Dec. 2005;32(6):782-90.

(Continued)

*Primary Examiner* — Mark W Bockelman
(74) *Attorney, Agent, or Firm* — The Webb Law Firm

(57) ABSTRACT

Methods and apparatus are therefore provided herein for stimulating a desired physiological effect. The methods and apparatus can be used to control micturition, defecation and/or ejaculation. The methods and apparatus also can be used to control pain in the lower pelvic region, for example and without limitation, interstitial cystitis. The methods and apparatus also can be used to increase sexual sensation.

18 Claims, 37 Drawing Sheets

(56) References Cited

OTHER PUBLICATIONS

Bhadra N, Bhadra N, Kilgore K, Gustafson KJ. High frequency electrical conduction block of the pudendal nerve. J Neural Eng. Jun. 2006;3(2):180-7. Epub May 16, 2006.

Boggs JW, Wenzel BJ, Gustafson KJ, Grill WM. Bladder emptying by intermittent electrical stimulation of the pudendal nerve. J Neural Eng. Mar. 2006;3(1):43-51. Epub Jan. 20, 2006.

Boggs JW, Wenzel BJ, Gustafson KJ, Grill WM. Spinal micturition reflex mediated by afferents in the deep perineal nerve. J Neurophysiol. May 2005;93(5):2688-97. Epub Dec. 15, 2004.

Boggs JW, Wenzel BJ, Gustafson KJ, Grill WM. Frequency-dependent selection of reflexes by pudendal afferents in the cat. J Physiol. Nov. 15, 2006;577(Pt 1):115-26. Epub Aug. 31, 2006.

Bowman BR, McNeal DR. Response of single alpha motoneurons to high-frequency pulse trains. Firing behavior and conduction block phenomenon. Appl Neurophysiol. 1986;49(3):121-38.

Brindley GS. The first 500 patients with sacral anterior root stimulator implants: general description. Paraplegia. Dec. 1994;32(12):795-805.

Brindley GS, Rushton DN. Long-term follow-up of patients with sacral anterior root stimulator implants. Paraplegia. Oct. 1990;28(8):469-75.

Brindley GS. An implant to empty the bladder or close the urethra. J Neurol Neurosurg Psych 40: 358-369, 1977.

Cardenas DD, Kelly E, Mayo ME. Manual stimulation of reflex voiding after spinal cord injury. Arch Phys Med Rehabil. Jul. 1985;66(7):459-62.

Consortium for Spinal Cord Medicine. Bladder management for adults with spinal cord injury: a clinical practice guideline for healthcare providers. J Spinal Cord Med. 2006;29(5):527-73.

Creasey GH. Electrical stimulation of sacral roots for micturition after spinal cord injury. Urol Clin North Am. Aug. 1993;20(3):505-15.

de Groat WC, Araki I, Vizzard MA, Yoshiyama M, Yoshimura N, Sugaya K, Tai C, Roppolo JR. Developmental and injury induced plasticity in the micturition reflex pathway. Behav Brain Res. May 1998;92(2):127-40.

de Groat WC, Ryall RW. Reflexes to sacral parasympathetic neurones concerned with micturition in the cat. J Physiol. Jan. 1969;200(1):87-108.

de Groat WC. Nervous control of the urinary bladder of the cat. Brain Res. Apr. 11, 1975;87(2-3):201-11.

de Groat WC, Lalley PM. Reflex firing in the lumbar sympathetic outflow to activation of vesical afferent fibres. J Physiol. Oct. 1972;226(2):289-309.

de Groat WC, Ryall RW. Recurrent inhibition in sacral parasympathetic pathways to the bladder. J Physiol. Jun. 1968;196(3):579-91.

de Groat WC. Mechanisms underlying recurrent inhibition in the sacral parasympathetic outflow to the urinary bladder. J Physiol. May 1976;257(2):503-13.

Erlandson BE, Fall M, Carlsson CA. The effect of intravaginal electrical stimulation on the feline urethra and urinary bladder. Electrical parameters. Scand J Urol Nephrol Suppl. 1977;(44):5-18.

Fall M, Lindström S. Electrical stimulation. A physiologic approach to the treatment of urinary incontinence. Urol Clin North Am. May 1991;18(2):393-407.

Fall M, Erlandson B-E, Carlsson C-A, Lindström S. The effect of intravaginal electrical stimulation on the feline urethra and urinary bladder: neuronal mechanisms. Scand J Urol Nephrol Suppl. 1978;(44):19-30.

Garry RC, Roberts TD, Todd JK. Reflexes involving the external urethral sphincter in the cat. J Physiol. Dec. 1959;149:653-65.

Godec C, Cass AS, Ayala GF. Bladder inhibition with functional electrical stimulation. Urology. Dec. 1975;6(6):663-6.

Godec C, Cass AS, Ayala GF. Electrical stimulation for incontinence. Technique, selection, and results. Urology. Apr. 1976;7(4):388-97.

Gustafson KJ, Creasey GH, Grill WM. A Catheter Based Method to Activate Urethral Sensory Nerve Fibers. The Journal of Urology, vol. 170, Issue 1, pp. 126-129.

Gustafson KJ, Creasey GH, Grill WM. A urethral afferent mediated excitatory bladder reflex exists in humans. Neurosci Lett. Apr. 22, 2004;360(1-2):9-12.

Hansen J, Media S, Nøhr M, Biering-Sørensen F, Sinkjaer T, Rijkhoff NJ. Treatment of neurogenic detrusor overactivity in spinal cord injured patients by conditional electrical stimulation. J Urol. Jun. 2005;173(6):2035-9.

Ishigooka M, Hashimoto T, Sasagawa I, Izumiya K, Nakada T. Modulation of the urethral pressure by high-frequency block stimulus in dogs. Eur Urol. 1994;25(4):334-7.

Jiang CH, Lindstrom S. Prolonged enhancement of the micturition reflex in the cat by repetitive stimulation of bladder afferents. J Physiol. Jun. 1, 1999;517 ( Pt 2):599-605.

Kawatani M, Tanowitz M, de Groat WC. Morphological and electrophysiological analysis of the peripheral and central afferent pathways from the clitoris of the cat. Brain Res. May 16, 1994;646(1):26-36.

Kilgore KL, Bhadra N. Nerve conduction block utilising high-frequency alternating current. Med Biol Eng Comput. May 2004;42(3):394-406.

Kirkham AP, Knight SL, Craggs MD, Casey AT, Shah PJ. Neuromodulation through sacral nerve roots 2 to 4 with a Finetech-Brindley sacral posterior and anterior root stimulator. Spinal Cord. Jun. 2002;40(6):272-81.

Kirkham AP, Shah NC, Knight SL, Shah PJ, Craggs MD. The acute effects of continuous and conditional neuromodulation on the bladder in spinal cord injury. Spinal Cord. Aug. 2001;39(8):420-8.

Kock NG, Pompeius R. Inhibition of vesical motor activity induced by anal stimulation. Acta Chir Scand. Sep. 1963;126:244-50.

Kruse MN, de Groat WC. Consequences of spinal cord injury during the neonatal period on micturition reflexes in the rat. Exp Neurol. Jan. 1994;125(1):87-92.

Lindström S, Fall M, Carlsson CA, Erlandson BE. The neurophysiological basis of bladder inhibition in response to intravaginal electrical stimulation. J Urol. Feb. 1983;129(2):405-10.

Mazieres L, Jiang C, Lindstrom S. Bladder parasympathetic response to electrical stimulation of urethral afferents in the cat. Neurourol Urodyn 1997; 16:471-2.

Mazières L, Jiang C, Lindström S. The C fibre reflex of the cat urinary bladder. J Physiol. Dec. 1, 1998;513 ( Pt 2):531-41.

Nakamura M, Sakurai T, Tsujimoto Y, Tada Y. Bladder inhibition by electrical stimulation of the perianal skin. Urol Int. 1986;41(1):62-3.

Pikov V, Bullara L, McCreery DB. Intraspinal stimulation for bladder voiding in cats before and after chronic spinal cord injury. J Neural Eng. Dec. 2007;4(4):356-68. Epub Oct. 2, 2007.

Prévinaire JG, Soler JM, Perrigot M. Is there a place for pudendal nerve maximal electrical stimulation for the treatment of detrusor hyperreflexia in spinal cord injury patients? Spinal Cord. Feb. 1998;36(2):100-3.

Prévinaire JG, Soler JM, Perrigot M, Boileau G, Delahaye H, Schumacker P, Vanvelcenaher J, Vanhée JL. Short-term effect of pudendal nerve electrical stimulation on detrusor hyperreflexia in spinal cord injury patients: importance of current strength. Paraplegia. Feb. 1996;34(2):95-9.

Reboul J, Rosenbluth A. The action of alternating currents upon the electrical excitability of nerve. Am J Physiol 125: 205-215, 1939.

Reitz A, Schmid DM, Curt A, Knapp PA, Schurch B. Afferent fibers of the pudendal nerve modulate sympathetic neurons controlling the bladder neck. Neurourol Urodyn. 2003;22(6):597-601.

Rodriquez AA, Awad E. Detrusor muscle and sphincteric response to anorectal stimulation in spinal cord injury. Arch Phys Med Rehabil. Jun. 1979;60(6):269-72.

Rosenbluth A, Reboul J. The blocking and deblocking effects of alternating currents on nerve. Am J Physiol 125: 251-264, 1939.

Rossier A, Bors E. Detrusor responses to perianal and rectal stimulation in patients with spinal cord injuries. Urol Int. 1964;18:181-90.

Rubinstein JT, Tyler RS, Johnson A, Brown CJ. Electrical suppression of tinnitus with high-rate pulse trains. Otol Neurotol. May 2003;24(3):478-85.

Sawan M, Hassouna MM, Li JS, Duval F, Elhilali MM. Stimulator design and subsequent stimulation parameter optimization for controlling micturition and reducing urethral resistance. IEEE Trans Rehabil Eng. Mar. 1996;4(1):39-46.

(56) References Cited

OTHER PUBLICATIONS

Schmidt RA. Neural prostheses and bladder control. IEEE Eng Med Biol Mag 1983; 2:31-4.
Schmidt RA. Technique of pudendal nerve localization for block or stimulation. J Urol. Dec. 1989;142(6):1528-31.
Seif Ch, Braun PM, Bross S, Scheepe J, Weiss J, Schumacher S, Zendler S, Alken P, Jünemann KP. Selective block of urethral sphincter contraction using a modified Brindley electrode in sacral anterior root stimulation of the dog. Neurourol Urodyn. 2002;21(5):502-10.
Shefchyk SJ, Buss RR. Urethral pudendal afferent-evoked bladder and sphincter reflexes in decerebrate and acute spinal cats. Neurosci Lett. Mar. 20, 1998;244(3):137-40.
Spinelli M, Malaguti S, Giardiello G, Lazzeri M, Tarantola J, Van Den Hombergh U. A new minimally invasive procedure for pudendal nerve stimulation to treat neurogenic bladder: description of the method and preliminary data. Neurourol Urodyn. 2005;24(4):305-9.
Sundin T, Carlsson CA, Kock NG. Detrusor inhibition induced from mechanical stimulation of the anal region and from electrical stimulation of pudendal nerve afferents. An experimental study in cats. Invest Urol. Mar. 1974;11(5):374-8.
Tai C, Roppolo JR, de Groat WC. Block of external urethral sphincter contraction by high frequency electrical stimulation of pudendal nerve. J Urol. Nov. 2004;172(5 Pt 1):2069-72.
Tai C, Roppolo JR, de Groat WC. Response of external urethral sphincter to high frequency biphasic electrical stimulation of pudendal nerve. J Urol. Aug. 2005;174(2):782-6.
Tai C, Smerin SE, de Groat WC, Roppolo JR. Pudendal-to-bladder reflex in chronic spinal-cord-injured cats. Exp Neurol. Jan. 2006;197(1):225-34. Epub Nov. 2, 2005.
Tai C, Miscik CL, Ungerer TD, Roppolo JR, de Groat WC. Suppression of bladder reflex activity in chronic spinal cord injured cats by activation of serotonin 5-HT1A receptors. Exp Neurol. Jun. 2006;199(2):427-37. Epub Feb. 20, 2006.
Tai C, Shen B, Wang J, Chancellor MB, Roppolo JR, de Groat Wc. Inhibitory and excitatory perigenital-to-bladder spinal reflexes in the cat. Am J Physiol Renal Physiol 294: F591-602, 2008.
Tai C, Wang J, Chancellor MB, Roppolo JR, de Groat WC. Influence of temperature on pudendal nerve block induced by high frequency biphasic electrical current. J Urol. Sep. 2008;180(3):1173-8. Epub Jul. 18, 2008.
Tai C, Wang J, Wang X, de Groat WC, Roppolo JR. Bladder inhibition or voiding induced by pudendal nerve stimulation in chronic spinal cord injured cats. Neurourol Urodyn. 2007;26(4):570-7.

Tai C, Wang J, Wang X, Roppolo JR, de Groat WC. Voiding reflex in chronic spinal cord injured cats induced by stimulating and blocking pudendal nerves. Neurourol Urodyn. 2007;26(6):879-86.
Thor KB, Roppolo JR, deGroat WC. Naloxone induced micturition in unanesthetized paraplegic cats. J Urol. Jan. 1983;129(1):202-5.
Vaidyanathan S, Soni BM, Sett P, Singh G, Oo T, Hughes PL, Mansour P. Flawed trial of micturition in cervical spinal cord injury patients: guidelines for trial of voiding in men with tetraplegia. Spinal Cord. Dec. 2003;41(12):667-72.
Van Kerrebroeck PE, Koldewijn EL, Rosier PF, Wijkstra H, Debruyne FM. Results of the treatment of neurogenic bladder dysfunction in spinal cord injury by sacral posterior root rhizotomy and anterior sacral root stimulation. J Urol. Apr. 1996;155(4):1378-81.
Vodusek DB, Light JK, Libby JM. Detrusor inhibition induced by stimulation of pudendal nerve afferents. Neurourol Urodyn 1986; 5:381-9.
Walter JS, Wheeler JS, Cai W, Wurster RD. Direct bladder stimulation with suture electrodes promotes voiding in a spinal animal model: a technical report. J Rehabil Res Dev. Jan. 1997;34(1):72-81.
Walter JS, Wheeler JS, Robinson CJ, Wurster RD. Inhibiting the hyperreflexic bladder with electrical stimulation in a spinal animal model. Neurourol Urodyn. 1993;12(3):241-52; discussion 253.
Walter JS, Wheeler JS, Robinson CJ, Wurster RD. Surface stimulation techniques for bladder management in the spinal dog. J Urol. Jan. 1989;141(1):161-5.
Wang J, Shen B, Roppolo JR, de Groat WC, Tai C. Influence of frequency and temperature on the mechanisms of nerve conduction block induced by high-frequency biphasic electrical current. J Comput Neurosci. Apr. 2008;24 (2):195-206. Epub Aug. 8, 2007.
Wheeler JS Jr, Walter JS, Zaszczurynski PJ. Bladder inhibition by penile nerve stimulation in spinal cord injury patients. J Urol. Jan. 1992;147(1):100-3.
Williamson RP, Andrews BJ. Localized electrical nerve blocking. IEEE Trans Biomed Eng. Mar. 2005;52(3):362-70.
Yoshimura N, Smith CP, Chancellor MB, de Groat WC. Pharmacologic and potential biologic interventions to restore bladder function after spinal cord injury. Curr Opin Neurol. Dec. 2000;13(6):677-81.
Zhang X, Roppolo JR, de Groat WC, Tai C. Mechanism of nerve conduction block induced by high-frequency biphasic electrical currents. IEEE Trans Biomed Eng. Dec. 2006;53(12 Pt 1):2445-54.

* cited by examiner

A Experimental Setup

B Pudendal Nerve Stimulation and Block

A Spinal Intact

B Chronic SCI

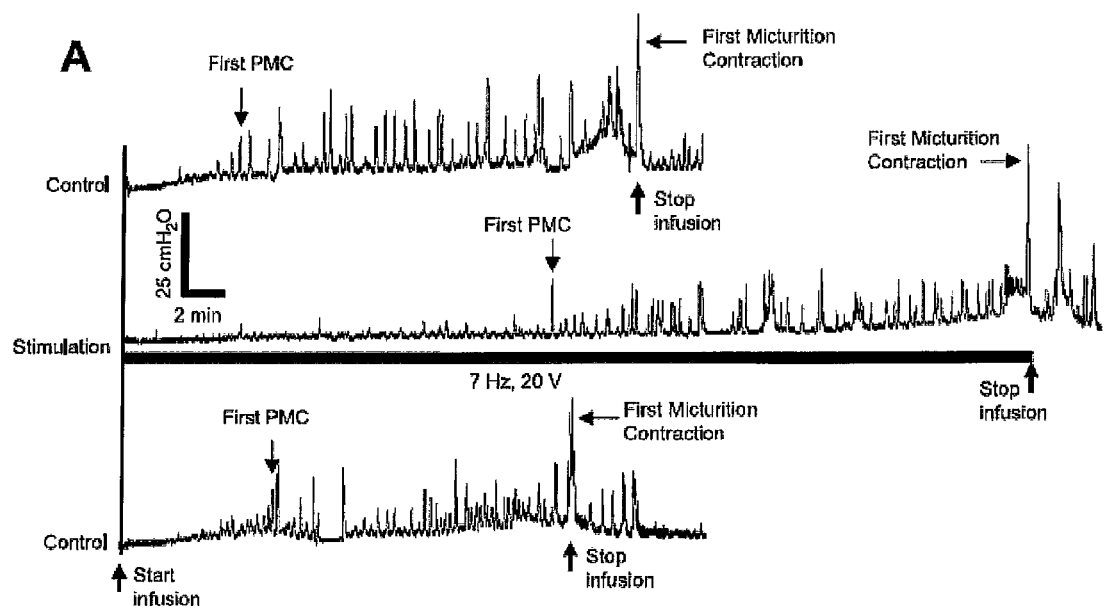
*Fig. 13A*
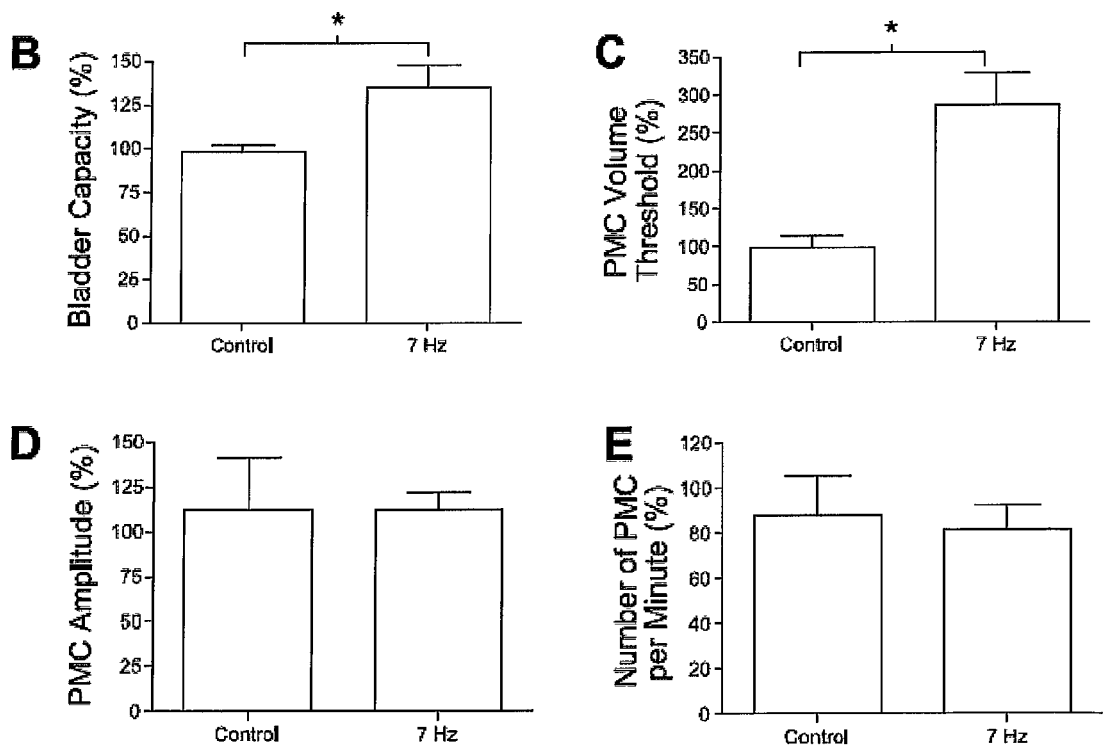
*Figs. 13B-E*

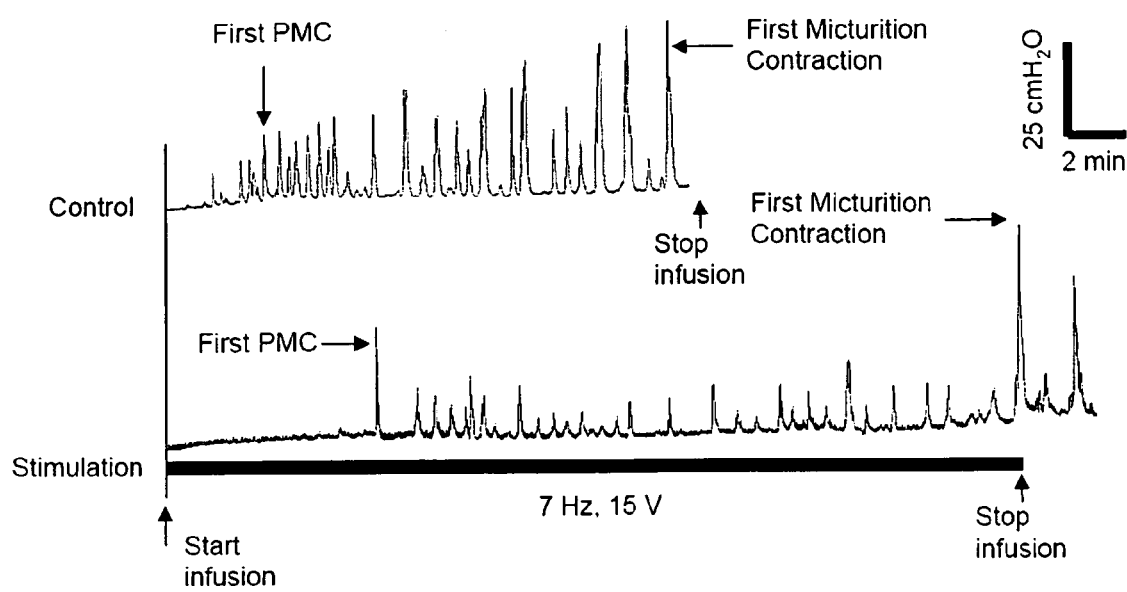
*Fig. 22A*
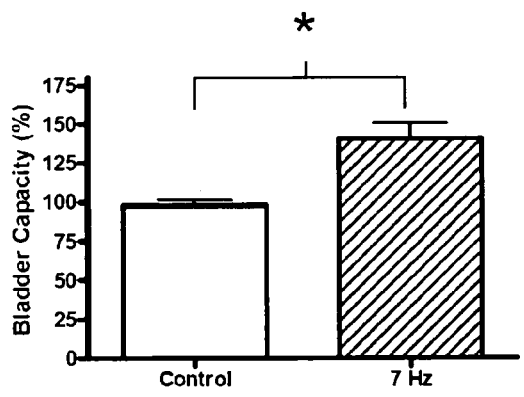 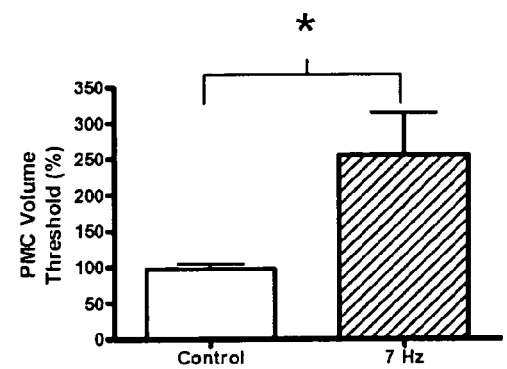
*Fig. 22B*  *Fig. 22C*

A Without Nerve Stimulation

B With 3 Hz Stimulation

METHODS AND SYSTEMS FOR ACHIEVING A PHYSIOLOGICAL RESPONSE BY PUDENDAL NERVE STIMULATION AND BLOCKADE

CROSS REFERENCE TO RELATED APPLICATIONS

This application claims the benefit under 35 U.S.C. §119(e) to U.S. Provisional Patent Application No. 60/953, 502, filed Aug. 2, 2007 and to U.S. Provisional Patent Application No. 60/955,212, filed Aug. 10, 2007, both of which are incorporated herein by reference in their entirety.

STATEMENT REGARDING FEDERAL FUNDING

The U.S. Government has a paid-up license in this invention and the right in limited circumstances to require the patent owner to license others on reasonable terms as provided for by the terms of Grant No. 1RO1-DK068566-01, awarded by the National Institutes of Health.

Described herein are methods for achieving a physiological response, such as micturition, defecation, ejaculation and pain relief by stimulating and/or blocking a pudendal nerve or a branch thereof.

A number of conditions arise from disruption of normal physiological processes in the lower pelvis. Conditions, such as urinary incontinence, overactive bladder, urine retention and voiding dysfunction, detrusor sphincter dyssinergia, fecal incontinence, constipation, irritable bowel syndrome, sexual dysfunction in both men and women, premature ejaculation, decreased sexual sensation, aorgasm, urethral pain, prostate pain, vulvodynia, anal pain, rectal pain and bladder pain are among those conditions. Those conditions can result from neurological impairment or from other diseases or conditions. For example, urinary incontinence can result from spinal cord injury or stroke, or damage caused by trauma, disease (e.g., multiple sclerosis) and/or congenital defects.

The pudendal nerve originates in the sacral plexus. It derives its fibers from the ventral branches of the second, third, and fourth sacral nerves (S2, S3, S4). It passes between the piriformis and coccygeus muscles and leaves the pelvis through the lower part of the greater sciatic foramen. It then crosses the spine of the ischium, and reenters the pelvis through the lesser sciatic foramen. It accompanies the internal pudendal vessels upward and forward along the lateral wall of the ischiorectal fossa, and is contained in a sheath of the obturator fascia termed the pudendal canal. The pudendal nerve gives off the inferior rectal nerves. It soon divides into two terminal branches: the perineal nerve, and the dorsal nerve of the penis (males) or the dorsal nerve of the clitoris (in females). The inferior anal nerves branch off shortly after passing through the greater sciatic foramen. The perineal nerve is the more superficial terminal branch of the pudendal nerve while the dorsal nerve of the penis or dorsal nerve of the clitoris are deeper terminal branches of the pudendal nerve, traveling into the deep perineal pouch (see, e.g., U.S. Pat. No. 7,047,078, FIGS. 1 and 2, and accompanying description for a useful diagram).

The pudendal nerve carries both sensory (afferent) and motor (efferent) signals. It innervates, among other things, the anal and external urethral sphincters. It also innervates the penis and clitoris, bulbospongiosus and ischiocavernosus muscles, and areas around the scrotum, perineum, and anus. At sexual climax, peristaltic action of muscles in the reproductive ducts and accessory glands (e.g., seminal vesicles, prostate and Cowper's (bulbourethral) glands, along with spasms in the bulbospongiosus and ischiocavernous muscles result in ejaculation in the male. Spasms in the bulbospongiosus and ischiocavernous muscles accompany most of the feelings of orgasm in both sexes.

Micturition, also called voiding or urination, is the act of emptying the bladder. In humans, when about 200 ml of urine has accumulated, distension of the bladder wall typically activates stretch receptors, triggering a visceral reflex arc. Afferent impulses are transmitted to the sacral region of the spinal cord, and efferent impulses return to the bladder via the parasympathetic pelvic nerves, causing the detrusor muscle of the bladder to contract and the internal sphincter of the bladder to relax. As the contractions increase in intensity, they force stored urine through the internal sphincter into the upper part of the urethra. Afferent impulses are also transmitted to the brain, so one feels the urge to void at this point. Because the external urethral (urinary) sphincter is voluntarily controlled, a person can choose to keep it closed and postpone bladder emptying temporarily. On the other hand, if the time is convenient, the voluntary sphincter can be relaxed, allowing urine to be expelled from the bladder. When one chooses not to void, reflex bladder contractions subside within a minute or so and urine continues to accumulate. After 200-300 ml more has collected, the micturition reflex occurs again and, if urination is delayed again, is damped once more.

Thus, normal bladder activity is typically divided into two phases. In the first phase, the "storage phase," the bladder detrusor is quiet and the EUS is closed. In the second phase, the "voiding phase," the bladder detrusor contracts and the EUS is (voluntarily) relaxed, permitting urine to flow out of the urethra. In patients with neurological damage affecting the micturition process, this process is disrupted, leading to, for example, incontinence or retention.

Incontinence is the inability to control micturition. Incontinence typically is a result of emotional problems, physical pressure during pregnancy, or nervous system problems, such as stroke or spinal cord lesions.

In urinary retention, the bladder is unable to expel its contained urine. Urinary retention is common after general anesthesia has been given (it seems that it takes a little time for the smooth muscles to regain their activity). Urinary retention in men often reflects prostate hypertrophy, narrowing the urethra, making it difficult to void. Stretching of the bladder wall by urine causes sensory impulses to be transmitted to the sacral region of the spinal cord. Motor impulses are delivered to the bladder detrusor muscle and the internal sphincter via parasympathetic fibers of the pelvic nerves. The pudendal nerve serves the striated muscle fibers of the external urethral sphincter.

Defecation proceeds by a similar manner as micturition. Sensory and motor control of defecation travels through the pudendal nerve. The rectum usually is empty. When feces are forced into the rectum by mass movement, the rectal wall is stretched, initiating the defecation reflex. In the defecation reflex, the walls of the sigmoid colon and rectum contracts and the anal sphincters relax, forcing the feces into the anal canal. The brain, however, decides whether the passage of feces should be temporarily stopped. If they are stopped, the rectal walls relax, until another mass-movement initiates another defecation reflex.

Patients with supra-sacral spinal cord injuries typically have no voluntary control over the micturition, defecation and ejaculatory processes. For example, after spinal cord injury (SCI) incontinence occurs frequently due to detrusor overactivity. Meanwhile, the bladder also does not empty well due to detrusor sphincter dyssynergia (DSD) resulting in a large residual volume of urine. Thus, the management of bladder function after SCI is a challenging task, because it requires inhibition of detrusor overactivity during urine storage and induction of a large amplitude bladder contraction to empty the bladder (Boggs J W, Wenzel B J, Gustafson K J, Grill W M. Spinal micturition reflex mediated by afferents in the deep perineal nerve. J Neurophysiol 93: 2688-2697, 2005). Current treatment for bladder dysfunction after SCI has either limited success (Yoshimura N, Smith C P, Chancellor M B, de Groat W C. Pharmacologic and potential biologic interventions to restore bladder function after spinal cord injury. Cur Opin Neurol 13: 677-681, 2000) or requires major invasive spinal surgery to implant stimulating electrodes on spinal roots (Brindley G S. The first 500 sacral anterior root stimulator implants: general description. Paraplegia 32: 795-805, 1994). Intermittent urethral catheterization is the most common method for managing urinary tract dysfunction. However, it can lead to frequent bladder infections.

U.S. Pat. No. 7,047,078 B2 and related United States Patent Publication No. 2006/0184208 A1, describes methods and apparatus for stimulating components in, on, or near the pudendal nerve or its branches in order to elicit a physiological response. Those documents describe the use of electrodes to directly stimulate or depress bladder contractions. By this method the depression of detrusor activity during the storage phase, and detrusor contraction can be achieved during a "voiding phase." Nevertheless, this method has been found to be unsatisfactory in achieving complete voiding, because it can not completely relax the EUS.

In another method, implemented by, e.g., a FineTech-Brindley (VOCARE) stimulator, micrutition and/or defecation is accomplished by pulsatile stimulation of the sacral spinal anterior roots. Brindley's method requires a major spinal surgery to open the spinal bone and cut the sacral spinal posterior roots, which eliminates the spinal reflexes for defecation and sexual functions. The electrical pulses typically generated by this device causes contraction of both the bladder detrusor and the EUS. Because the bladder detrusor comprises smooth muscle, while the EUS comprises striated muscle, the EUS releases before the detrusor. During the short time period between EUS release and detrusor release, voiding can occur. The pulses are repeatedly applied until the bladder is emptied.

The Medtronics InterStim® device may be used to treat detrusor hyperreflexia (DH, also called detrusor overactivity) or overactive bladder. It does not induce bladder excitation or urination (voiding). The InterStim® device sends electrical pulses to the sacral nerve to influence the bladder and surrounding muscles that manage urinary function.

In Seif, Ch., et al. (Selective Block of Urethral Sphincter Contraction Using a Modified Brindley Electrode in Sacral Anterior Root Stimulation of the Dog, Neurourology and Urodynamics 21:502-510 (2002)), an electrode of a FineTech-Brindley type device was used to stimulate, by low frequency (e.g., 20 Hz) an anterior S2 root in order to prevent transmission of motor impulses to the EUS in dogs. Other than a rhizotomy of all posterior roots from S1 to S3, the dogs were healthy, including having intact spinal cords. Although occasionally effective to permit voiding, it does not address, or prevent the concomitant EUS contraction and detrusor contraction present in for example, DSD, or stimulated by the activation of the detrusor by the device.

This selective stimulation method activates the small nerve in the sacral spinal root without activating the large nerve. The "block" described in In Seif, Ch., et al. was not a blockage of, e.g., the conduction of the pudendal nerve, rather it did not activate them in fact. As a result, the detrusor-sphincter-dyssynergia (DSD) occurring after spinal cord injury will still cause EUS contraction when the bladder contracts. Because, In Seif, Ch., et al. used dogs with an intact spinal cord, there was no DSD in this animal model. It is believed that the methods described in In Seif, Ch., et al., would not provide any better results in DSD patients using the FineTech-Brindley device.

Further, in Seif, Ch., et al., the method requires opening up of the vertebrae and cutting the spinal sensory roots. This further damages the nerve systems and results in loss of reflex defecation, reflex penile erection, reflex ejaculation, etc. There have been studies showing that the method described in Seif, Ch., et al., do not work well if the sensory spinal roots are not cut (Kirkham, A. P. S., Knight, S. L., Craggs, M. D., Casey, A. T. M. and Shah, P. J. R., Neuromodulation through sacral nerve roots 2 to 4 with a Finetech-Brindley sacral posterior and anterior root stimulator. Spinal Cord, 40:272-281, 2002. and Van Kerrebroeck, P. E. V., Koldewijn, E. L., Rosier, P. F. W. M., Wijkstra, H. and Debruyne, F. M. J., Results of the treatment of neurogenic bladder dysfunction in spinal cord injury by sacral posterior root rhizotomy and anterior sacral root stimulation. J. Urol., 155:1378-1381, 1996).

Thus, there is a need for methods and apparatus that can effectively control the micturition, defecation, pelvic pain and/or sexual response

SUMMARY

Methods and apparatus are therefore provided herein for stimulating a desired physiological effect. The methods and apparatus can be used to control micturition, defecation and/or ejaculation. The methods and apparatus also can be used to control pain in the lower pelvic region, for example and without limitation, interstitial cystitis. The methods and apparatus also can be used to increase sexual sensation.

In one non-limiting embodiment, the pudendal nerve, or a branch thereof, is stimulated by electric pulses in a frequency range of from 0.5 to 15 Hz to inhibit bladder or rectal contractions and to reduce pelvic pain of bladder, urethra, prostate, anus, or rectum, such as from interstitial cystitis. In another non-limiting embodiment, the pudendal nerve, or a branch thereof, is stimulated by electric pulses in a frequency range of from 15 to 50 Hz to elicit bladder contractions, rectal contractions, ejaculation, orgasm and/or sexual arousal. The electrical pulses in a frequency range of from 15 to 50 Hz may be applied intermittently, such as for two or more stimulation intervals of 0.5 to 60 seconds, with a suitable time period between the intervals, such as from 0.5 seconds to 5 minutes, to facilitate and/or optimize micturition, defecation, ejaculation, orgasm or sexual stimulation.

In the case of micturition and defecation, the pudendal nerve, distal to the point of stimulation by electrical pulses in a frequency range of from 15 to 50 Hz, may be co-stimulated with electrical pulses in a frequency range of greater than 4 kHz, for example and without limitation, from 4 kHz to 50 kHz, to block activity of the EUS and/or anal sphincter, thereby facilitating micturition and defecation.

The electrical pulses may be applied by an implanted device, with implanted electrodes stimulating a pudendal nerve or a branch thereof, or to the skin (transdermally, intradermally or subdermally) to a superficial branch of the pudendal nerve, typically located perianally or perigenitally. Systems and devices are described herein for implementing the described methods. In non-limiting embodiments, the systems comprise a pulse generator and a controller for generating and controlling parameters of the electrical pulses. The pulse generator may be implanted in a subject or used externally in the case of applying electric pulses to the skin. Additional non-limiting embodiments and details and variations to these embodiments are provided herein and in the claims.

BRIEF DESCRIPTION OF THE DRAWINGS

FIG. 13. Inhibitory effect of electrical perigenital stimulation on bladder activity during cystometrograms (CMGs). A: bladder pressure traces. The initial empty bladder was infused with saline at 2 ml/min. Control: no stimulation. Stimulation: 7 Hz; 20 V; 0.2-ms pulse width. The black bar under pressure trace marks the stimulation duration. B: bladder capacity was significantly increased by electrical perigenital stimulation at 7 Hz. C: volume threshold to induce the first premicturition contraction (PMC) was also significantly increased. D and E: PMC amplitude and number of PMCs per minute were not changed. Responses in B-E were normalized to the measurements during first control CMG. Stimulation in B-E: 5-30 V; 0.2-ms pulse width. The calibration bars in A apply to all bladder pressure recordings. *Statistical significance (P<0.05); n=4.

FIG. 22. Inhibitory effect of electrical perianal stimulation on bladder activity during cystometrogram (CMG). A. Bladder pressure traces. The initial empty bladder was infused with saline at 4 ml/min. Control: no stimulation. Stimulation: 7 Hz; 15 V; 0.2 ms pulse width. The black bar under bladder pressure trace marks the stimulation duration. B. Bladder capacity was significantly increased by electrical perianal stimulation at 7 Hz. C. The volume threshold to induce the first pre-micturition contraction (PMC) was also significantly increased. D-E. PMC amplitude and number of PMCs per minute were decreased significantly. Responses in B-E were normalized to the measurements during first control CMG. Stimulation in B-E: 8-30 V; 0.2 ms pulse width. *indicates statistical significance (P<0.05). N=9 (3 tests on each cat).

DETAILED DESCRIPTION

Figure 1:
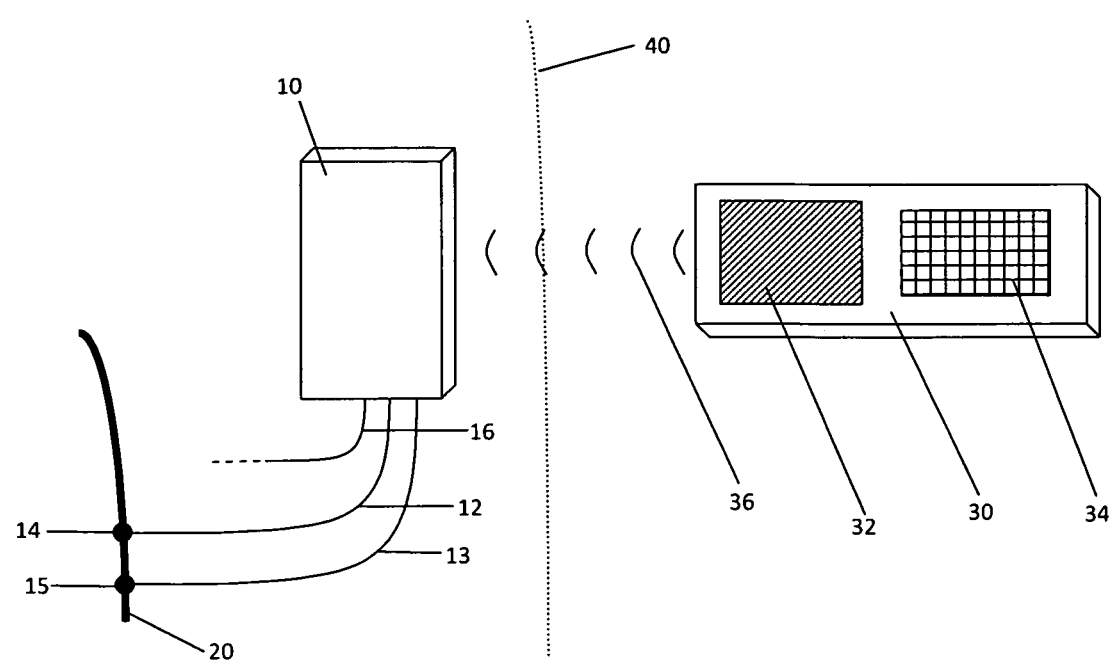
FIG. 1 is a schematic diagram of one non-limiting embodiment of a device useful in implementing methods described herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

The ranges provided herein for e.g., electric pulse frequencies are based on experimentation on cats. Nevertheless, the frequencies necessary to elicit a desired response in humans is very similar. For example, as shown in U.S. Pat. No. 7,047,078, stimulation of the pudendal nerve in human subjects at 10 Hz did not cause contractions of the bladder, while stimulation at 20 Hz did. As such, frequency ranges applicable to cats are considered to be effective in humans. It should also be recognized that the optimal frequency to elicit a desired effect may vary from subject-to-subject, depending on a number of factors. Optimal frequencies to elicit the desired goals will likely need to be adjusted from person-to-person. A "subject" may be human or animal.

According to one non-limiting embodiment of the invention method of controlling one or both of micturition and defecation in a subject is provided. In one aspect the method is directed to a method of inducing micturition and/or defecation in a subject. The method comprises inducing one or both of micturition and defecation in the subject by applying an electrical signal ipsilaterally or bilaterally to a pudendal nerve or a branch thereof of a subject. Either one or both (left and right) of the pudendal nerves, needs to be stimulated in this manner to produce a contraction reflex. A typical subject has a spinal cord injury in which voluntary control of EUS or anal sphincter, and/or other neurological components of the micturition and/or defecation processes are diminished or absent, such as in persons with severed or damaged spinal cords or multiple sclerosis. The electrical signal comprises electrical pulses able to create a reflex (e.g., as described above) that results in one or both of bladder contractions and rectal contractions. Although this will cause bladder or rectal contractions, without sufficient voluntary control of the EUS and/or anal sphincter, those muscles may reflexively contract against the pressure of the contractions, inhibiting or preventing micturition and/or defecation. By applying a blocking electrical signal to the pudendal nerve of the subject or a branch thereof distal (away from the brain/spinal cord) to the point on the nerve stimulated to produce the contraction reflexes, and preferably to both (left and right) pudendal nerves to completely block reflexive contraction of the EUS and/or anal sphincter. The blocking electrical signal is able to inhibit contraction of one or both of the external urethral sphincter and the anal sphincter of the subject. As will be recognized by a person of skill in the art, characteristics of electrical pulse, including, without limitation, amplitude (pulse strength, referring to the magnitude or size of a signal voltage or current), voltage, amperage, duration, frequency, polarity, phase, relative timing and symmetry of positive and negative pulses in biphasic stimulation, and/or wave shape (e.g., square, sine, triangle, sawtooth, or variations or combinations thereof) may be varied in order to optimize results in any particular subject or class of subjects. Subjects may be classified by species, disease/condition, sex, or any other factor that can be generalized to a group.

The method may further comprise, prior to (and/or after) producing one or both of micturition and defecation in the subject, applying an electrical signal to a pudendal nerve or a branch thereof of the subject, the electrical signal having an amplitude and frequency able to create a reflex that inhibits one or both of bladder contractions and rectal contractions in the subject. This produces a storage stage, similar to the typical storage stage of the normal micturition or defecation processes.

The primary characteristic of the electrical signals used to produce a desired response, as described above, is pulse frequency. Although effective ranges (e.g., frequencies able to produce a stated effect) may vary from subject-to-subject, and the controlling factor is achieving a desired outcome, certain, non-limiting exemplary ranges may be as follows. For stimulating bladder, rectal or sexual gland/muscle contractions, those frequencies may range from approximately 15 Hz (Hertz, or pulses per second) to approximately 50 Hz. For blocking nerve function, such as in blocking reflexive contraction of the EUS or anal sphincter, those frequencies range from approximately 4 kHz (kiloHertz, e.g., 4,000 Hz) or greater, for example and without limitation, from approximately 4 kHz to approximately 10 kHz. For inhibiting contraction of the bladder or rectum, those frequencies may range from approximately 0.5 Hz to approximately 15 Hz. Variations from these ranges may be capable of achieving the same results. Stated ranges are intended to include all values and ranges within the stated ranges. So long as other characteristics of the electrical signals (e.g., without limitation, amplitude, voltage, amperage, duration, polarity, phase, relative timing and symmetry of positive and negative pulses in biphasic stimulation, and/or wave shape) are within useful ranges, modulation of the pulse frequency will achieve a desired result. Useful values for those other characteristics are well-known in art and/or can be readily established by routine experimentation, for instance by the ability to prevent or induce voiding, for instance, by methods described herein.

Wedensky inhibition, anodal block, depolarizing prepulses and slowly rising pulses are non-limiting examples of art-recognized methods useful in blocking nerves. So long as other pulse parameters are within acceptable limits, the blockage is temporary and does not damage the blocked nerve. In one non-limiting embodiment, nerve blockage is achieved by applying middle-range currents of at least 4 kHz, for example and without limitation, in the range of from 4 kHz to 10 kHz to the nerve using a suitable electrode. The maximum useful frequency is a frequency that is able to achieve the desired result (e.g., nerve blockage) with acceptable safety. The voltage and amperage of the current typically should be below 15 mA and 50V to prevent nerve damage, though typically lower values are applied, for example in the range of 1 to 30V.

In another embodiment, a system for controlling one or both of micturition and defecation in a subject is provided. The system comprises an implantable pulse generator unit having a first output channel adapted to produce electric pulses in a first stage at a frequency ranging from 0.5 Hz to 15 Hz, and in a second stage at a frequency ranging from 15 Hz to 50 Hz, and a second output channel adapted to produce electric pulses at a frequency of greater than approximately 4 kHz, for example and without limitation, between 4 kHz and 10 kHz during the second stage, for nerve blockage, for example prevention of reflexive contractions of the EUS and/or anal sphincter when applied to the pudendal nerve. The pulse generation unit may comprise a first wireless communication system for receiving control instructions from a wireless controller; and a wireless controller, comprising an input, a display and a second wireless communication system configured to send control instructions to the implantable pulse generator. In one embodiment, the electric pulses are biphasic. The first wireless communication system may also transmit status information for the pulse generator to the wireless controller. The pulse generator unit may also further comprise a third output channel adapted to produce electric pulses at a frequency of at least 4 kHz, for example and without limitation in a range between 4 kHz and 10 kHz, at the same time as the second output channel. Further description of one embodiment of such a system is described in reference to FIG. 1. The phrases "configured to" and "adapted to" and like terms or phrases refer to the manufacture, production, modification, etc. of a device or system to produce a desired function. In the context of the devices or systems described herein, a device or system "adapted to" or "configured to" produce a desired output is a device programmed of otherwise manufactured, produced, modified, etc. in any manner to produce the stated effect.

In another embodiment, voiding, defecation, ejaculation, orgasm, inhibition of bladder or rectal contractions, reduction of pelvic pain and/or sexual stimulation may be accomplished by stimulating a superficial (close to the skin) branch of a pudendal nerve. As described above, many of these results can be accomplished by stimulating the pudendal nerve or a branch thereof by implanted electrodes. However, previously it was not known if this could be accomplished by superficial stimulation of branches of the pudendal nerve. By superficial stimulation, it is meant by applying electrical stimulus to the skin, intradermally or subdermally. The benefit of this is that surgical implantation of electrodes, and the requisite surgical skill and expense is not necessary. Block of the pudendal nerves is not possible by this method, but effective voiding may be achieved, for instance, as depicted below, by stimulating the nerves in a pulsatile fashion. The electrical pulses will stimulate both smooth muscle contractions in the bladder, rectum and glands and muscles associated with ejaculation, orgasm or sexual stimulation, as well as the EUS and anal sphincter. Because the striated muscle of the EUS and anal sphincters will relax upon cessation of electrical stimulation before the smooth muscle of the bladder, rectum and sexual glands and ducts, voiding of the bladder, rectum and sexual glands and ducts is achieved for a short time period following cessation of the electrical pulse (post-stimulus voiding).

In this embodiment of the method, electrodes are placed perigenitally or perianally in order to be in sufficient proximity to the pudendal nerves. Electrodes may be placed on the skin, intradermally or subdermally, by any useful method, prior to stimulus. In one embodiment, trans-epidermal nerve stimulation (TENS) may be applied, and therefore, and electrode, re-usable, disposable, or semi-disposable, that is useful in TENS applications may be suitable for applying stimulus to superficial branches of the pudendal nerve as described herein. Pulse amplitude, voltage, amperage, duration, waveform, phase, etc. may be varied to achieve optimal activity. For example, pulses ranging from approximately 15 Hz to 50 Hz may be applied for 0.1 to 60 seconds, or ranges therebetween, including 1, 2, 5, 10, 15, 20, 25, 30, 45 or 50 seconds. Bladder or rectal voiding will occur immediately following cessation of the stimulus. When voiding ceases, in for example, 1 to 20 seconds, pulses may again applied until post-stimulus voiding ceases. It may be desirable to minimize pulse lengths. For inhibitory and pain relief effects, for example and without limitation, pulses ranging from 0.5 Hz to 15 Hz may be applied.

Damage to nerves by the application of an electrical current may be minimized, as is known in the art, by application of biphasic pulses or biphasic waveforms to the nerve(s), as opposed to a monophasic pulses or waveforms that can damage nerves in some instances of long-term use. "Biphasic current," "biphasic pulses" or "biphasic waveforms" refer to two or more pulses that are of opposite polarity that typically are of equal or substantially equal net charge (hence, biphasic and charge balanced). This is accomplished, for example, by applying through an electrode one or more positive pulses, followed by one or more negative pulses, typically of the same amplitude and duration as the positive pulses, or vice versa, such that the net charge applied to the target of the electrode is zero or approximately zero. The opposite polarity pulses may have different amplitudes, profiles or durations, so long as the net applied charge by the biphasic pulse pair (the combination of the positive and negative pulses) is approximately zero.

The electrodes used to stimulate the nerves may be of any useful composition or mixture of compositions, such as platinum or stainless steel, as are known in the art, and may be of any useful configuration for stimulating nerves, including monopolar, bipolar, or tripolar electrode with or without a cuff wrapping around the pudendal nerve, as are known in the art.

Pulses applied to nerves via electrodes are generated by any device capable of delivering suitable electrical pulses. For uses, such as perianal or perigenital stimulation of pudendal nerve branches, the device can have one or more output channels. In the context of devices and methods used herein, an output channel is an electrical circuit that is able to send an electrical signal to an electrode. If a device has two or more output channels, the output of each channel is typically independently controllable with regard to one or more parameters, such as pulse frequency, amplitude, voltage, amperage, duration, polarity, phase, relative timing and symmetry of positive and negative pulses in biphasic stimulation, and/or wave shape. In the context of the embodiments for blocking the pudendal nerves or branches thereof, while stimulating contractions of the bladder or rectum, a device having two or three independent output channels is needed. A first channel is used to provide an electrical signal suitable for inducing bladder and/or rectum contractions during a voiding stage, such as, without limitation, biphasic pulses of between 15 Hz and 50 Hz, and an electrical signal suitable for inhibiting bladder and/or rectum contractions during a storage stage, such as, without limitation, biphasic pulses of between 0.5 Hz and 15 Hz. A second, or a second and third output channel may be used to provide an electrical signal suitable for blocking activity of the EUS and/or anal sphincter during the voiding stage, such as, without limitation, biphasic pulses of at least 4 kHz, for example and without limitation, between 4 kHz and 10 kHz. The output of the second output channel may be split to send signals to both sides of the pudendal nerves or branches thereof, or the output of a second output channel and a third output channel may be independently sent to left and right pudendal nerves or branches thereof.

FIG. 1 depicts schematically one non-limiting embodiment of a three-channel system for stimulating pudendal nerves or branches thereof according to the methods described herein. Pulse generator 10 is depicted as having three output channels. Wire leads 12 and 13 are attached to electrodes 14 and 15, which are placed about pudendal nerve 20. Electrode 15 is shown distal to electrode 14. In the context of a method comprising blocking the EUS and/or anal sphincter and stimulating or inhibiting contractions in the bladder and/or rectum, electrode 14 would be used to stimulate or inhibit bladder and/or rectal contractions, while electrode 15 would be used to block the EUS or anal sphincter. As needed, wire lead 16 is attached to another electrode (not shown in FIG. 1) that is placed about the pudendal nerve on the other side of the body to block the pudendal nerve on the opposite side. Pulse generator 10 is shown as implanted beneath skin 40. Output parameters of the pulse generator 10 can be controlled via a wired interface, but preferably is controlled by wireless transmission, which can be carried any suitable wireless protocol, such as radio frequency, IEEE 802.11a/b/g, Bluetooth, etc. Thus, an external controller 30 is depicted for communicating with the pulse generator 10. External controller 30 is depicted as having a display 32, such as an LCD, LED or OLED display, and a keypad 34 for entering data into the external controller 30. External controller is depicted as sending a wireless transmission 36 to pulse generator 10, though in another embodiment, data can be transferred both to the pulse generator 10 from the external communicator 30 and vice-versa, to permit monitoring of one or more parameters of pulse generator 10, including, without limitation, output signal characteristics (e.g., frequency, amplitude, etc. as outlined above) and battery strength. Activity of pulse generator 10 and external controller 30 typically is microprocessor controlled and software/firmware installed onto the pulse generator 10 and external controller 30 hardware may be used to implement the described tasks, and to provide, for example and without limitation, a GUI (graphical user interface) for the display 32, which facilitates use of the system. Both pulse generator 10 and external controller 30 may comprise any suitable electrical and electronic components to implement the activities, including, microprocessors, memory (e.g., RAM, ROM. Flash memory, etc.), connectors, batteries, power transformers, amplifiers, etc. A person of skill in the electronic arts will be able to implement such a system using readily-available electronics parts and ordinary programming skills. Proprietary chips, chipsets, etc. may be designed and manufactures to implement the devices described herein.

External controller 30 may be a proprietary device that is specifically designed for the task, or a non-proprietary device, such as a smart phone or a portable computer. Pulse generator 10 may comprise any number of channels, so long as the number of channels needed to implement a desired method is provided. In one variation of the embodiment depicted in FIG. 1, wire lead 13 is split into two wire leads, each of which are terminated in a separate electrode, with one wire lead and electrode for stimulating a left pudendal nerve or branch thereof, and the other wire lead for stimulating a right pudendal nerve or branch thereof.

One potential difficulty with use of wireless devices is one of identity. A controller should only be able to control one pulse generator to prevent accidental stimulation of unintended subjects, or even intentional stimulation. In its simplest form, the transmission range of the devices can also be limited to prevent transmission over distances more than a few feet, thereby limiting the chances of unintended stimulation (crosstalk). Also, any number of identity verification mechanisms may be utilized to prevent crosstalk. In one embodiment, different transmission wavelengths may be used for different devices, thus lowering the likelihood of crosstalk. In another embodiment, the pulse generator is programmed to only respond to a transmission containing a pre-defined signal, such that the pulse generator and external wireless controller must first, and/or periodically "handshake" in order to communicate. Likewise, the pulse generator and/or controller may transmit encrypted signals which only can be decrypted by a key stored in the other of the pulse generator and/or controller. In another embodiment, RFID tagging technology may be used to ensure that the controller and pulse generator match. Any combination of these proximity and/or identity verification measures may be used to prevent cross-talk. Other useful technologies for ensuring security and identity in communication are, or may be available and are equally applicable.

Also provided herein is a method of stimulating a physiological response in a subject. The method comprises stimulating the pudendal nerve or a branch thereof in a subject using an implanted electrode with electrical pulses at a frequency and amplitude able to either inhibit or stimulate one or more of bladder contractions, rectum contractions, and bulbospongiosus and ischiocavernosus muscle contractions, thereby obtaining the physiological response. The physiological response may be one or more of micturition, defecation, ejaculation, orgasm, inhibition of bladder contractions, inhibition of pelvic pain of bladder, urethra, prostate, anus, or rectum, inhibition of rectal contractions, and sexual arousal.

In one embodiment, the electrical pulses range from 0.5 to 15 Hz, which is suitable for is inhibition of bladder contractions, and inhibition of pelvic pain of bladder, urethra, prostate, anus, or rectum, and inhibition of rectal contractions, including, without limitation pain from interstitial cystitis/painful bladder syndrome, which is treatable by electrical stimulation. In another embodiment, the electrical pulses range from 15 to 50 Hz, in which case the physiological response is, without limitation, micturition, defecation, ejaculation, and one or both of orgasm and increased sexual response. The 15-50 Hz pulses may be applied intermittently, for example and without limitation, in two or more stimulation intervals of from 0.5 to 60 seconds with a rest period of no electrical stimulation able to cause bladder or rectal contractions between stimulation intervals. Typically during the rest period, no inhibitory stimulus (e.g., stimulus in the range of 0.5 to 15 Hz) is applied. During the rest period no electrical signal, or essentially no electrical signal is applied.

Also provided is a system for controlling one or both of micturition and defecation in a subject. The system comprises a pulse generator unit having a first output channel adapted to produce electric pulses in a first stage at a frequency ranging from 0.5 Hz to 15 Hz, and in a second stage at a frequency ranging from 15 Hz to 50 Hz and a controller configured to send control instructions to the implantable pulse generator. The pulses may be biphasic and, typically, balanced. The system, especially when in use, comprises a lead wire and an electrode connected to the output channel, with the electrode placed either on a subject's skin to stimulate a superficial branch of a pudendal nerve, such as perianally or perigenitally, or implanted, in which case the electrode stimulates the pudendal nerve or a branch thereof. In any embodiment in which a pulse generator is implanted, the device is "implantable, which means that it is medically acceptable for implantation. A wireless controller, as in any embodiment described herein, may be used to control an implanted device. For external electrodes, the pulse generator and controller may be housed separately or within a single housing. Variations of device/system structure for any device or system described herein will be apparent to one of skill in the art and are a matter of design choice and optimization within the abilities of a person of ordinary skill in the art.

Example 1

Figure 2:
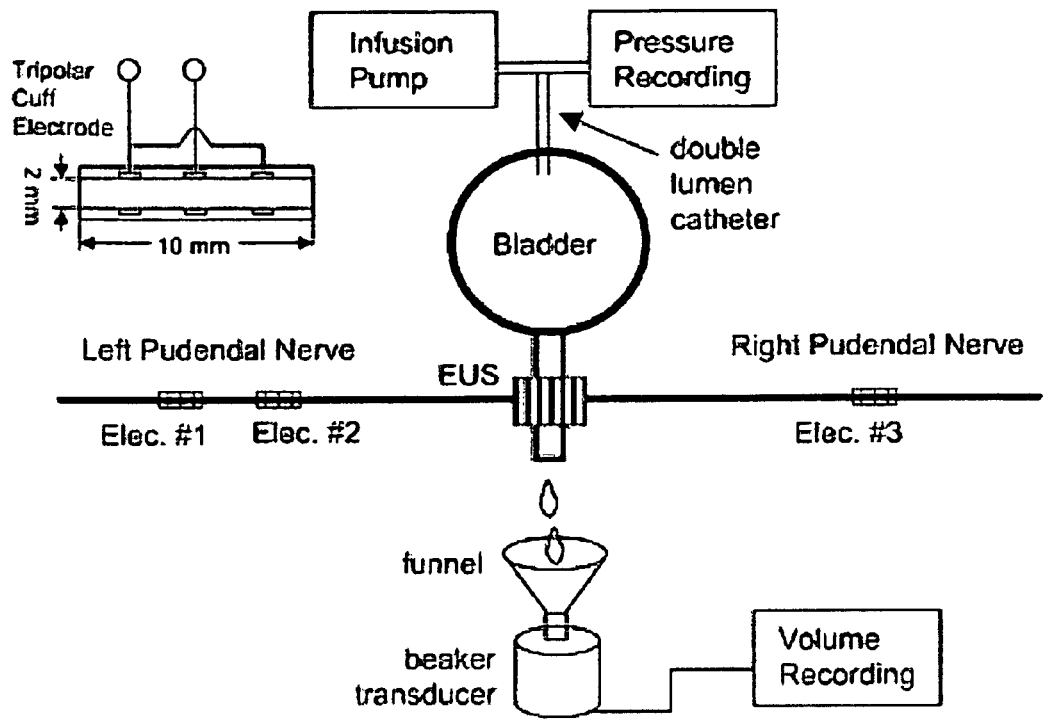
FIG. 2. (A) Experimental setup. (B) Pudendal nerve stimulation (20 Hz) and block (10 kHz) delivered to each electrode. The 20 Hz stimulation at electrode #1 activates an excitatory pudendal-to-bladder spinal reflex to induce bladder contraction, while the 10 kHz stimulations at electrodes #2 and #3 block pudendal nerve conduction bilaterally to prevent EUS contraction. EUS=external urethral sphincter.
Figure 2:
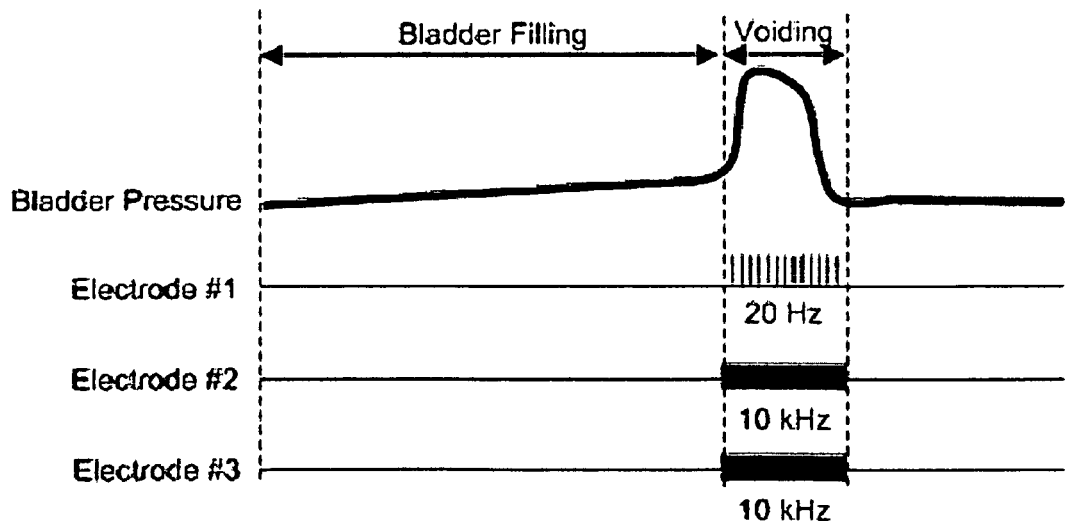

The following determined if an efficient voiding reflex can be induced in the chronic SCI cats by a continuous 20 Hz pudendal nerve stimulation. We used a nerve blocking technique to determine if detrusor sphincter dyssynergia interferes with pudendal nerve stimulation-induced voiding. Our previous studies (Tai C, Roppolo J R, de Groat W C. Block of external urethral sphincter contraction by high frequency electrical stimulation of pudendal nerve. J Urol 2004; 172: 2069-72 and Tai C, Roppolo J R, de Groat W C. Response of external urethral sphincter to high frequency biphasic electrical stimulation of pudendal nerve. J Urol 2005; 174:782-6) revealed that electrical stimulation of the pudendal nerve in cats at a frequency of 6-10 kHz blocks nerve conduction. In this study, combining excitatory and blocking stimulation of the pudendal nerves induced an efficient voiding reflex in chronic SCI cats.
Materials and Methods A total of six female cats were used in this study (three spinal intact and three chronic SCI animals, 3.5-4.5 kg). For the three chronic SCI cats that were also used in our previous study, 35 spinal cord transection was performed (3-11 months prior to the experiment) at the T9-T10 spinal cord level by a dorsal laminectomy under isoflurane anesthesia and aseptic conditions. During the experiments, animals (both spinal intact and SCI) were anesthetized with α-chloralose (60 mg/kg i.v., supplemented as needed) following induction with halothane (2-3% in $O_2$). Systemic blood pressure was monitored via a cannula placed in the right carotid artery. A tracheotomy was performed and a tube was inserted to secure the airway. A catheter for i.v. infusion was introduced into right ulnar vein. A double lumen catheter (five French) was inserted into the bladder via the dome and secured by a ligature (see FIG. 2A). One lumen of the catheter was attached to a pump to infuse the bladder with saline, and the other lumen was connected to a pressure transducer to monitor the bladder activity. A funnel was used to collect the voided fluid in a beaker that was attached to a force transducer to record the volume. For the three chronic SCI animals, the pudendal nerves were accessed posteriorly between the sciatic notch and the tail. Two tripolar cuff electrodes [Micro Probe, Inc., Gaithersburg, Md.; NC223(Pt)] were placed around the left pudendal nerve (Elec. #1 and #2 in FIG. 2A). A third tripolar cuff electrode was placed around the right pudendal nerve (Elec. #3 in FIG. 2A). The three electrode leads in each cuff electrode were made of platinum wires (diameter 0.25 mm) with a 2 mm distance between the leads. The two leads at each end of the cuff electrode were connected together (see FIG. 2A). After implanting the pudendal nerve electrodes, the muscle and skin were closed by sutures. For the three spinal intact animals, electrodes were not implanted on the pudendal nerve. The temperature of the animals was maintained at 35-37° C. during the experiments using a heating pad. A pulse oximeter (Nonin Medical, Inc., Plymouth, Minn.; 9847V) with its sensor clipped on the tongue of animals was used to monitor the arterial oxygen saturation and heart rate. Blood pressure, heart rate, and front paw withdraw reflex were used to evaluate the anesthetic depth.

In the experiments in chronic SCI cats, uniphasic pulses at 20 Hz frequency, 2-10 V intensity and 0.2 msec pulse width were used to stimulate the pudendal nerve at electrode #1 (see FIG. 2B) in order to induce the excitatory pudendal-to-bladder reflex and bladder contractions. Our previous study[34] in chronic SCI cats showed that 20 Hz pudendal nerve stimulation induces strong bladder contractions. The stimulation intensity was determined at the beginning of each experiment by a preliminary test of its effectiveness to induce bladder contractions. In order to block pudendal nerve conduction and prevent an EUS contraction, a train of high-frequency, biphasic, continuous (duty cycle 100%), charge-balanced, rectangular pulses at 10 kHz frequency and 10 mA intensity were delivered to electrode #2 and/or #3 (see FIG. 2B). The stimulation frequency and intensity were shown in our previous studies (Id.) to be effective in blocking the pudendal nerves of cats. A Grass S88 stimulator (Grass Medical Instruments) with stimulus isolator (Grass Medical Instruments, SIU5) was used to generate the uniphasic stimulus pulses for electrode #1. The high-frequency, biphasic stimulation waveforms (10 kHz) used at electrodes #2 and #3 were generated by a computer with a digital-to-analog circuit board (National Instruments, Austin, Tex.; AT-AO-10) that was programmed using LabView programming language (National Instruments). Linear stimulus isolators (World Precision Instruments, Sarasota, Fla.; A395) were used to deliver the high-frequency, biphasic constant current pulses to the nerves via electrodes #2 and #3.

Starting with the bladder empty, saline was slowly infused (0.5-4 ml/min) into the bladder to induce a voiding reflex (i.e., a cystometrogram-CMG). Bladder capacity was defined as the infused volume at which a bladder contraction was induced and fluid was released from the urethral orifice. When fluid was released, the infusion was stopped. The distension induced voiding was evaluated in both spinal intact and chronic SCI cats. In the chronic SCI cats during an intercontraction quiet period after stopping the bladder infusion, 20 Hz stimulation was applied to the pudendal nerve to induce bladder contractions. In another stimulation paradigm, prior to the start of 20 Hz stimulation at electrode #1, the kHz blocking stimulation was applied either to electrode #2 only or to electrodes #2 and #3 (see FIG. 2B) in order to block the EUS contraction during the 20 Hz pudendal nerve stimulation. Voiding efficiency, maximal bladder pressure, and average flow rate were measured in order to evaluate the effectiveness of the induced voiding reflex. Voiding efficiency is defined as the total voided volume divided by the total infused volume. Parameters measured from multiple trials in the same animal were averaged and then presented as mean±standard error (SE). Since ANOVA analysis showed no significant difference between trials in the same animals, two-way ANOVA (experimental conditions vs. animals) was used to determine any statistical significance (P<0.05). Since each parameter was measured multiple times in the same animal, for each experimental condition there were three data sets (mean, SD, and N) from the three animals. Two-way ANOVA was performed on the three data sets (animals) for different experimental conditions (control, nerve stimulation and block, etc.).

Results

Figure 3:
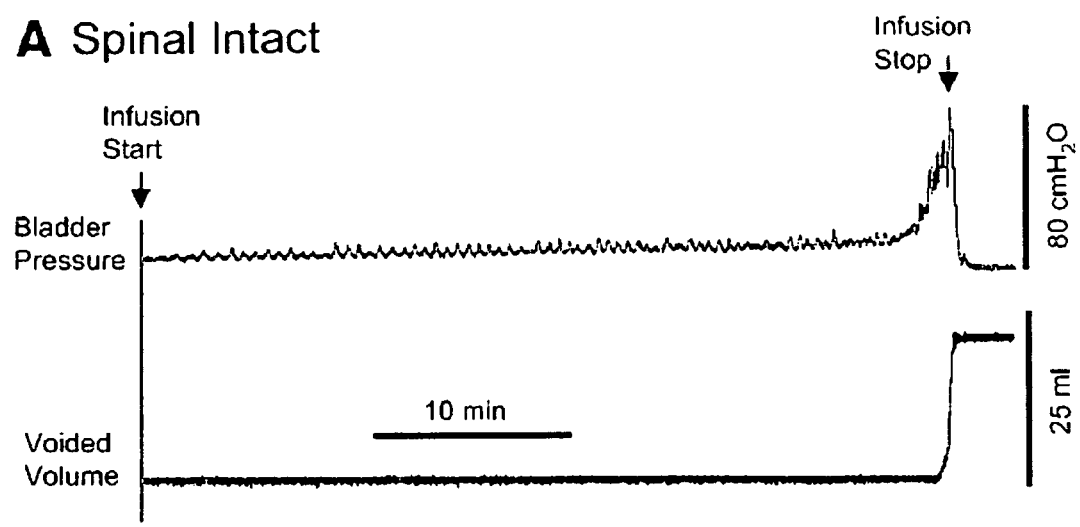
FIG. 3. Voiding reflex induced by bladder distension in a normal (A) and a chronic SCI (B) cat. (A) In a normal cat, the bladder was infused at 0.5 ml/min. At the infusion stop a total of 21 ml was infused, and 20 ml was voided with a voiding efficiency of 95.2%. (B) In a chronic SCI cat (11 months after SCI), the bladder was infused at 4 ml/min. At the infusion stop a total of 74 ml was infused, but only 4 ml was voided with a voiding efficiency of 5.4%.
Figure 3:
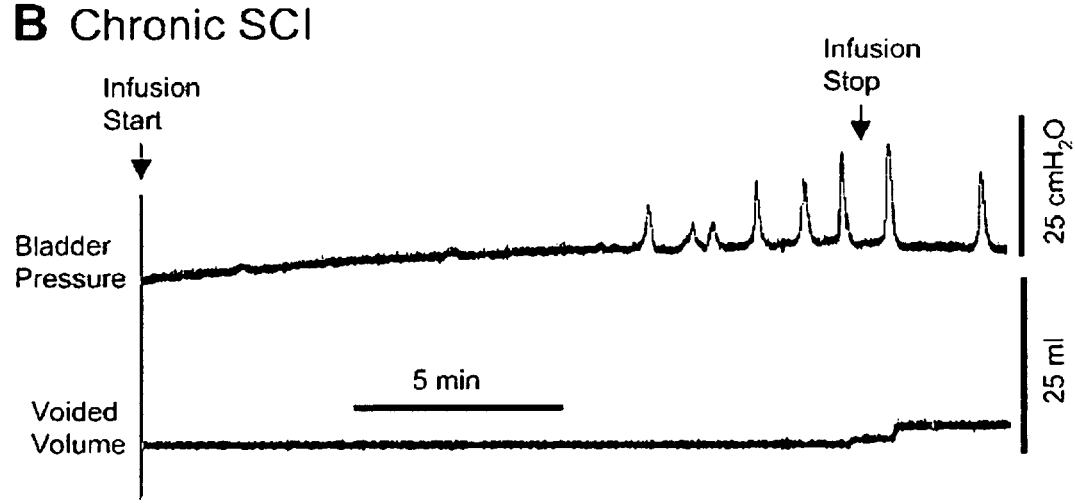

Voiding Reflex in Normal and Chronic SCI Cats As shown in FIG. 3, the CMGs in spinal intact and chronic SCI cats were markedly different. During bladder filling in chronic SCI cats the bladder exhibited multiple, low amplitude, short duration, non-voiding contractions (i.e., neurogenic detrusor overactivity, FIG. 3B); whereas the bladder of spinal cord intact animals was quiescent until the onset of voiding (FIG. 3A). Voiding was also different.

Compared to the bladder contractions induced by bladder distension in spinal cord intact cats the contractions induced by distension in chronic SCI cats were weaker and considerably less efficient in producing voiding (FIGS. 3A and 3B). On average the peak intravesical pressures during reflex contractions in chronic SCI cats were only 30% of those in spinal intact cats (FIG. 4A, 23.1±1.7 cmH2O vs. 72.5±11.8 cmH$_2$O, P<0.05). The average duration of contractions was only 20% of the duration in spinal intact animals (21.9±0.9 sec vs. 109.3±8.2 sec, P<0.05). Average voiding efficiency (7.3±0.9%, FIG. 5) and flow rate (0.23_0.07 ml/sec, FIG. 4B) were markedly (P<0.05) lower than the values in spinal intact cats (93.6±2.0% and 0.56±0.16 ml/sec respectively, see FIGS. 4B and 5). Note that in both types of animals the saline infusion was stopped when fluid was released from the urethral meatus.

To determine if voiding might improve as bladder volume increased with continued infusion in chronic SCI cats the CMGs were also continued beyond the time of the first void (FIG. 6A). This only produced a series of short duration, small bladder contractions of approximately the same amplitude and duration. Each contraction released only a small amount of fluid equivalent to the volume infused during each contraction interval. During the experiment shown in FIG. 6A the residual bladder volume remained static during the series of small voiding reflexes. At the end of 12 min infusion beyond the first void, the residual bladder volume was almost equal to the volume (19 vs. 20 ml) prior to the first void. Thus in chronic SCI cats continued infusion of fluid did not increase bladder volume; and voiding efficiency during each void was still poor.

A second approach to improve voiding efficiency was to increase bladder volume prior to voiding utilizing a low frequency pudendal nerve stimulation (3 Hz) which we showed in a previous study (Tai C, Smerin SE, de Groat W C, et al. Pudendal-to-bladder reflex in chronic spinal-cord-injured cats. Exp Neurol 2006a; 197:225-34) suppressed non-voiding contractions during bladder filling and increased bladder capacity in chronic SCI cats. It was anticipated that at a larger bladder volume a more prolonged and larger amplitude bladder contraction might occur. However as shown in FIG. 6B in the same chronic SCI cat used in FIG. 3B, 3 Hz pudendal nerve stimulation inhibited bladder activity during filling and increased bladder capacity from 74 to 124 ml, but after the stimulation was stopped only short duration bladder contractions occurred and voiding was still inefficient (31 ml voided leaving 93 ml residual volume in the bladder).

Figure 7:
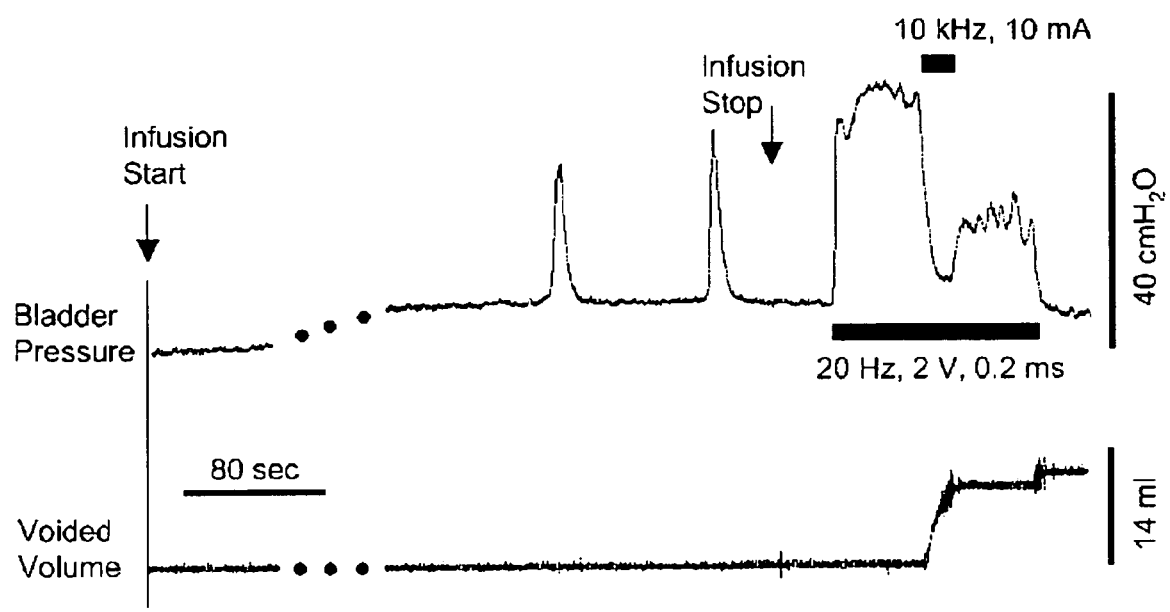
FIG. 7. Voiding reflex induced by 20 Hz pudendal nerve stimulation alone in a chronic SCI cat (9 months after SCI). The 10 kHz blocking stimulation was only briefly applied bilaterally to the pudendal nerves during the 20 Hz stimulation of the left pudendal nerve. Twenty-four milliliter was infused into the bladder when the infusion was stopped. Twelve milliliter was voided only during the blocking stimulation. The black bars on bladder pressure trace indicate the stimulation durations. Infusion rate: 2 ml/min.

Voiding Reflex in Chronic SCI Cats Induced by Pudendal Nerve Stimulation and Block As shown in FIG. 7, 20 Hz excitatory pudendal nerve stimulation applied to electrode #1 (see FIG. 2) elicited large amplitude (40 cmH$_2$O), long duration (80-100 sec) bladder contractions in chronic SCI cats that were equivalent to the voiding contractions in cats with an intact spinal cord. However, voiding did not occur during the 20 Hz stimulation. On the other hand, when 10 kHz blocking stimulation was applied for a brief period (20 sec) to the pudendal nerves bilaterally (electrodes #2 and #3, see FIG. 2) during the 20 Hz excitatory stimulation, the bladder pressure immediately decreased and voiding occurred (FIG. 7). When the blocking stimulation was stopped, voiding stopped and bladder pressure increased. The bladder pressure was maintained until the end of 20 Hz stimulation when an additional void occurred presumably due to the rapid relaxation of the urethral sphincter while the bladder pressure was still high. An efficient voiding reflex was also induced in chronic SCI cats by the 20 Hz pudendal nerve stimulation when the 10 kHz blocking stimulation was applied ipsilaterally (i.e., only applied to the electrode #2, see FIG. 2) or bilaterally (i.e., applied to both electrodes #2 and #3, see FIG. 2) prior to the excitatory pudendal nerve stimulation. FIG. 8A shows in a chronic SCI cat that a large amount (53 ml) of fluid was voided from a bladder containing 86 ml when the 20 Hz stimulation was combined with the ipsilateral 10 kHz blocking stimulation resulting in a voiding efficiency of 61.6%. The voiding occurred primarily during the first stimulation period when two periods of stimulation were used. FIG. 8B shows in another chronic SCI cat that the 20 Hz stimulation combined with bilateral 10 kHz blocking stimulation also induced an efficient (88%) voiding reflex. As shown in FIG. 8B, a small amplitude bladder contraction was induced at the onset of the 10 kHz blocking stimulation without voiding. When the 20 Hz stimulation was started, the bladder pressure increased quickly and then decreased once fluid started to flow through the open urethra. During the induced voiding the fluid flow was a steady stream and the bladder pressure was relatively low (less than 30 cmH$_2$O).

Figure 4A:
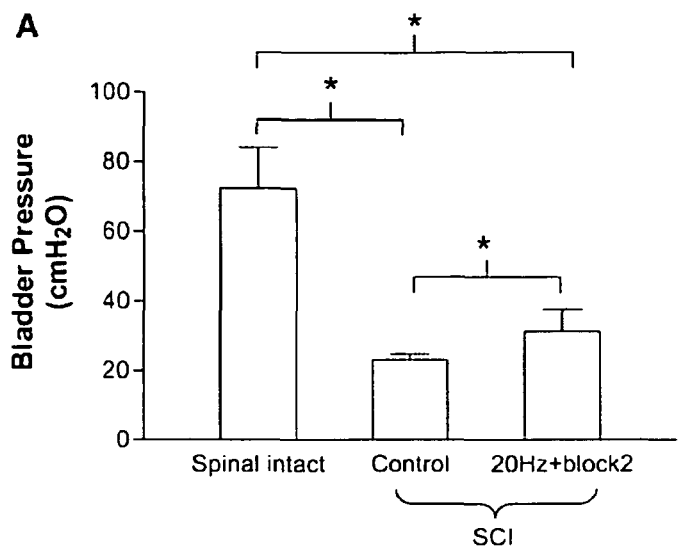
FIG. 4. Maximal bladder pressure (A) and average flow rate (B) during voiding in spinal intact and chronic SCI cats (N=3). Spinal intact—during voiding induced by bladder distension in spinal intact cats (see FIG. 3A). Control—during voiding induced by bladder distension in chronic SCI cats (see FIG. 3B). 20 Hz±block 2—during voiding induced by 20 Hz stimulation of the left pudendal nerve with 10 kHz blocking of both left and right pudendal nerves in chronic SCI cat (see FIG. 8B). *Indicates statistical significance (P<0.05).
Figure 4B:
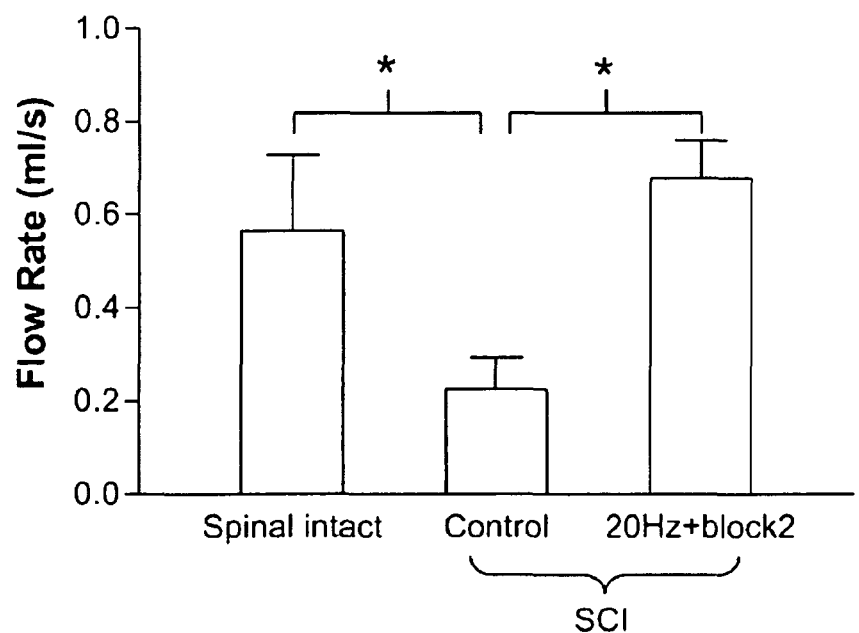
Figure 5:
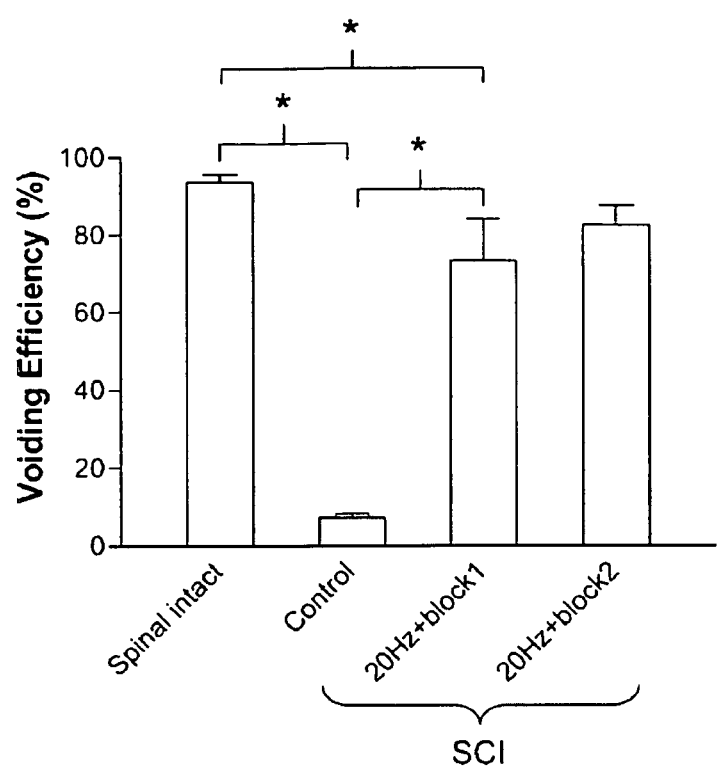
FIG. 5. Voiding efficiency in spinal intact and chronic SCI cats (N=3). Spinal intact—efficiency of voiding induced by bladder distension in spinal intact cats (see FIG. 3A). Control—efficiency of voiding induced by bladder distension in chronic SCI cats (see FIG. 3B). 20 Hz±block 1—efficiency of voiding induced by 20 Hz stimulation and 10 kHz blocking of the left pudendal nerve in chronic SCI cats (see FIG. 8A). 20 Hz±block 2—efficiency of voiding induced by 20 Hz stimulation of the left pudendal nerve with 10 kHz blocking of both left and right pudendal nerves in chronic SCI cat (see FIG. 8B). *Indicates statistical significance (P<0.05).

On average the 20 Hz pudendal nerve stimulation coupled with 10 kHz ipsilateral block significantly (P<0.05) increased the voiding efficiency in chronic SCI cats to 73.2±10.7% compared to the voiding efficiency induced by bladder distension (7.3±0.9%) as shown in FIG. 5. With 10 kHz bilateral block of the pudendal nerves, the 20 Hz pudendal nerve stimulation further increased voiding efficiency to 82.5±4.8%. This efficiency is not significantly different from the voiding efficiency in spinal intact cats induced by bladder distension, although the voiding efficiency induced by ipsilateral block is still significantly different (FIG. 5). As shown in FIG. 4A, the maximal bladder pressure (31.4±6.4 cmH$_2$O) during voiding induced by the 20 Hz pudendal nerve stimulation with 10 kHz bilateral nerve block was significantly (P<0.05) increased in chronic SCI cats compared to the bladder distension induced voiding (23.1±1.7 cmH$_2$O). But it was still significantly (P<0.05) lower than that in spinal intact cats (72.5±11.8 cmH$_2$O). Therefore, simultaneously stimulating and blocking the pudendal nerves induced low pressure voiding in chronic SCI cats. The average flow rate (0.68±0.08 ml/sec) was significantly (P<0.05) increased by the 20 Hz pudendal nerve stimulation with bilateral 10 kHz block in chronic SCI cats compared to the distension induced voiding (0.23±0.07 ml/sec) (see FIG. 4B). It was not significantly different (P>0.05) from the flow rate in spinal intact cats (0.56±0.16 ml/sec). Therefore, in chronic SCI cats 20 Hz pudendal nerve stimulation combined with 10 kHz nerve block induced a markedly different voiding reflex than bladder distension (see FIGS. 3B, 6, and 8) resulting in an efficient voiding (FIG. 5) with a fast flow rate (FIG. 4B) and a low bladder pressure (FIG. 4A).

Discussion

Figure 8:
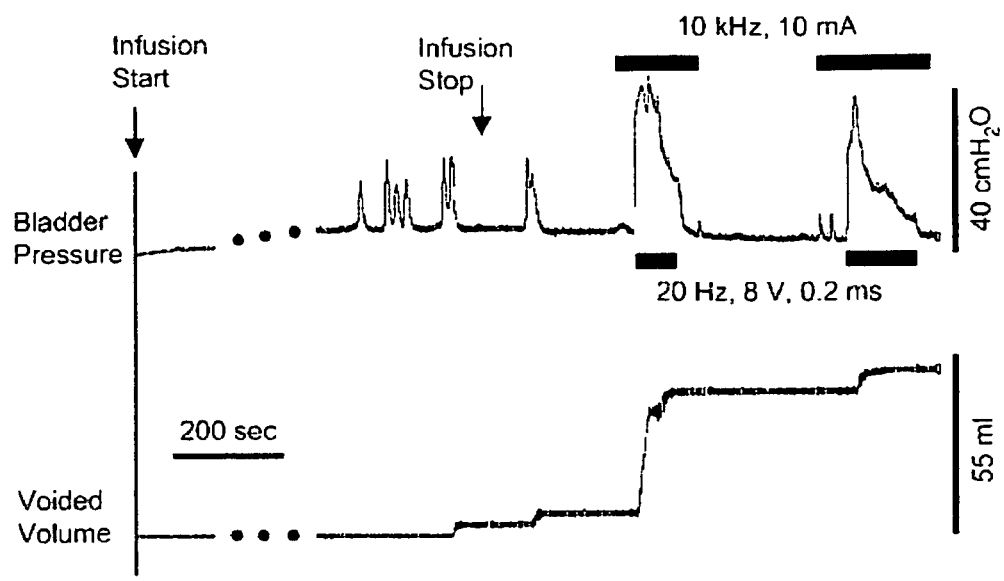
FIG. 8. Voiding reflex induced by stimulating and blocking the pudendal nerves in chronic SCI cats. (A) Both 20 Hz and 10 kHz stimulations were applied to the left pudendal nerve in a chronic SCI cat (11 month after SCI). Eighty-six milliliter was infused into the bladder when the infusion was stopped. A total of 53 ml was voided with a voiding efficiency of 61.6%. Infusion rate: 4 ml/min. (B) The 20 Hz stimulation was applied to the left pudendal nerve during 10 kHz bilateral blocking stimulation of the pudendal nerves in a chronic SCI cat (9 month after SCI). Twenty-five milliliter was infused into the bladder when the infusion was stopped. Twenty-two milliliter was voiding during the 20 Hz stimulation with a voiding efficiency of 88%. Infusion rate: 2 ml/min. The black bars on bladder pressure traces indicate the stimulation durations.
Figure 8:
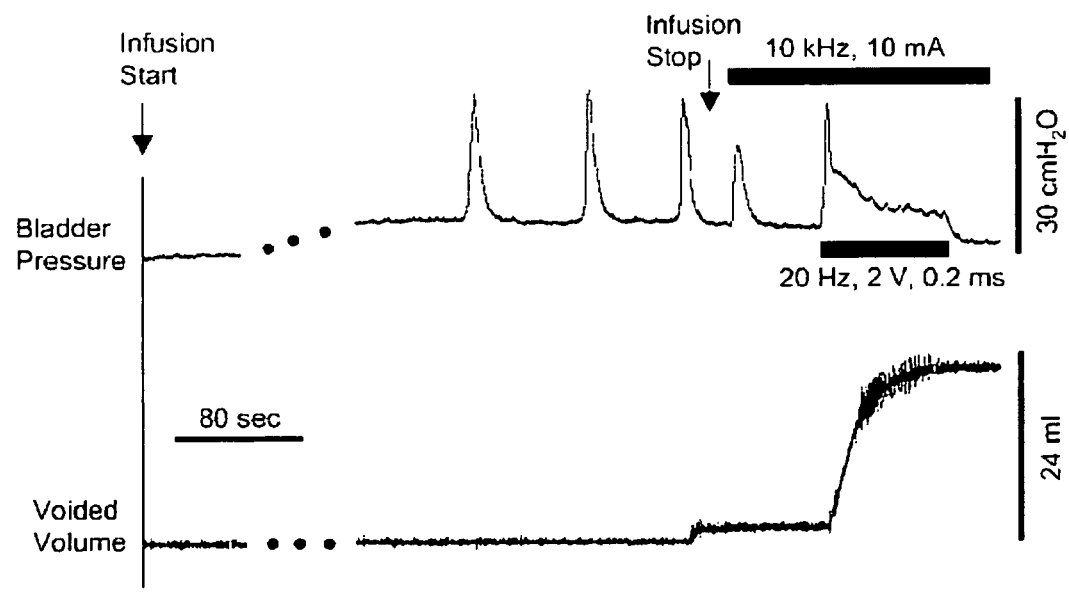

This study revealed marked differences in voiding reflexes in chloralose-anesthetized cats with an intact spinal cord and in chronic SCI cats (FIGS. 3-6). Chronic SCI cats exhibited a reduced voiding efficiency and urethral flow rate that is attributable to low amplitude and short duration reflex bladder contractions as well as to poor coordination between the urinary bladder and the EUS. Electrical stimulation of afferent axons in the pudendal nerve reversed the defect in bladder contractions, eliciting large amplitude, long duration, reflex bladder contractions but still did not improve voiding efficiency due to simultaneous activation of motor pathways to the EUS (FIG. 7). However when the motor pathways were blocked by high-frequency stimulation (10 kHz) of the pudendal nerves unilaterally or bilaterally, voiding efficiency markedly improved (FIGS. 5 and 8). These results raise the possibility that combined pudendal afferent nerve stimulation and efferent nerve block might be useful in promoting voiding in people with SCI.

Voiding Reflex in Normal Cats Versus Voiding Reflex in Chronic SCI Cats

In normal cats, the pontine micturition center (PMC) located in the rostral pons coordinates bladder and EUS activity during voiding. During bladder filling when afferent input to the PMC reaches the threshold for triggering micturition (i.e., bladder capacity) descending projections from the PMC induce a sustained bladder contraction with a simultaneous EUS relaxation resulting in release of a large volume of fluid from the bladder (see FIG. 3A). This spinobulbospinal voiding reflex produces a fast flow rate (FIG. 4B) with a high voiding efficiency (FIG. 5). However, in chronic SCI cats the contribution of the PMC is lost and voiding is mediated purely by a spinal reflex. This spinal voiding reflex can only induce a series of small, short-lasting bladder contractions (FIGS. 3B, 4A, and 6) when the bladder volume reaches a threshold level, but only a very small percentage of bladder volume (FIG. 5) is released at a slow flow rate (FIG. 4B). The inefficiency of voiding in chronic SCI cats might be attributable to two different spinal reflexes. One is the bladder-to-bladder spinal reflex, and the other is the bladder-to-pudendal spinal reflex. The bladder-to-bladder spinal reflex is brief (see FIGS. 3B and 6) and generates smaller bladder pressures (see FIG. 4A) compared to the spinobulbospinal reflex in spinal intact cats. In awake, chronic SCI cats, similar short duration, small amplitude bladder contractions were also observed during voiding. This indicates that the bladder-to-bladder spinal reflex is very different from the bladder-to-bladder supraspinal reflex mediated by the PMC.

Figure 6:
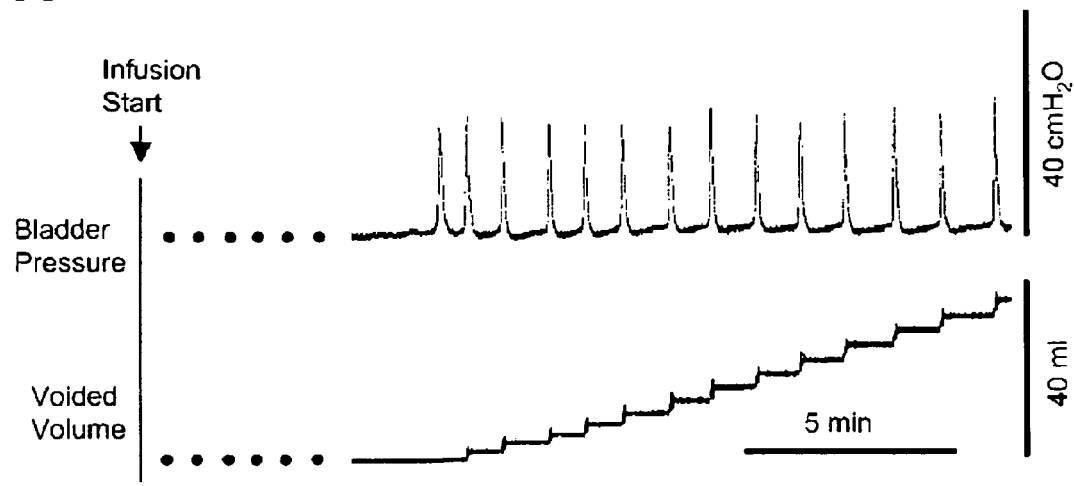
FIG. 6. Voiding reflex induced by bladder distension in chronic SCI cats. (A) In a chronic SCI cat (9 months after SCI), the bladder was continuously infused at 3 ml/min. At the first voiding contraction, a total of 20 ml was infused into the bladder. At the last voiding contraction, a total of 57 ml was infused, but a total of 38 ml was voided by a series of short-lasting bladder contractions resulting in 19 ml residual volume in the bladder. (B) In the same chronic SCI cat as shown in FIG. 3B, the bladder capacity was increased to 124 ml at the infusion stop by the inhibitory 3 Hz pudendal nerve stimulation. The black bar under the bladder pressure trace indicates the duration of the pudendal nerve stimulation. After stopping the 4 ml/min infusion and the stimulation, several short-lasting bladder contractions voided a total of 31 ml.
Figure 6:
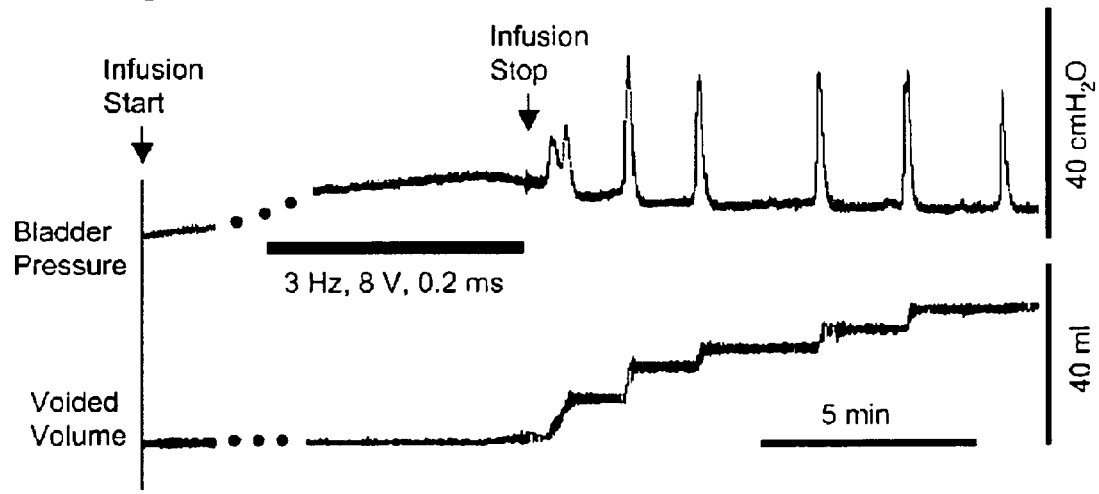

Once it is triggered, the supraspinal reflex can maintain a large amplitude bladder contraction and sustain the bladder pressure as the bladder volume becomes smaller during the voiding (FIG. 3A). This sustained bladder contraction is driven by a constant input from the PMC to the parasympathetic neurons in the sacral spinal cord. However, the bladder-to-bladder spinal reflex lacks of this sustained input. Instead, the bladder-to-bladder spinal reflex is directly driven by the tension receptors in the bladder wall. Once voiding occurs, and bladder volume and tension in the bladder wall are reduced, attenuation of afferent input to spinal cord seems to turn off the reflex (FIGS. 3B and 6). Therefore, the bladder-to-bladder spinal reflex cannot sustain the bladder contraction as the bladder volume declines during voiding. In addition to the weak bladder-to-bladder spinal reflex, voiding inefficiency in chronic SCI cats is also caused by a bladder-to-pudendal spinal reflex. This reflex triggers EUS contractions and increases urethral outlet resistance during a bladder contraction (i.e., detrusor sphincter dyssynergia), which further reduces the ability of the distension-induced, small, transient bladder contractions to eliminate fluid from the bladder (see FIGS. 3B and 6).

Although it seems unlikely that the surgical manipulation on the pudendal nerves caused the small, transient bladder contractions in the chronic SCI cats, it is worth noting that the pudendal nerves in normal animals were not surgically manipulated and this might have contributed to the differences in bladder activity between normal and SCI cats. Thus the factors contributing to the differences between the bladder-to-bladder spinal reflex in chronic SCI cats and the bladder-to-bladder spinobulbospinal reflex in normal cats need to be further investigated.

Pudendal-to-Bladder Spinal Reflex

In this study, we have demonstrated that an excitatory pudendal-to-bladder spinal reflex exists in chronic SCI cats. This spinal reflex can generate sustained bladder contractions (FIG. 7) strong enough to induce efficient voiding if the EUS contraction can be prevented (FIG. 5 and FIG. 8). The 20 Hz pudendal nerve stimulation provides a sustained excitatory input to the sacral parasympathetic neurons that is similar to what is provided by the PMC. However, it appears that this excitatory pudendal-to-bladder spinal reflex is also dependent on bladder volume. At a smaller bladder volume, it becomes weaker (see FIG. 7). Thus it is likely that there is a positive interaction between pudendal and bladder afferent inputs to the spinal micturition reflex circuitry. The excitatory pudendal-to-bladder spinal reflex could be induced during distal blockade of the pudendal nerve (see FIG. 8) indicating that this excitatory spinal reflex is activated by stimulating the afferent fibers in the pudendal nerve rather than the efferent fibers.

The pudendal-to-bladder spinal reflex in chronic SCI cats can be either excitatory or inhibitory depending on the stimulation frequency. Previous studies (Walter J S, Wheeler J S, Robinson C J, et al. Inhibiting the hyperreflexic bladder with electrical stimulation in a spinal animal model. Neurourol Urodyn 1993; 12:241-53; Mazieres L, Jiang C, Lindstrom S. Bladder parasympathetic response to electrical stimulation of urethral afferents in the cat. Neurourol Urodyn 1997; 16:471-2; Sundin T, Carlsson C A, Kock N G. Detrusor inhibition induced from mechanical stimulation of the anal region and from electrical stimulation of pudendal nerve afferents: An experimental study in cats. Investigative Urol 1974; 11:374-

8; Fall M, Erlandson B E, Carlsson C A, et al. The effect of intravaginal electrical stimulation on the feline urethra and urinary bladder: Neuronal mechanisms. Scand J Urol Nephrol 1978; 44:19-30; and Lindstrom S, Fall M, Carlsson C A, et al. The neurophysiological basis of bladder inhibition in response to intravaginal electrical stimulation. J Urol 1983; 129:405-10) showed in both normal and SCI cats that an inhibitory pudendal-to-bladder reflex was induced by pudendal nerve stimulation at a frequency below 10 Hz (see also FIG. 6B). However, as demonstrated in this and our previous study (Tai C, Smerin SE, de Groat W C, et al. Pudendal-to-bladder reflex in chronic spinal-cord-injured cats. Exp Neurol 2006a; 197:225-34), the pudendal-to-bladder spinal reflex in chronic SCI cats becomes excitatory at a stimulation frequency of 20 Hz. Although the mechanism of this frequency dependence is unknown, it is clear that different stimulation frequencies must activate different spinal micturition reflex circuitry. Barrington (Barrington F J F. The component reflexes of micturition in the cat, Parts I and II. Brain 1931; 54:177-88 and Barrington F J F. The component reflexes of micturition in the cat, Parts III. Brain 1941; 64:239-43) identified a spinal reflex from urethra to bladder when urine flows through the urethra. He showed that this reflex can induce a bladder contraction when bladder volume is high. Meanwhile, Garry et al. (Garry R C, Roberts T D, Todd J K. Reflexes involving the external urethral sphincter in the cat. J. Physiol 1959; 149:653-65) reported that fluid flowing through the urethra could inhibit bladder activity when bladder volume was low. Since the urethra is innervated by the pudendal nerve, pudendal nerve stimulation at different stimulation frequencies might trigger the different urethra-to-bladder reflexes.

In acute SCI cats (i.e., within hours after spinal cord transection), pudendal nerve stimulation induced small (less than 20 cmH$_2$O) bladder contractions. (Boggs J W, Wenzel B J, Gustafson K J, et al. Spinal micturition reflex mediated by afferents in the deep perineal nerve. J Neurophysiol 2005; 93:2688-97 and Shefchyk S J, Buss R R. Urethral pudendal afferent-evoked bladder and sphincter reflexes in decerebrate and acute spinal cats. Neurosci Lett 1998; 244:137-40) However, the pudendal-to-bladder spinal reflex in acute SCI cats is excitatory regardless of the frequency of pudendal nerve stimulation, (Boggs J W, et al., J Neurophysiol 2005; 93:2688-97) which is very different from the effects in chronic SCI cats. This difference between acute and chronic SCI cats may be due to the fact that neuroplasticity in the spinal cord which underlines the emergence of excitatory bladder-to-bladder and pudendal-to-bladder spinal reflexes requires several weeks to fully develop. Neurogenic detrusor overactivity and detrusor sphincter dyssynergia that are indicators of spinal reorganization after SCI exist in chronic SCI animals and humans, but do not exist after acute SCI. Instead, acute SCI results in detrusor areflexia (i.e., loss of reflex bladder contractions), which may explain why only the excitatory pudendal-to-bladder reflex could be observed in acute SCI cats (Boggs J W, et al., J Neurophysiol 2005; 93:2688-97).

A recent study (Boggs J W, Wenzel B J, Gustafson K J, et al. Bladder emptying by intermittent electrical stimulation of the pudendal nerve. J Neural Eng 2006; 3:43-51) also showed that intermittent pudendal nerve stimulation at 33 Hz induced a voiding reflex in cats with an intact spinal cord. However, it is difficult to attribute this voiding solely to a spinal reflex in spinal intact cats, since the spinobulbospinal micturition reflex is intact and the PMC coordinates voiding once the bladder contraction is initiated by pudendal nerve stimulation. In addition pudendal nerve stimulation evokes a long latency reflex discharge on bladder postganglionic nerves in spinal intact cats, which is presumably mediated by a spinobulbospinal pathway because it is eliminated in chronic SCI cats. Therefore, an efficient voiding reflex is expected to be induced in spinal intact cats by pudendal nerve stimulation just like the voiding reflex induced by bladder distension in spinal intact cats (see FIGS. 3A and 5).

EUS Contractions Induced by 20 Hz Pudendal Nerve Stimulation

The urethral outlet resistance in the chronic SCI cats could be generated by three different mechanisms of EUS activation. The first one is due to the direct activation of the pudendal efferent input to the EUS by the 20 Hz pudendal nerve stimulation. This could cause a strong EUS contraction that blocks voiding even during a large amplitude bladder contraction (see FIG. 7). The second type of EUS contraction is due to the excitatory bladder-to-pudendal spinal reflex (i.e., detrusor sphincter dyssynergia). This spinal reflex not only contributes to the low voiding efficiency in the chronic SCI cats induced by bladder distension (see FIGS. 3B and 5), but also plays a role in inducing EUS contractions during the bladder contractions induced by 20 Hz pudendal nerve stimulation. The third type of EUS contraction is due to the excitatory pudendal-to-pudendal spinal reflex. This spinal reflex which is distributed bilaterally could cause EUS contractions via the contralateral pudendal nerve even when the ipsilateral pudendal nerve is blocked. Compared to ipsilateral block, bilateral block of the pudendal nerves further increased voiding efficiency to a level that is not significantly different from spinal intact cats (see FIG. 5). This shows that the EUS contraction was partially induced by reflex efferent activity in the contralateral pudendal nerve. Due to the three types of EUS contractions induced during 20 Hz pudendal nerve stimulation, voiding efficiency was maximal during simultaneous block of the pudendal nerves bilaterally (see FIG. 5).

A previous study (Sawan M, Hassouna M M, Li J S, et al. Stimulator design and subsequent stimulation parameter optimization for controlling micturition and reducing urethral resistance. IEEE Trans Rehabil Eng 1996; 4:39-46) in chronic SCI dogs claimed that complete bladder emptying could be achieved without dorsal rhizotomy by stimulating the sacral spinal roots at frequencies of 300-350 Hz to fatigue the EUS. However, another study (Ishigooka M, Hashimoto T, Sasagawa I, et al. Modulation of the urethral pressure by high-frequency block stimulation in dogs. Eur Urol 1994; 25:334-7) showed that pudendal nerve stimulation between 100 and 1,000 Hz could only fatigue the EUS by 30-45% since the majority of the EUS muscles are slow twitch fibers that are fatigue resistant. Further, fatigue stimulation becomes gradually less effective for long-term use since the sphincter could change to become more fatigue resistant (Schmidt R A. Neural prostheses and bladder control. IEEE Eng Med Biol Mag 1983; 2:31-4).

Safety of the High-Frequency Blocking Stimulation

Although the effectiveness of biphasic, high-frequency (10 kHz), charge-balanced, electrical stimulation of the pudendal nerves has been demonstrated in this and previous studies, (Tai C, et al., J Urol 2004; 172:2069-72 and Tai C, et al., J Urol 2005; 174:782-6) it remains to be determined if this stimulation is safe for long-term use. It is known that biphasic, charge-balanced, electrical pulses will cause less damage to the nervous tissue than uniphasic pulses (Agnew W F, McCreery D B. Neural prostheses: Fundamental studies. Englewood Cliffs, N.J.: Prentice-Hall; 1990), but the long-term use of this nerve blocking method needs to be evaluated in animal studies before testing in humans. Acute damage of the pudendal nerve caused by high-frequency biphasic stimulation seems unlikely since our previous study (Tai C, et al., J Urol 2005; 174:782-6) in animals showed that this blocking stimulation applied repetitively (1 min stimulation every 1-3 min) during a period of 43 min did not alter the neurally evoked EUS response. The potential human application of the high-frequency nerve blocking method will be limited to 3-5 times a day for 1-3 min each time to induce voiding in SCI people. The risk of nervous tissue damage is low when the nerve is only stimulated for a short time during 24 hr (Agnew W F, McCreery D B. Neural prostheses: Fundamental studies. Englewood Cliffs, N.J.: Prentice-Hall; 1990).

Human Application

Although intermittent voiding responses in quadruped animals is associated with squirting of urine and territorial marking, which is different from voiding in humans that occurs as a steady stream of urine, intraurethral electrical stimulation at a frequency of 20 Hz excited the bladder in people with complete SCI (Gustafson K J, Creasey G H, Grill W M. A catheter based method to activate urethral sensory nerve fibers. J Urol 2003; 170:126-9 and Gustafson K J, Creasey G H, Grill W M. A urethral afferent mediated excitatory bladder reflex exists in humans. Neurosci Lett 2004; 360:9-12). Since the urethra is innervated by the pudendal nerve, 20 Hz stimulation has been shown to be effective in activating the bladder in humans (See, e.g., U.S. Pat. No. 7,047,078). Inducing a voiding reflex after SCI by pudendal nerve stimulation with simultaneous blockage would not require sacral posterior root rhizotomy, thereby improving on the Brindley's method by preserving the spinal reflexes for bowel, bladder, and sexual functions in people with SCI. Meanwhile, eliminating the requirement of sacral posterior root rhizotomy also provides hope for people with SCI to benefit from any advance in neural regeneration and repair techniques in the future.

The spinal surgery that is needed in Brindley's method to access the spinal roots would not be necessary either, because only the pudendal nerves would be exposed to implant stimulating electrodes. Compared to spinal surgery, the pudendal nerves can be more easily accessed with minimal surgery (see, e.g., Schmidt R A. Technique of pudendal nerve localization for block and stimulation. J Urol 1989; 142:1528-31 and Spinelli M, Malaguti S, Giardiello G, et al. A new minimally invasive procedure for pudendal nerve stimulation to treat neurogenic bladder: Description of the method and preliminary data. Neurourol Urodyn 2005; 24:305-9).

Conclusions

In summary, our studies have revealed that significant differences exist between the spinal micturition reflex in chronic SCI cats and the spinobulbospinal micturition reflex in spinal intact cats. In addition voiding is very inefficient in chronic SCI cats as in SCI people. The improvement in voiding induced by pudendal nerve stimulation and block in chronic SCI cats provided further evidence indicating the feasibility of a new neuroprosthetic device to restore micturition function in people after SCI.

Example 2

In this study in chronic paraplegic cats we evaluated an alternative method to regulate bladder function involving electrical stimulation of somatic afferent nerves innervating the perigenital region.

The perigenital skin area is innervated by the pudendal nerve. Electrical stimulation of the pudendal nerve at low frequencies (1-10 Hz) (Tai C, Smerin SE, de Groat W C, Roppolo JR. Pudendal-to-bladder reflex in chronic spinal-cord-injured cats. Exp Neurol 197: 225-234, 2006b and Walter J S, Wheeler, J S, Robinson C J, Wurster R D. Inhibiting the hyperreflexic bladder with electrical stimulation in a spinal animal model. Neurourol Urodynam 12: 241-253, 1993) can inhibit the bladder in adult chronic SCI cats, but at high frequencies (20-30 Hz) can excite the bladder (Tai C, Smerin SE, de Groat W C, Roppolo JR. Pudendal-to-bladder reflex in chronic spinal-cord-injured cats. Exp Neurol 197: 225-234, 2006b). However, the pudendal nerve innervates many areas in the pelvic region including the urethra, anal canal, anal and urethral sphincters, and skin. Whether electrical stimulation applied to the perigential skin area can mimic the effect of pudendal nerve stimulation and induce both inhibitory and excitatory effects on bladder in the chronic SCI cats is uncertain, since the mechanical perigenital stimulation is primarily excitatory after SCI (de Groat W C, Araki I, Vizzard M A, Yoshiyama M, Yoshimura N, Sugaya K, Tai C, Roppolo J R. Developmental and injury induced plasticity in the micturition reflex pathway. Behavioural Brain Res. 92: 127-140, 1998 and Tai C, Miscik C L, Ungerer T D, Roppolo J R, de Groat W C. Suppression of bladder reflex activity in chronic spinal cord injured cats by activation of serotonin 5-HT$_{1A}$ receptors. Exp Neurol 199: 427-437, 2006a).

In humans after chronic SCI bladder inhibition can also be elicited by electrical stimulation of the dorsal penile/clitoral nerve (a branch of pudendal nerve) using skin electrodes (Andre R, Schmid D M, Curt A, Knapp P A, Schurch B. Afferent fibers of the pudendal nerve modulate sympathetic neurons controlling the bladder neck. Neurourol Urodynam 22: 597-601, 2003; Hansen J, Media S, Nohr M, Biering-Sorensen F, Sinkjaer T, Rijkhoff N J M. Treatment of neurogenic detrusor overactivity in spinal cord injured patients by conditional electrical stimulation. J Urol 173: 2035-2039, 2005; Kirkham A P S, Shah N C, Knight S L, Shah P J R, Craggs Md. The acute effects of continuous and conditional neuromodulation on the bladder in spinal cord injury. Spinal Cord 39: 420-428, 2001; Previnaire J G, Soler J M, Perrigot M. Is there a place for pudendal nerve maximal electrical stimulation for the treatment of detrusor hyperreflexia in spinal cord injury patients? Spinal Cord 36: 100-103, 1998; Previnaire J G, Soler J M, Perrigot M, Boileau G, Delahaye H, Schumacker P, Vanvelcenaher J, Vanhee J L. Short-term effect of pudendal nerve electrical stimulation on detrusor hyperreflexia in spinal cord injury patients: importance of current strength. Paraplegia 34: 95-99, 1996; Vodusek D B, Light J K, Libby J M. Detrusor inhibition induced by stimulation of pudendal nerve afferents. Neurourol Urodynam 5: 381-389, 1986; and Wheeler J S, Walter J S, Zaszczurynski P J. Bladder inhibition by penile nerve stimulation in spinal cord injury patients. J Urol 147:100-103, 1992), indicating an inhibitory perigenital-to-bladder spinal reflex might also exist in adult chronic SCI cats. An effective, non-invasive method that is able to either inhibit or induce bladder activity would improve the current clinical management of the bladder function after SCI. The possibility of using electrical stimulation of the perigenital skin area to activate the inhibitory perigenital-to-bladder reflex at one frequency, but to activate the re-emerged excitatory perigenital-to-bladder reflex at another frequency was investigated in this study in adult chronic SCI cats.

In order to eliminate possible effects of anesthesia on the perigenital-to-bladder reflexes which may influence voiding efficiency, experiments were performed under awake conditions so that the results would be directly comparable to the voiding in neonates. This condition would also produce results more relevant to the clinical situation.

Methods

Spinal Cord Transection and Animal Care

Four female adult cats (2.8-3.4 kg) were spinalized under isoflurane anesthesia (2-3% in $O_2$) using aseptic surgical techniques. After performing a dorsal laminectomy at T9-T10 vertebral level, a local anesthetic (lidocaine 1%) was applied to the surface of the spinal cord and then injected into the cord through the dura. The spinal cord was then cut completely and a piece of gel foam was placed between the cut ends (usually a separation of 2-3 mm). The muscle and skin were sutured and after full recovery from anesthesia the animal was returned to its cage. Following spinal transection, the bladder was emptied daily by manual expression. If manual expression was not successful, a sterile catheter (3.5 F) was inserted through the urethra to empty the bladder. Ketaprofen (2 mg/kg s.c., twice a day for 3 days) and antibiotics (Clavamox, 15-20 mg/kg s.c. for 7 days) were given following surgery. Experiments were conducted beginning at least 4-5 weeks following spinal cord transection. The cats were used for multiple experiments at a maximal frequency of twice per week. After each experiment the animal was given 150 mg/kg of ampicillin subcutaneously. Bladder infection rarely occurred.

Experimental Setup

Figure 9:
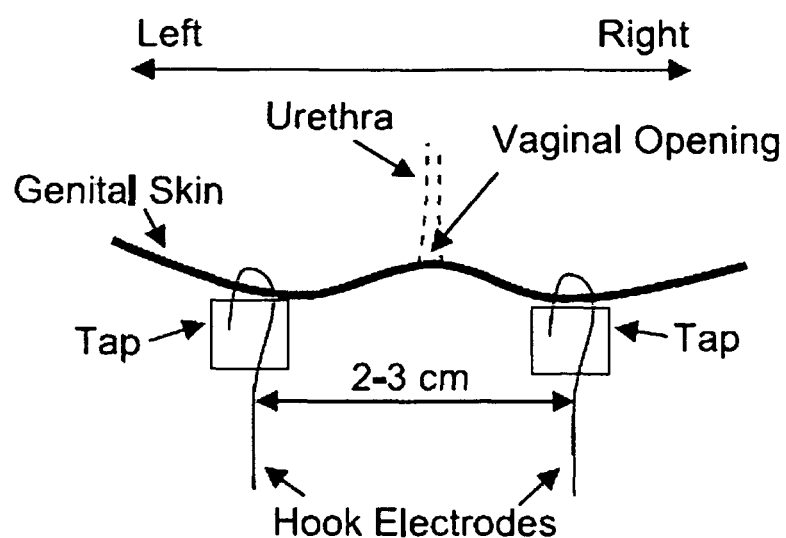
FIG. 9. Schematic drawing of the electrode attachment described in Example 2.

A sterile double lumen balloon catheter (7 F) was inserted through the urethra into the bladder of the chronic SCI cats without anesthesia. The balloon was distended by 2 ml of air and then positioned at the bladder neck by gently pulling the catheter back. The balloon prevented leakage of the fluid from the bladder. One lumen of the catheter was connected to a pump to infuse the bladder with sterile saline at a rate of 2 ml/min, and the other lumen was connected to a pressure transducer to measure the pressure change in the bladder. As shown in FIG. 9, a pair of sterilized hook electrodes (made from 23G needles) was attached to the skin (about 1 mm penetration into the skin with 2-4 mm contact) on the left and right sides of the vagina approximately 1-1.5 cm from the vaginal opening. A piece of medical tape was applied between the electrode tip and the exposed length of the electrode in order to fix the electrode in place. The electrodes were soldered to a pair of wires that were connected to a stimulator to deliver electrical stimulation. Due to the complete spinal transection, the animals did not sense either bladder catheterization or electrical stimulation. During the experiment (usually 4-5 hours) the animals rested comfortably in a padded animal transport carrier. Since the animal was free to move in the carrier, bladder pressure recordings that were disrupted by the animal's movements were discarded. At the end of the experiment the catheter was withdrawn and the electrodes were detached.

Some experiments were conducted to evaluate voiding induced by electrical or mechanical perigenital stimulation. In these experiments the bladder was not catheterized. The voided volume was collected using a funnel. The animal was lying quietly on a table during the voiding tests.

Stimulation Protocol

Uniphasic pulses (0.2 ms pulse width) of different intensities (1-30 V) and frequencies (0.5-50 Hz) were delivered to the perigenital skin area via the attached electrodes using a stimulator (Grass Medical Instruments, S88) with a stimulus isolator (Grass Medical Instruments, SIU5).

In the first group of experiments, the bladder was infused with sterile saline to one of two different volumes: (1) a volume slightly above the micturition threshold to induce large amplitude (greater than 30 $cmH_2O$), rhythmic reflex bladder contractions (see FIGS. 10A and 11A); or (2) a volume slightly below the micturition threshold so that large amplitude, reflex bladder contractions did not occur (see FIG. 12A). During the large amplitude rhythmic bladder contractions, electrical perigenital stimulation was applied in order to determine the effective stimulation parameters to inhibit the bladder. The stimulation duration was longer than the period of at least two bladder contractions in order to clearly demonstrate an inhibitory effect. The effective stimulation parameters to induce bladder contractions were determined when bladder volume was below micturition threshold. A stimulation duration of 20-50 seconds was used which was longer than the period of the induced bladder contractions. Different stimulation parameters were tested in a random order, but are shown in ascending intensity and/or frequency for clarity.

In the second group of experiments, the most effective stimulation frequencies identified during isovolumetric recordings (7 Hz for inhibition, but 30 Hz for excitation) were tested during a cystometrogram (CMG, see FIG. 13A) which consisted of a slow infusion of saline (2 ml/min) starting with an empty bladder to determine functional bladder capacity and examine bladder reflex activity during filling. Two or three control CMGs were performed without stimulation to obtain the control values and evaluate the reproducibility. Then, either inhibitory or excitatory perigenital stimulation was applied during the CMG to evaluate the inhibitory or excitatory effects by measuring the change in bladder capacity. Stimulation and infusion were stopped after occurrence of the first micturition reflex contraction, which was defined as the first large amplitude (greater than 30 $cmH_2O$), long duration (greater than 20 seconds) reflex bladder contraction accompanied by hindlimb stepping movements. Previous studies (Tai C, Miscik C L, Ungerer T D, Roppolo J R, de Groat W C. Suppression of bladder reflex activity in chronic spinal cord injured cats by activation of serotonin 5-$HT_{1A}$ receptors. Exp Neurol 199: 427-437, 2006a and Thor K B, Roppolo J R, de Groat W C. Naloxone induced micturition in unanesthetized paraplegic cats. J Urol 129: 202-205, 1983) showed that hindlimb stepping movement was a useful marker for the occurrence of a micturition reflex in awake chronic SCI cats. Bladder capacity is defined as the volume threshold for inducing a micturition reflex during a CMG. A control CMG was performed at the end of the test to confirm the recovery of the micturition reflex. The bladder was emptied after each CMG and a 5-10 minute rest period was inserted between CMGs to allow the bladder reflexes to recover.

In the third group of experiments, the ability of the excitatory electrical perigenital stimulation (30 Hz) to induce bladder contractions at different bladder volumes was evaluated. Short periods (20-50 seconds) of stimulation were applied during the CMGs at intervals representing 4-8 ml increments in the infused volume. Similar tests were also performed using mechanical perigenital stimulation that is known to be excitatory in chronic SCI cats (Tai C, Miscik C L, Ungerer T D, Roppolo J R, de Groat W C. Suppression of bladder reflex activity in chronic spinal cord injured cats by activation of serotonin 5-$HT_{1A}$ receptors. Exp Neurol 199: 427-437, 2006a). The mechanical perigenital stimulation was performed by repeatedly light stroking (2-3 times/second for 20-50 seconds, stroke length 2-3 cm) the perigenital skin area using a cotton swab. The bladder contractions induced by electrical or mechanical perigenital stimulation were compared.

Excitatory electrical (30 Hz) and mechanical perigenital stimuli were also used to induce voiding in the awake chronic SCI cats. Voiding induced by electrical perigenital stimulation was tested in 3 cats (2 times in each cat). The bladder was first infused to its capacity using a urethral catheter. Then the catheter was withdrawn and several minutes were allowed for any spontaneous voiding to occur. If no spontaneous voiding occurred or after it was finished, a short duration (10-20 seconds) electrical perigenital stimulation was repeatedly applied to induce voiding. Stimulation was continued until voiding stopped. Then the bladder was emptied by manual expression to measure residual volume. If manual expression failed, a sterile urethral catheter (3.5 F) was used to empty the bladder. Voiding tests were also performed using repeated, short duration (10-20 seconds) mechanical perigenital stimulation with the overnight residual bladder volume as the initial bladder volume.

Data Analysis

For the analysis of rhythmic bladder activity, the area under bladder pressure curve, the inter-contraction interval (ICI), and the average bladder contraction amplitude were measured during the electrical stimulation and were normalized to the measurements during the same time period prior to the stimulation. The contraction frequency is represented as 1/ICI because ICI was an infinite value when complete bladder inhibition occurred. For the bladder contractions induced by electrical stimulation at a bladder volume below the capacity, the areas under the induced bladder pressure curves were measured and normalized to the maximal measurement during each experimental trial. Small amplitude (5-30 $cmH_2O$), short duration (less than 20 seconds) pre-micturition contractions (PMCs) also occurred during CMGs prior to the large amplitude micturition contraction in chronic SCI cats (Tai C, Miscik C L, Ungerer T D, Roppolo J R, de Groat W C. Suppression of bladder reflex activity in chronic spinal cord injured cats by activation of serotonin 5-$HT_{1A}$ receptors. Exp Neurol 199: 427-437, 2006a). The bladder capacity, the volume threshold to induce the first PMC, the average PMC amplitude, and the number of PMCs per minute were measured and normalized to the measurements during the first control CMG. The variability of control CMGs were evaluated by comparing the measurements from the repeated control CMGs to the first control CMG. The amplitude of bladder contractions induced by electrical or mechanical perigenital stimulation during a CMG were compared at different bladder volumes that were normalized to the bladder capacity in each experiment, and then grouped into bins representing 10% increments in bladder volume. For the voiding tests, the voiding efficiency was calculated as the voided volume divided by the total volume (voided volume+residual volume). Repeated measurements in the same animal during different experiments were averaged. The normalized data from different animals are presented as mean±SEM. One sample Student t-test and paired Student t-test were used to detect statistical significance (P<0.05) except in two instances as indicated in the text where unpaired Student t-test was used. Linear regression analysis (95% confidence interval) and ANOVA analysis were used to determine whether the amplitude of bladder contractions induced by perigenital stimulation increased as the bladder volume increased.

Results

Reflex Bladder Activity in Awake Chronic SCI Cats

In awake chronic SCI cats, infusion of saline into the bladder at a rate of 2 ml/min when the bladder neck was blocked with a balloon catheter produced an immediate small increase in baseline bladder pressure (3-8 $cmH_2O$) and later three types of reflex bladder activity: (1) low amplitude (5-30 $cmH_2O$), transient (10-20 second duration) increases in bladder pressure (termed pre-micturition contractions—PMCs, see FIG. 13A) that occurred in the absence of hindlimb movements, (2) large amplitude (30-100 $cmH_2O$, 20-100 second duration) increases in bladder pressure (micturition contractions, see FIG. 13A) that were accompanied by rhythmic alternating movements of the hindlimbs resembling stepping movements, and large amplitude rhythmic isovolumetric contractions (1-3/min, 30-100 $cmH_2O$ in amplitude, 20-100 second duration, see FIG. 10A and FIG. 11A) that persisted after the bladder infusion was stopped at the end of a CMG when the bladder volume was above the micturition threshold (20-120 ml) and the first micturition contraction was induced (see FIG. 13A and FIG. 14A). The rhythmic hindlimb movements were also elicited by manual compression of the bladder when attempting to express urine during daily nursing care or during voiding induced by tactile stimulation of the perigenital region. The association of somatic reflexes with voiding has also been reported in previous studies (Tai C, Miscik C L, Ungerer T D, Roppolo J R, de Groat W C. Suppression of bladder reflex activity in chronic spinal cord injured cats by activation of serotonin 5-HT1A receptors. Exp Neurol 199: 427-437, 2006 and Thor K B, Roppolo J R, de Groat W C. Naloxone induced micturition in unanesthetized paraplegic cats. J Urol 129: 202-205, 1983) and is a useful marker for the occurrence of a micturition reflex. Because some experiments were performed with the urethral outlet closed which prevents elimination of the bladder contents, the simultaneous occurrence of a large amplitude bladder contraction and hindlimb movements was used as an indicator of the first micturition reflex during the CMG (see FIG. 13A and FIG. 14A). The cystometric parameters were relatively constant in the same animal over the course of many experiments during a several week period.

2. Inhibitory Perigenital-to-Bladder Spinal Reflex

Figure 10A:
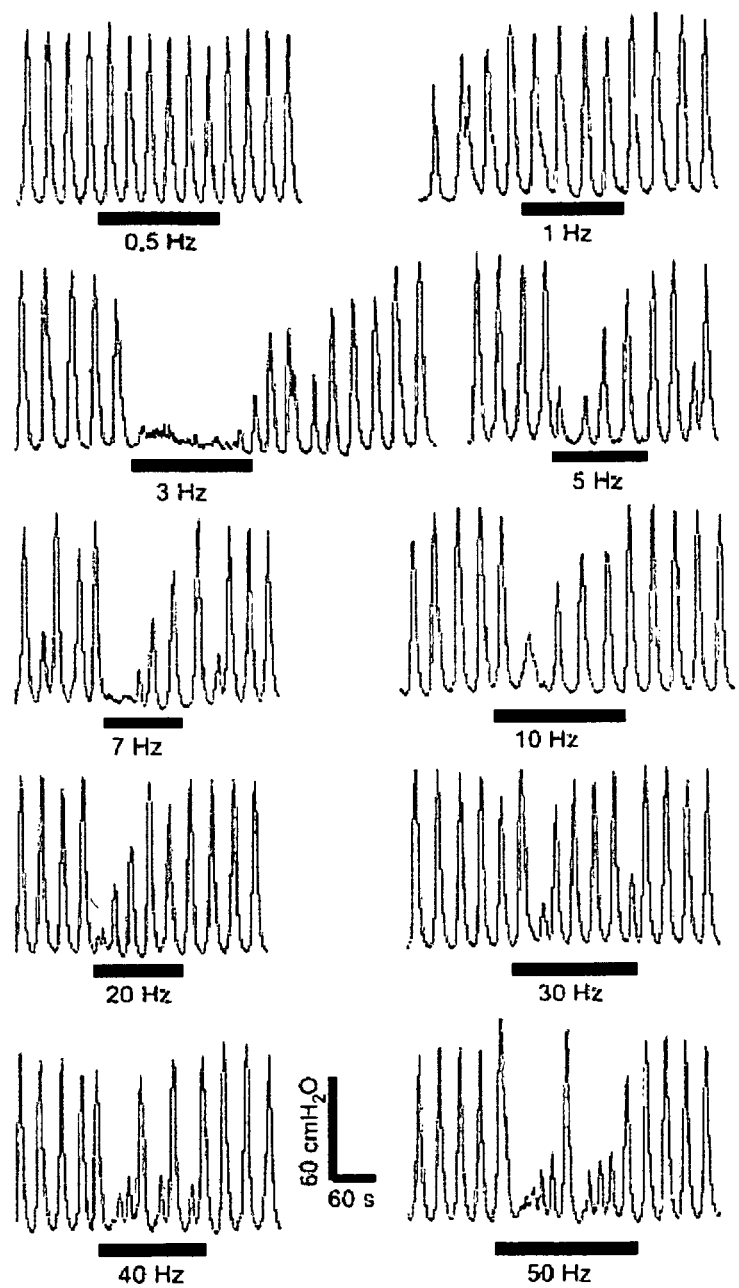
FIG. 10. Frequency-dependent inhibitory effect on rhythmic bladder activity induced by electrical perigenital stimulation. A: effect on bladder pressure traces at different stimulation frequencies. The black bars under bladder pressure traces mark the stimulation duration. B: area under bladder pressure curve. C: reciprocal of intercontraction interval (1/ICI). D: average bladder contraction amplitude. Bladder responses during stimulation were normalized to the response before stimulation in B-D. Stimulation: 30 V in A, 5-30 V in B-D; 0.2-ms pulse width. The calibration bars in A apply to all bladder pressure recordings. *Statistical significance (P<0.05); n=3.
Figure 10B:
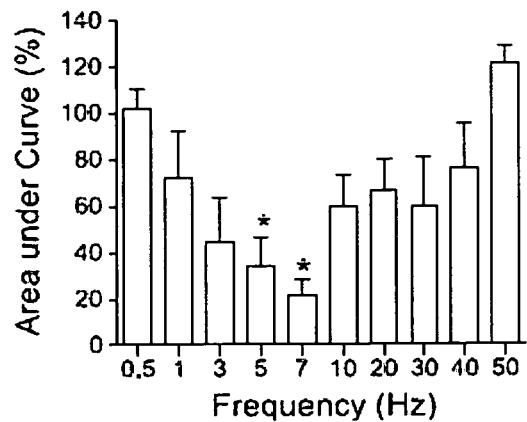
Figure 10C:
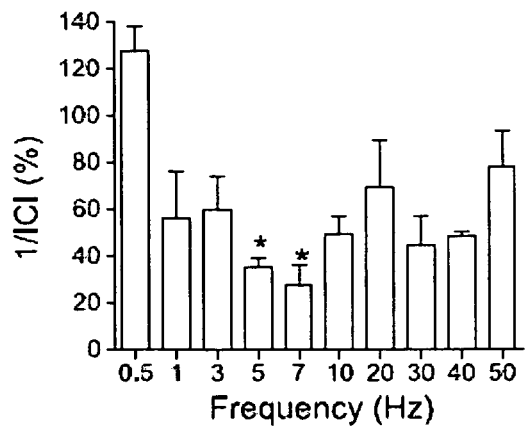
Figure 10D:
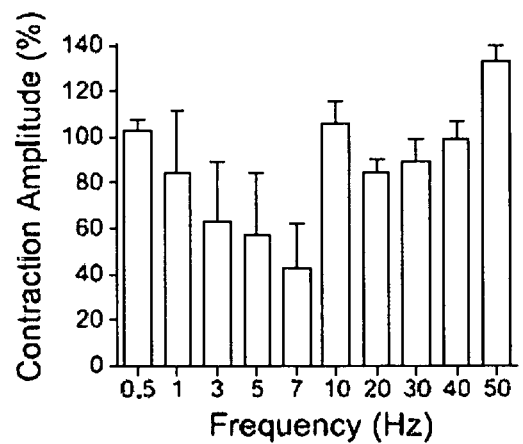

The inhibitory effect of electrical perigenital stimulation on large amplitude, rhythmic reflex bladder activity in awake chronic SCI cats was dependent on stimulation frequency (0.5-50 Hz, FIG. 10A). At stimulation frequencies of 5 Hz and 7 Hz, the electrical perigenital stimulation significantly (P<0.05) reduced the area under the bladder contraction curves (70-80%, FIG. 10B) and decreased the frequency (1/ICI) of the rhythmic bladder contractions (70-80%, FIG. 10C), but not the average contraction amplitude (P>0.05, FIG. 10D) compared to the bladder activity prior to the stimulation.

Figure 11A:
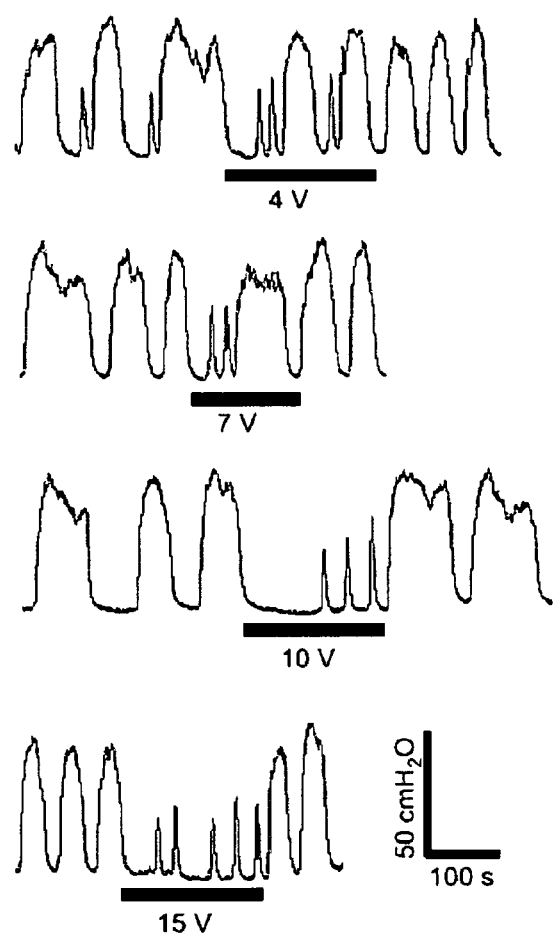
FIG. 11. Intensity-dependent inhibitory effect on rhythmic bladder activity induced by electrical perigenital stimulation. A: effect on bladder pressure traces at different intensities. The black bars under bladder pressure traces mark the stimulation duration. B: area under bladder pressure curve. C: reciprocal of ICI (1/ICI). D: average bladder contraction amplitude. Bladder response during stimulation was normalized to the response before stimulation in B-D. Stimulation: 7 Hz; 0.2-ms pulse width. The calibration bars in A apply to all bladder pressure recordings. *Statistical significance (P<0.05); n=3.
Figure 11B:
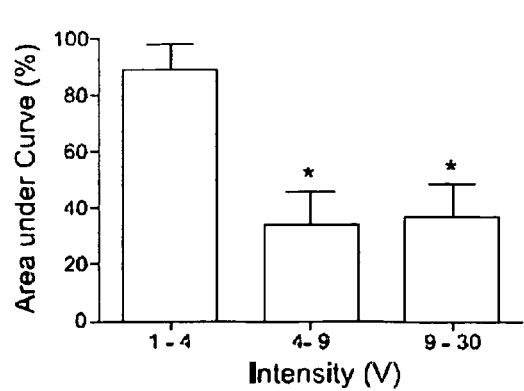
Figure 11C:
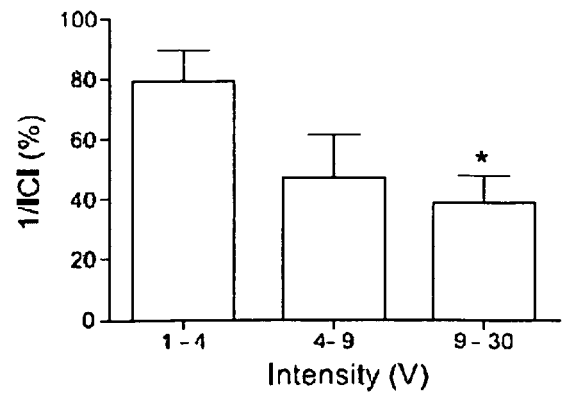
Figure 11D:
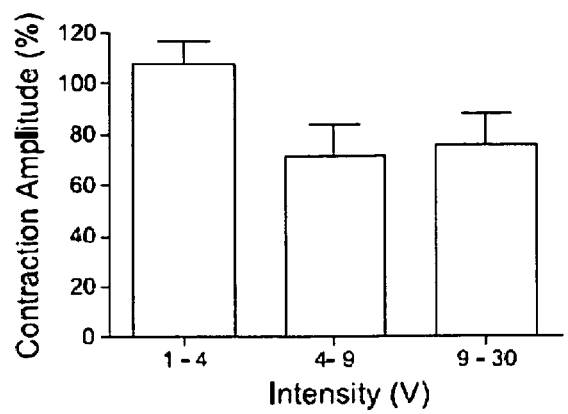

The inhibition of large amplitude, rhythmic reflex bladder activity at a stimulation frequency of 7 Hz was also dependent on stimulation intensity (FIG. 11A). At an intensity above 4 V, the stimulation significantly (P<0.05) reduced the area under the bladder contraction curves (70%, FIG. 11B). It also significantly (P<0.05) decreased the frequency of the rhythmic bladder contractions at an intensity above 9 V (60%, FIG. 11C), but the average contraction amplitude was not decreased significantly at any stimulation intensity (P>0.05, FIG. 11D).

3. Excitatory Perigential-to-Bladder Spinal Reflex

Figure 12A:
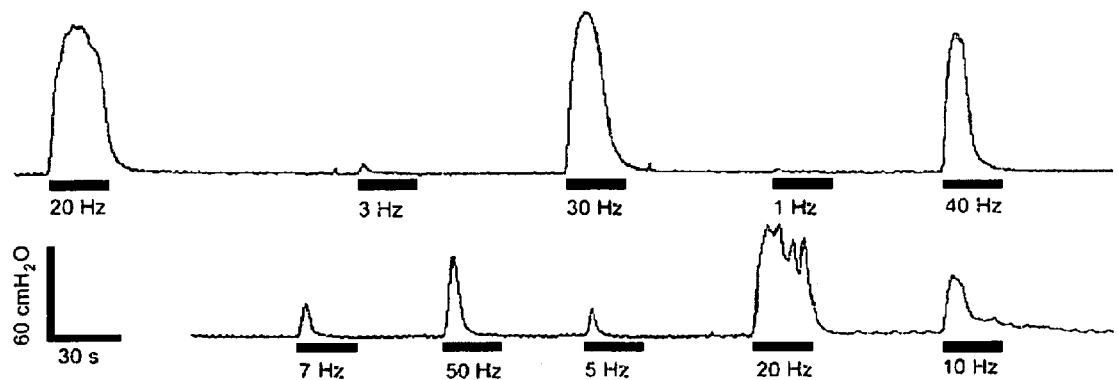
FIG. 12. Bladder contractions induced by electrical perigenital stimulation at different frequencies (A) or at different intensities (B). The area under bladder pressure curve is dependent on both stimulation frequency (C) and intensity (D). Stimulation: 15 V in A, 15-30 V in C; 30 Hz in B and D; 0.2-ms pulse width. The black bars under bladder pressure traces mark the stimulation duration. The response was normalized to the maximal response during each trial in C-D. The calibration bars in A apply to bladder pressure recordings in both A and B. *Statistical significance (P<0.05); n=4.
Figure 12B:
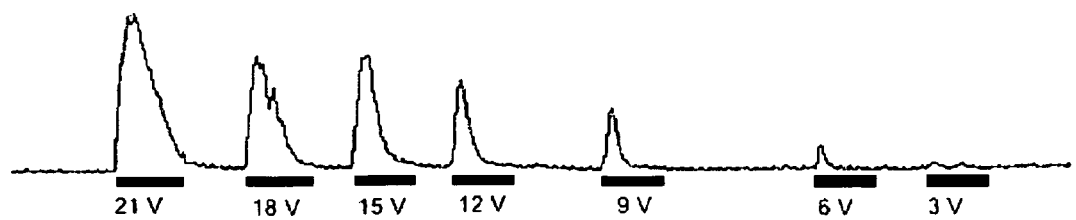
Figure 12C:
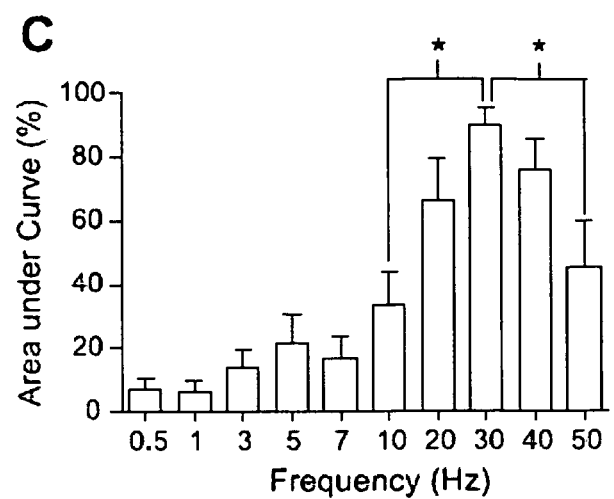
Figure 12D:
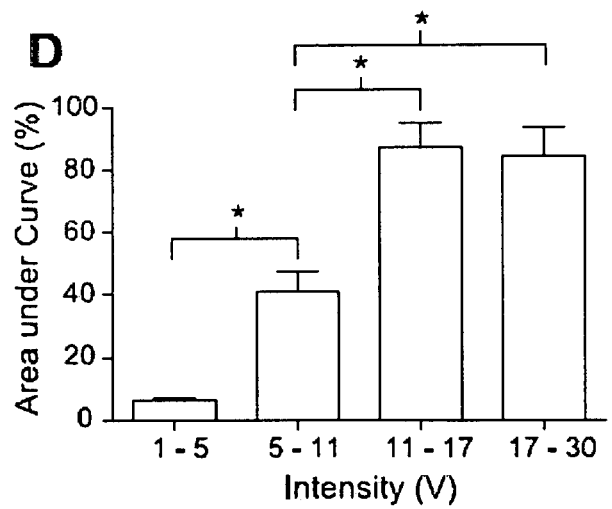

Although a bladder excitatory effect induced by electrical perigenital stimulation could not be observed during the large rhythmic bladder contractions (FIGS. 10 and 11), it became obvious when bladder volume was below micturition threshold and the large rhythmic bladder contractions were absent (FIGS. 12A and 12B). The excitatory perigenital-to-bladder reflex also depended upon the electrical stimulation frequency and intensity. Large amplitude (greater than 30 $cmH_2O$), long duration (greater than 20 sec) bladder contractions were induced by stimulation at frequencies between 20 Hz and 40 Hz (FIG. 12A). This excitatory effect was diminished as the stimulation intensity decreased (FIG. 12B). Electrical stimulation at 30 Hz produced bladder contractions significantly (P<0.05) larger than those produced at frequencies of 10 Hz or 50 Hz (FIG. 12C). The threshold intensity was about 5 V, but at least 11 V was required in order for a 30 Hz stimulation to induce a maximal bladder contraction (FIG. 12D).

4. Micturition Volume Threshold Modulated by Perigenital Stimulation

The threshold bladder volume (i.e. bladder capacity) to induce a micturition reflex contraction was significantly (P<0.05) increased 35±13% above control capacity by electrical perigenital stimulation at the optimal frequency (7 Hz) for inhibiting rhythmic contractions (FIGS. 13A and 13B). Stimulation at this frequency also significantly (P<0.05) increased (187±42% above control value) the bladder volume necessary to induce the first PMC (FIGS. 13A and 13C). However, the average amplitude and the frequency of PMCs (FIGS. 13D and 13E) and the amplitude of the first micturition contraction (see FIG. 13A) were not significantly (P>0.05) changed by the stimulation. Conversely, electrical perigenital stimulation at the optimal frequency (30 Hz) for inducing bladder excitation significantly (P<0.05) reduced bladder capacity 21±3% below the control capacity (FIGS. 14A and 14B).

5. Influence of Bladder Volume on the Excitatory Perigenital-to-Bladder Spinal Reflex The reflex bladder contractions evoked by electrical or mechanical stimulation of the perigenital region were elicited at different times during bladder filling to evaluate the influence of bladder volume on the reflex response. As shown in FIG. 15A when short periods (20 seconds) of electrical perigenital stimulation (15 V, 30 Hz) were repeatedly applied after 4 ml increments in bladder volume during a CMG, the stimulation induced large amplitude (greater than 30 cmH$_2$O) relatively consistent bladder contractions over a range of bladder volumes. Similarly, mechanical perigenital stimulation (repeatedly stroking the perigenital skin with a cotton swab at a rate of 2-3 times/second) could also induce large bladder contractions of relatively consistent amplitude at increasing bladder volumes (FIG. 15B). The average amplitude of the bladder contractions induced by either electrical (30 Hz) or mechanical stimulation (FIG. 15C and 15D) were not significantly influenced by the bladder volume (P>0.05, ANOVA analysis and linear regression analysis, N=3).

6. Voiding Induced by Perigenital Stimulation

In awake chronic SCI cats continuous electrical (30 Hz) or mechanical perigenital stimulation released fluid from the bladder. However, the voiding was inefficient probably due to detrusor sphincter dyssynergia, and usually only a small amount of bladder volume was released at the end of stimulation (i.e. a post-stimulus voiding). Therefore, short periods (10-20 seconds) of electrical or mechanical perigential stimulation were repeatedly applied (3-6 second interval). This released small amounts of fluid (1-10 ml) at the end of every period of stimulation. Usually 5-10 periods of stimulation over 1-5 minutes were sufficient to elicit the maximal bladder emptying.

Voiding induced by mechanical perigenital stimulation was tested using the overnight residual volume as the initial bladder volume. Total voided volume and the residual volume were measured in 3 cats over a 2 month period (FIG. 16A) together with the average amplitude of micturition contractions induced by bladder distension or by mechanical perigenital stimulation (FIG. 16B). The daily residual bladder volumes detected by manual expression or by emptying using a urethral catheter were relatively large ranging from 20-80 ml (see FIG. 16A). Meanwhile, frequent incontinent episodes resulting in the release of small amount of urine were also observed in these animals. Similar spontaneous bladder activity was also reported in a recent study (Pikov V, Bullara L, McCreery D B. Intraspinal stimulation for bladder voiding in cats before and after chronic spinal cord injury. J Neural Eng 4: 356-368, 2007). Voiding efficiencies induced by mechanical perigenital stimulation in these cats were very different (cat #1: 6.7±3.2%, cat #2: 43.2±7.7%, cat #3: 95.0±3.3%) with an average voiding efficiency of 48.3±25.6% in the 3 animals (30-32 tests per cat). This may be due to the fact that mechanical perigenital stimulation generated the smallest bladder pressure (38.8±2.5 cmH$_2$O) in cat #1, while it induced the largest bladder pressure (88.1±8.8 cmH$_2$O) in cat #3 (FIG. 16B). In cat #1 the bladder pressure induced by mechanical perigenital stimulation was significantly (P<0.05, unpaired t-test) smaller than the bladder pressure (64.7±4.8 cmH$_2$O) during the distention-induced micturition reflex (see FIG. 16B). It is also noteworthy that the efficiency of mechanical perigenital stimulation to induce voiding changed in the same animal over time (FIG. 16A).

Voiding induced by electrical stimulation was performed by first infusing the bladder to the capacity. After withdrawing the urethral catheter spontaneous voiding only occurred in one cat (cat #2) with a voiding efficiency ranging from 60% to 70% (2 tests). No spontaneous voiding was observed in the other 2 cats (cats #1 and #3). Repeated, short duration electrical perigenital stimulation (30 Hz, 30 V, 0.2 ms) was then tested to empty the bladder. The initial bladder volumes ranged from 21 ml to 116 ml. Voiding efficiency ranged from 30% to 100% with an average of 83.3±10.1% (N=3), that was not correlated with the initial volume or the voiding efficiency induced by mechanical perigenital stimulation in each cat. There was no significant difference (P<0.05) between the voiding efficiencies induced by mechanical or electrical perigenital stimulation.

7. Comparison Between Electrical and Mechanical Perigential Stimulation

Figure 16:
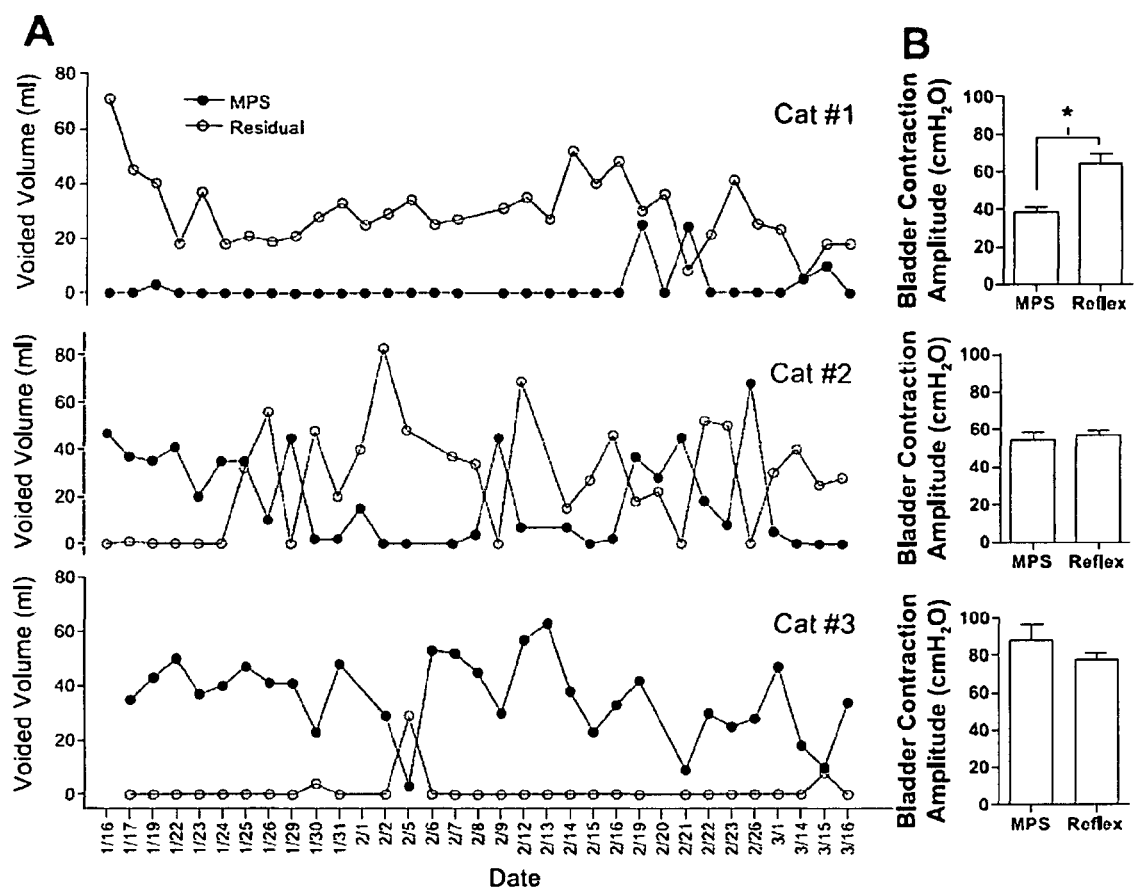
FIG. 16. A: comparison of voided volumes induced by MPS with the residual volumes following MPS during a 2-mo period in 3 cats. B: average bladder contraction pressure induced by MPS under isovolumetric conditions or by distention-induced micturition reflex (Reflex) is also shown for each cat.
Figure 17:
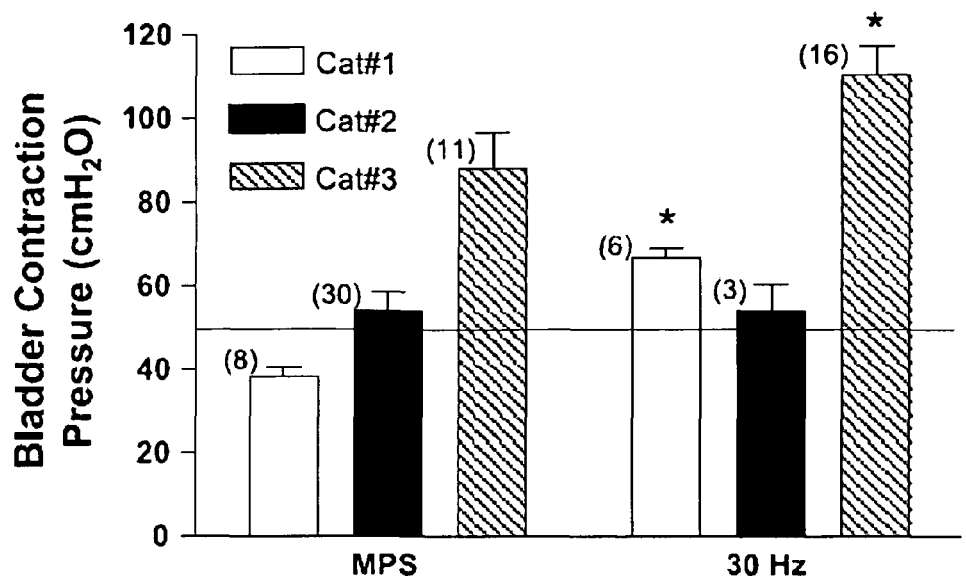
FIG. 17. Comparison of average bladder contraction pressure induced by MPS or 30-Hz electrical perigenital stimulation (20-30 V) in 3 cats under isovolumetric conditions when bladder volume was below micturition threshold. The thin line marks the bladder pressure of 50 cmH$_2$O. The numbers of tests are indicated in the parentheses. *Statistical significance (P<0.05).

Under isovolumetric conditions with bladder volume below the micturition threshold, electrical stimulation (30 Hz, 20-30 V) induced significantly larger bladder contractions (P<0.05, unpaired t-test) compared to those induced by mechanical stimulation in cats #1 and #3, but not in cat #2 (FIG. 17). Electrical stimulation produced post-stimulus voiding in all cats tested and generated isovolumetric bladder contraction pressures greater than 50 cmH$_2$O (FIG. 17). But the mechanical stimulation generated isovolumetric bladder contraction pressures less than 50 cmH$_2$O in cat #1 (FIG. 17) and often failed to induce post-stimulus voiding in this cat (FIG. 16A).

At the bladder volumes below micturition threshold the 30 Hz electrical stimulation induced isovolumetric bladder contractions that lasted 42.2±3.9 sec on average (FIG. 18A), but the mechanical stimulation could induce isovolumetric bladder contractions that were maintained for as long as the stimulation was continued (FIG. 18B). The maximal mechanical stimulation duration tested was about 3 minutes. At the bladder volumes above micturition threshold when large rhythmic bladder contractions were occurring, electrical stimulation at 7 Hz inhibited bladder (FIG. 18C), but mechanical stimulation slightly facilitated the bladder contractions evidenced by a longer contraction duration compared to the bladder activity prior to the stimulation (FIG. 18D). However, this facilitation was not observed during 30 Hz electrical stimulation (see FIG. 17A). Neither mechanical nor 30 Hz electrical stimuli significantly increased the amplitudes of the rhythmic bladder contractions (see FIG. 18D and FIG. 17A).

Discussion

Figure 14:
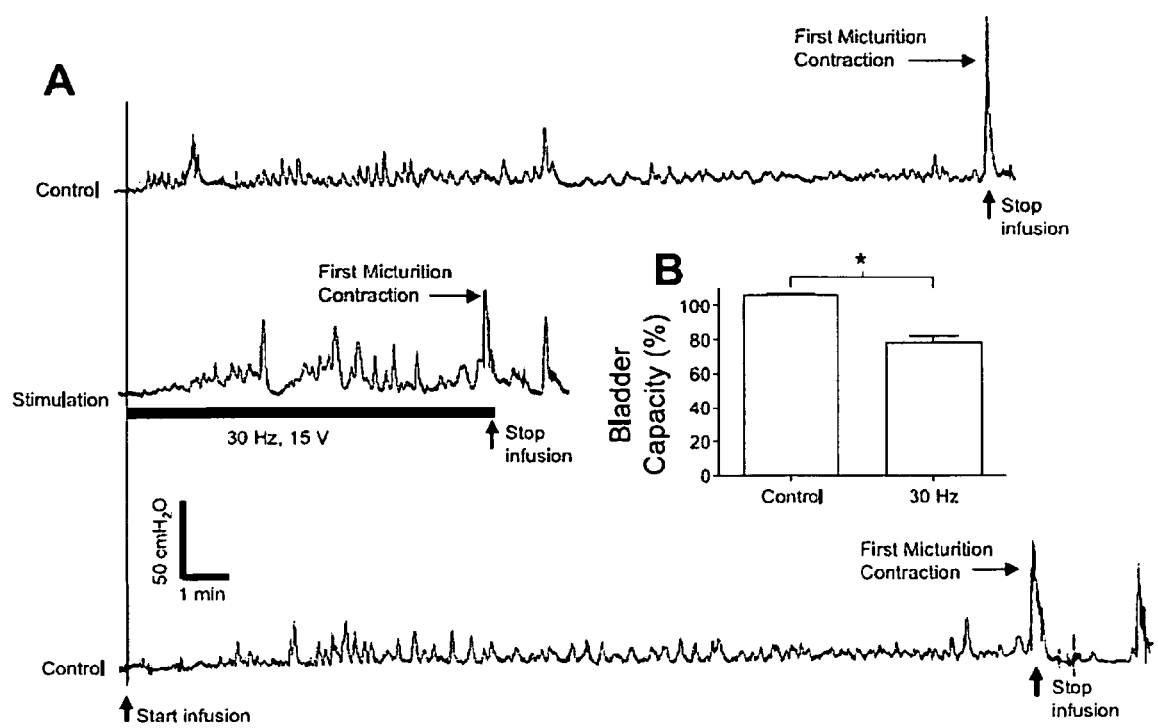
FIG. 14. Excitatory effect of electrical perigenital stimulation on bladder activity during CMGs. A: bladder pressure traces. The initial empty bladder was infused with saline at 2 ml/min. Control: no stimulation. Stimulation: 30 Hz, 15 V, 0.2-ms pulse width. The black bar under bladder pressure trace marks the stimulation duration. B: bladder capacity was significantly reduced by electrical perigenital stimulation at 30 Hz. Bladder capacity was normalized to the capacity measured in the first control CMG. Stimulation: 10-30 V; 0.2-ms pulse width. The calibration bars in A apply to all bladder pressure recordings. *Statistical significance (P<0.05); n=4.
Figure 15:
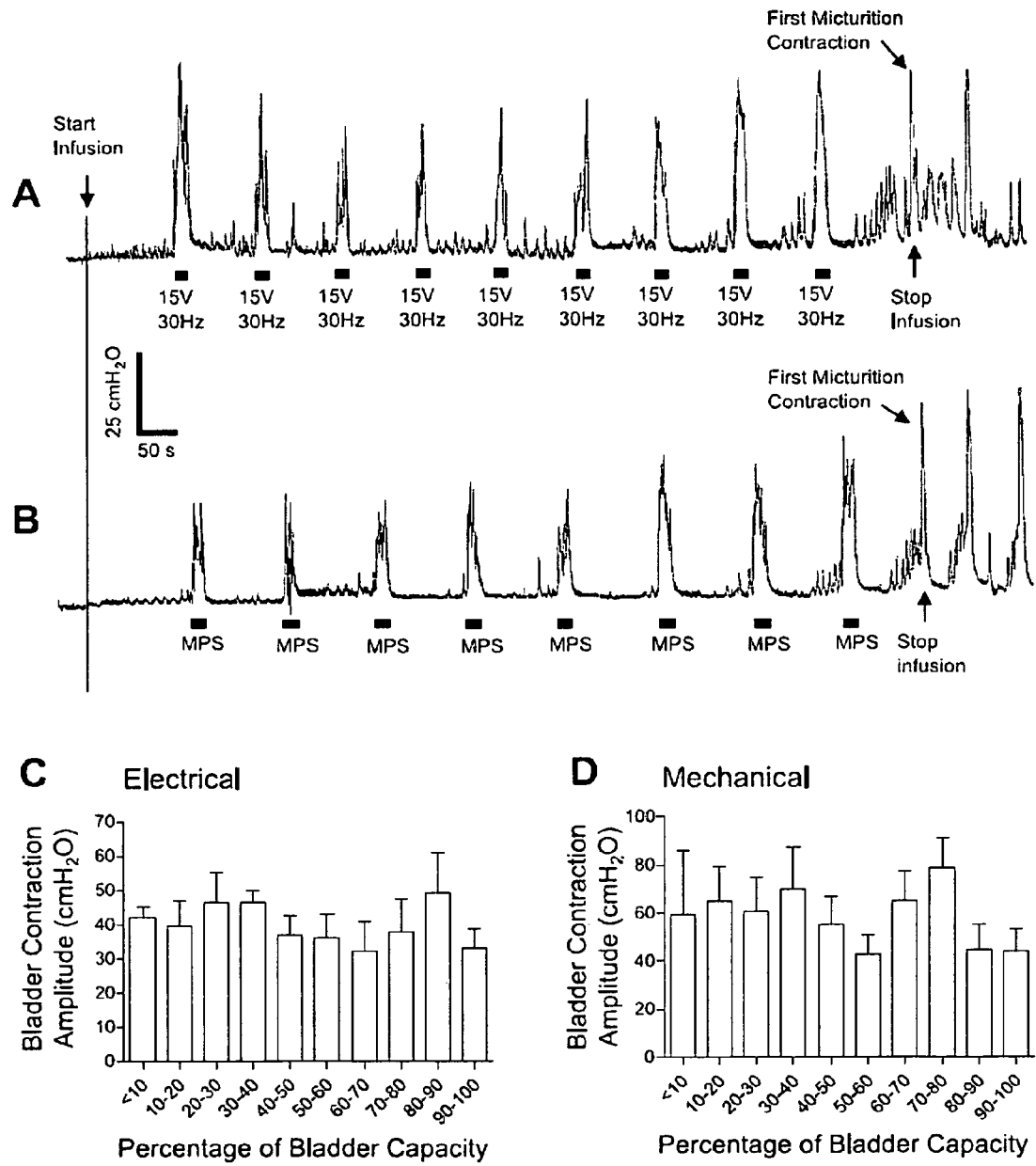
FIG. 15. Bladder contractions induced by electrical (A and C) or mechanical (B and D) perigenital stimulation during CMGs. Electrical stimulation: 30 Hz; 15 V in A, 11-30 V in C; 0.2-ms pulse width. Mechanical perigenital stimulation (MPS): repeatedly stroking (2-3 times/s) the perigenital skin with a cotton swab. The black bars under bladder pressure traces mark the stimulation duration. The calibration bars apply to bladder pressure recordings in both A and B. Saline infusion was started with the bladder empty. Infusion rate: 2 ml/min; n=3 for C and D.

This study revealed that in awake chronic SCI cats electrical stimulation of afferent nerves in the perigenital area could elicit either an inhibitory or an excitatory effect on the bladder depending on the frequency of stimulation. The inhibitory effect was maximal at a stimulation frequency of 5-7 Hz (FIG. 10 and FIG. 13), whereas the excitatory effect was maximal at 30 Hz (FIG. 12 and FIG. 14). Both the excitatory electrical perigenital stimulation (30 Hz) and the mechanical perigenital stimulation induced large bladder contractions that were not dependent on bladder volume (FIG. 15). Post-stimulus voiding was also induced by the two types of excitatory perigenital stimuli (FIG. 16). However, the properties of the perigenital-to-bladder reflex induced by electrical or mechanical stimulation were significantly different (see FIGS. 17 and 18) indicating that either different afferent pathways were activated or that the same afferent pathways were activated by these two stimuli in very different ways.

Figure 18:
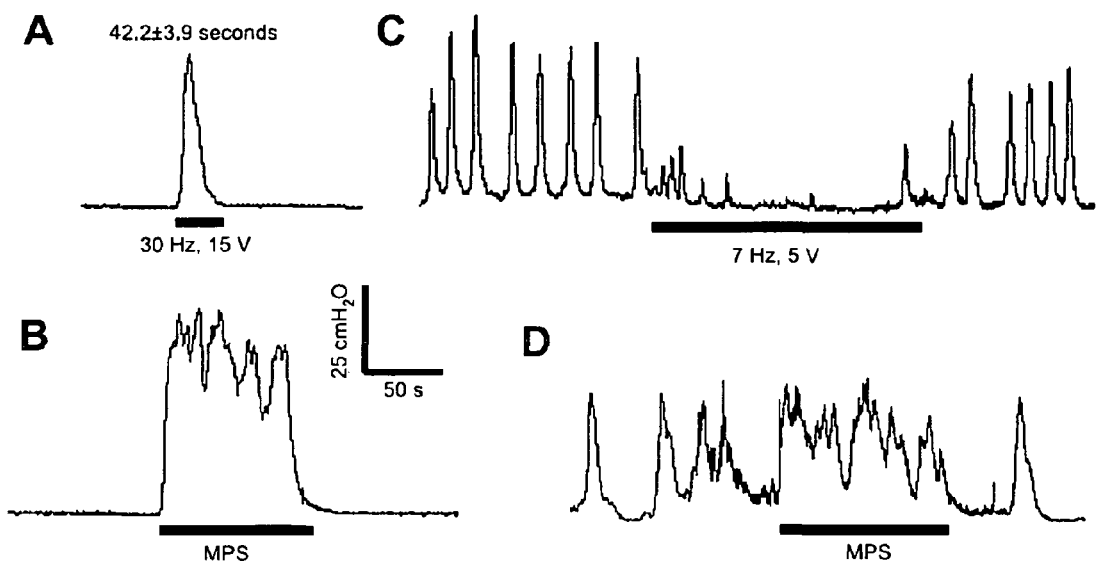
FIG. 18. Comparison of perigenital-to-bladder reflexes induced by electrical (A and C) or mechanical (B and D) perigenital stimulation under isovolumetric conditions. A and B: bladder volume was below micturition threshold. C and D: bladder volume was above micturition threshold and large rhythmic bladder contractions were occurring. The calibration bars in B apply to all bladder pressure recordings in A-D.

Mechanical stimulation only induced an excitatory effect on bladder, but electrical stimulation could induce either an excitatory or an inhibitory effect (see FIG. 18). The excitatory effect induced by mechanical stimulation lasted as long as the stimulation continued, but the electrical stimulation only induced short duration bladder contractions (FIG. 18A-B). These differences may be caused by the fact that afferent nerves are activated asynchronously by mechanical stimulation, but they are activated synchronously by each electrical pulse. The frequency of afferent firing can be selected by electrical stimulation, but mechanical stimulation may activate afferent nerves with a large range of firing frequencies. Electrical stimulation could activate both mechano- and non-mechano-sensitive afferent nerves from both skin and muscles, while mechanical stimulation mainly activates the mechano-sensitive afferent nerves from the skin.

Similar to the mechanical stimulation, the excitatory electrical stimulation also induced large amplitude bladder contractions at both low and high bladder volumes (see FIG. 15), indicating that the excitatory perigenital-to-bladder reflexes are independent of afferent input from the bladder. Electrical stimulation at 30 Hz probably activated the re-emerged, excitatory perigenital-to-bladder spinal reflex in chronic SCI cats, indicating that the average firing frequency of the afferent nerves activated by mechanical stimulation might be 30 Hz. A previous study (Kawatani M, Tanowitz M, de Groat W C. Morphological and electrophysiological analysis of the peripheral and central afferent pathways from the clitoris of the cat. Brain Res 646: 26-36, 1994) showed that light constant pressure on the clitoris of cat produced sustained afferent firing of pudendal nerve pathway with a maximal frequency of 40 Hz. In addition to directly activating the excitatory perigenital-to-bladder spinal reflex (FIG. 12 and FIG. 15A), the electrical stimulation could also facilitate the micturition reflex induced by bladder distension and reduce the micturition volume threshold during CMG (FIG. 14). The direct excitatory effect on the bladder lasted less than a minute (see FIG. 18A), but the facilitatory effect during CMGs could persist for many minutes (see FIG. 14). Thus, it is possible that the 30 Hz electrical stimulation induces both excitatory and inhibitory effects. The excitatory effect may be dominant initially but then suppressed by an inhibitory effect that turns off the perigenital-to-bladder reflex. However, the facilitatory effect on the micturition reflex pathway induced by bladder distension seems to be insensitive to the later inhibition. This suggests that different spinal interneuronal pathways or mechanisms may be involved in the direct excitatory perigenital-to-bladder reflex and the facilitatory effect on the bladder-to-bladder reflex.

At the same stimulation intensity, the electrical perigenital stimulation is inhibitory to the bladder at 5-7 Hz (FIG. 10), but becomes excitatory at 20-40 Hz (FIG. 12). This raises the possibility that the same population of afferent nerves can induce different responses at different frequencies or that different populations of afferent nerves with the same electrical threshold can produce inhibition and excitation. The frequency selection of perigenital-to-bladder spinal reflexes must occur in the spinal cord. One possible explanation is that the afferent firing at different frequencies triggers the release of different neurotransmitters at the first order synapses between the afferent neurons and the spinal interneurons resulting in either an inhibitory or an excitatory effect on the bladder activity. Another possible explanation is that the spinal interneuronal networks for bladder inhibition or excitation are optimally tuned at different frequencies. Afferent firing at 30 Hz is optimally transmitted through the excitatory spinal neural network, but 5-7 Hz is optimal for the inhibitory network (de Groat W C, Ryall R W. Reflexex to sacral parasympathetic neurons concerned with micturition in the cat. J Physiol 200: 87-108, 1969). The idea of frequency tuning of spinal neural networks involved in bladder function is also evidenced by previous studies in cats (de Groat W C. Nervous control of the urinary bladder of the cat. Brain Res 87: 201-211, 1975; de Groat W C, Lalley P M. Reflex firing in the lumbar sympathetic outflow to activation of vesical afferent fibers. J Physiol 226: 289-309, 1972; de Groat W C, Ryall R W. Recurrent inhibition in sacral parasympathetic pathways to the bladder. J Physiol 196: 579-591, 1968; Fall M, Lindstrom S. Electrical stimulation: A physiologic approach to the treatment of urinary incontinence. Urol Clin North Am 18: 393-407, 1991 and Lindstrom S, Fall M, Carlsson C A, Erlandson B E. The neurophysiological basis of bladder inhibition in response to intravaginal electrical stimulation. J Urol 129: 405-410, 1983). The maximal inhibition via the hypogastric nerve could be obtained when the pudendal afferent pathway was stimulated at 5 Hz, whereas the spinal inhibition via pelvic nerve could be optimally activated at frequencies 5-10 Hz (Fall M, Lindstrom S. Electrical stimulation: A physiologic approach to the treatment of urinary incontinence. Urol Clin North Am 18: 393-407, 1991 and Lindstrom S, Fall M, Carlsson C A, Erlandson B E. The neurophysiological basis of bladder inhibition in response to intravaginal electrical stimulation. J Urol 129: 405-410, 1983). Recurrent inhibition in sacral parasympathetic pathways to the bladder was optimally tuned at frequencies 15-40 Hz (de Groat W C. Mechanisms underlying recurrent inhibition in the sacral parasympathetic outflow to the urinary bladder. J Physiol 257: 503-513, 1976 and de Groat W C, Ryall R W. Recurrent inhibition in sacral parasympathetic pathways to the bladder. J Physiol 196: 579-591, 1968). And the pelvic-to-hypogastric reflex was maximally activated at the frequency of 0.5 Hz (de Groat W C, Lalley P M. Reflex firing in the lumbar sympathetic outflow to activation of vesical afferent fibers. J Physiol 226: 289-309, 1972).

Although both mechanical and electrical (30 Hz) stimulation induced large bladder contractions at a low bladder volume (FIG. 15), they failed to induce voiding during the stimulation in adult chronic SCI cats, probably due to a co-activation of the urethral sphincter—detrusor sphincter dyssynergia (DSD). However, a small amount of fluid release occurred at the end of each short period of stimulation (i.e. post-stimulus voiding, see also, Example 5, below) presumably due to the ability of the urethral sphincter striated muscle to relax faster than the smooth muscle of the bladder after the stimulation (Tai C, Smerin SE, de Groat W C, Roppolo J R. Pudendal-to-bladder reflex in chronic spinal-cord-injured cats. Exp Neurol 197: 225-234, 2006b). The post-stimulus voiding required a high bladder pressure (greater than 50 cmH$_2$O, see FIGS. 16 and 17). The higher the bladder pressure induced by mechanical stimulation, the higher the voiding efficiency that was produced (see FIG. 16). However, high pressure voiding is not clinically useful in patients with strong DSD because it could cause autonomic dysreflexia and kidney problems in long-term application (Consortium for Spinal Cord Medicine. Bladder management for adults with spinal cord injury: a clinical practice guideline for health-care providers. 2006 and Vaidyanathan S, Soni B M, Singh G, Oo T, Hughes P L, Mansour P. Flawed trail of micturition in cervical spinal cord injury patients: guidelines for trial of voiding in men with tetraplegia. Spinal Cord 41:667-672, 2003). In contrast, mechanical stimulation of the perigenital region is utilized by the mother cats to completely empty the bladder of neonatal kittens indicating that co-activation of the urethral sphincter is probably not induced in the neonates. Similar differences have also been noted in neonatal and SCI rats (Kruse M N, de Groat W C. Consequences of spinal cord injury during the neonatal period on micturition reflexes in the rat. Exp Neurol 125: 87-92, 1994).

As indicated, a series of short burst pulses can induce a small amount of urine release at the end of each short burst stimulation, that is, post-stimulus voiding. This method might be used in SCI patients who have strong DSD. However, this method requires cutting the sensory spinal roots, so that the DSD reflex can be eliminated in SCI patients. For SCI patients with strong DSD, perigenital or perianal stimulation might not be appropriate, requiring treatment with a 3-channel implantable device with 5-10 kHz bilateral pudendal nerve blockage.

The urological disorders in SCI patients are largely variable depending on the level of spinal cord injury, complete or incomplete, etc. Some SCI patients have only a detrusor hyperreflexia (DH, also called detrusor overactivity) during storage phase, but no DSD. Some have only DSD but no DH. The most devastating case is where SCI patients have both DH and DSD. The perigenital or perianal stimulation methods can be used to treat patients without DSD or with lesser DSD, where high bladder pressure will not be generated. The reason for generating high bladder pressure is not due to bladder contraction alone. It is due to bladder contacting against the closed urethra (such as in the case of DSD). As such, perigenital stimulation does not necessarily generate high pressure voiding.

Since the skin and muscles around the perigenital area are innervated by pudendal nerve, the afferent limb of the perigenital-to-bladder reflex is probably in the pudendal nerve. It has been suggested that stimulation of pudendal afferents could inhibit bladder activity via activation of hypogastric nerve when bladder volume was low, and via spinal inhibition of the parasympathetic efferent pathways to the bladder when bladder volume was high (Fall M, Erlandson B E, Carlsson C A, Lindstrom S. The effect of intravaginal electrical stimulation on the feline urethra and urinary bladder: neuronal mechanisms. Scand. J Urol Nephrol 44(suppl.): 19-30, 1978 and Fall M, Lindstrom S. Electrical stimulation: A physiologic approach to the treatment of urinary incontinence. Urol Clin North Am 18: 393-407, 1991). A previous study (Tai C, Smerin S E, de Groat W C, Roppolo J R. Pudendal-to-bladder reflex in chronic spinal-cord-injured cats. Exp Neurol 197: 225-234, 2006b) in anesthetized chronic SCI cats also showed the involvement of both hypogastric and pelvic efferent nerves in the inhibitory pudendal-to-bladder spinal reflex. The inhibitory perigenital-to-bladder reflex demonstrated in this study in awake chronic SCI cats might involve the same efferent pathways (hypogastric and pelvic) as revealed previously.

The efferent pathway in the excitatory perigenital-to-bladder reflex must involve the pelvic nerve. However, whether the facilitatory effect of perigenital afferent input on micturition reflex involves both pelvic and hypogastric nerves is still uncertain. Perigenital stimulation could either enhance the pelvic nerve efferent activity or suppress the hypogastric nerve efferent activity to facilitate the micturition reflex. Further studies are needed to identify the efferent pathways involved in the facilitation of micturition reflex induced by perigenital afferent activation.

Somato-Visceral Interactions

When the excitatory electrical (30 Hz) or mechanical perigenital stimulation (somatic) induced large amplitude (greater than 30 $cmH_2O$) bladder contractions at different bladder volumes (see FIG. 15), the stimulation also triggered bilateral hindlimb stepping movements. The stepping movements also occurred during the large amplitude (greater than 30 $cmH_2O$), long duration (greater than 20 seconds), distention-induced micturition reflexes, but not during the small PMCs (FIGS. 13 and 14), indicating that they were closely associated with the activation of the micturition reflex and that the stepping movements were not directly activated by pudendal afferent input independent of bladder activity. This idea is further supported by the fact that the excitatory 30 Hz electrical perigenital stimulation did not induce the hindlimb movements during CMGs until a micturition reflex occurred (see FIG. 14). The hinblimb stepping movement was a useful marker to indicate the occurrence of a micturition reflex in awake chronic SCI cats (Tai C, Miscik C L, Ungerer T D, Roppolo J R, de Groat W C. Suppression of bladder reflex activity in chronic spinal cord injured cats by activation of serotonin 5-$HT_{1A}$ receptors. Exp Neurol 199: 427-437, 2006a and Thor K B, Roppolo J R, de Groat W C. Naloxone induced micturition in unanesthetized paraplegic cats. J Urol 129: 202-205, 1983). This observation also indicates that a full bladder may be one of the mechanisms that triggers the occurrence of leg spasticity in SCI humans.

The perigenital-to-bladder reflex induced by mechanical stimulation exhibited significant plasticity after SCI (Table 1). The excitatory perigenital-to-bladder reflex, which exists in neonatal kittens, disappears during development and is replaced by an inhibitory perigenital-to-bladder reflex in adult cats. After SCI the mechanical stimulation-induced, excitatory perigenital-to-bladder reflex re-emerges (see FIGS. 15-18) and the inhibitory reflex disappears (de Groat W C. Nervous control of the urinary bladder of the cat. Brain Res 87: 201-211, 1975; de Groat W C, Araki I, Vizzard M A, Yoshiyama M, Yoshimura N, Sugaya K, Tai C, Roppolo J R. Developmental and injury induced plasticity in the micturition reflex pathway. Behavioural Brain Res. 92: 127-140, 1998; de Groat W C, Ryall R W. Recurrent inhibition in sacral parasympathetic pathways to the bladder. J Physiol 196: 579-591, 1968; and Kirkham A P S, Shah N C, Knight S L, Shah P J R, Craggs M D. The acute effects of continuous and conditional neuromodulation on the bladder in spinal cord injury. Spinal Cord 39: 420-428, 2001). This reflex plasticity indicates a significant re-organization occurring in the spinal cord after chronic SCI.

The effect of electrical perigenital stimulation on bladder reflexes in awake spinal intact cats has not been determined, making it impossible to evaluate the plasticity of this reflex after chronic SCI. However, in anesthetized spinal-intact cats intra-vaginal electrical stimulation at a frequency of 5-10 Hz inhibited bladder activity (Fall M, Erlandson B E, Carlsson C A, Lindstrom S. The effect of intravaginal electrical stimulation on the feline urethra and urinary bladder: neuronal mechanisms. Scand J Urol Nephrol 44: 19-30, 1978 and Lindstrom S, Fall M, Carlsson C A, Erlandson B E. The neurophysiological basis of bladder inhibition in response to intravaginal electrical stimulation. J Urol 129: 405-410, 1983). Furthermore, dorsal penile/clitoris nerve stimulation at 10 Hz also inhibited both Aδ-fiber mediated Jiang C H, Lindstrom S. Prolonged enhancement of the micturition reflex in the cat by repetitive stimulation of bladder afferents. J Physiol 517:599-605, 1999) and C-fiber mediated (Mazieres L, Jiang C H, Lindstrom S. The C fibre reflex of the cat urinary bladder. J Physiol 513: 531-541, 1998) pelvic-to-pelvic micturition reflexes in spinal intact cats, indicating that electrical stimulation of the perigenital skin area at these frequencies might be also inhibitory (see Table 1). An excitatory effect of electrical perigenital stimulation on bladder activity in spinal intact cats might also occur since pudendal nerve stimulation in a range of frequencies (1-40 Hz) induced bladder contractions (Boggs J W, Wenzel B J, Gustafson K J, Grill W M. Spinal micturition reflex mediated by afferents in the deep perineal nerve. J Neurophysiol 93: 2688-2697, 2005; Boggs J W, Wenzel B J, Gustafson K J, Grill W M. Frequency-dependent selection of reflexes by pudendal afferents in the cat. J Physiol 577: 115-126, 2006; de Groat W C, Ryall R W. Reflex to sacral parasympathetic neurons concerned with micturition in the cat. J Physiol 200: 87-108, 1969; Mazieres L, Jiang C, Lindstrom S. Bladder parasympathetic response to electrical stimulation of urethral afferents in the cat. Neurourol Urodynam 16: 471-472, 1997; and Shefchyk S J, Buss R R. Urethral pudendal afferent-evoked bladder and sphincter reflexes in decerebrate and acute spinal cats. Neurosci Lett 244:137-140, 1998) (see Table 1). The perigenital-to-bladder reflex induced by electrical stimulation in spinal intact cats needs to be further investigated in order to fully understand the neuroplasticity of this reflex after SCI.

TABLE 1

Comparison of perigenital-to-bladder reflexes induced by mechanical and electrical stimulation in spinal intact and chronic SCI cats

| | Mechanical stimulation | | Electrical Stimulation | |
|---|---|---|---|---|
| | Spinal Intact | Chronic SCI | Spinal Intact | Chronic SCI |
| Inhibition | Yes | No | Yes (5-10 Hz)* | Yes (5-7 Hz) |
| Excitation | No | Yes | Yes (1-40 Hz)** | Yes (20-40 Hz) |

SCI = Spinal Cord Injured;
*Intravaginal stimulation;
**pudendal nerve stimulation Our current study in awake chronic SCI animals tested the hypothesis that frequency dependent activation of the inhibitory or excitatory pudendal-to-bladder spinal reflex could be achieved by applying electrical stimulation to the perigenital skin area. A previous study (Walter J S, Wheeler, J S, Robinson C J, Wurster R D. Inhibiting the hyperreflexic bladder with electrical stimulation in a spinal animal model. Neurourol Urodynam 12: 241-253, 1993) using restrained, awake, chronic SCI cats only investigated the inhibitory effect on the bladder by inserting fine wire electrodes percutaneously to stimulate the pudendal nerve. Bladder excitation by perineal stimulation was also investigated previously in spinal dogs (Walter J S, Wheeler J S, Robinson C J, Wurster R D. Surface stimulation techniques for bladder management in the spinal dog. J Urol 141:161-165, 1989). Our study further showed that both inhibitory and excitatory bladder responses could be induced in chronic SCI cats by electrical perigenital stimulation at different frequencies. Clinical tests using suprapubic tapping and jabbing could only induce bladder contractions in about 50% of the SCI subjects (Cardenas D D, Kelly E, Mayo M E. Manual stimulation of reflex voiding after spinal cord injury. Arch Phys Med Rehabil 66:459-462, 1985) and manual anorectal stimulation inhibited bladder activity (Rodriquez A A, Awad E. Detrusor muscle and sphincter response to anorectal stimulation in spinal cord injury. Arch Phys Med Rehabil 60:269-272, 1979). But these clinical tests activated very different afferent pathways than perigenital stimulation. Currently, a systematic clinical investigation of the frequency dependent bladder responses to perigenital electrical stimulation in SCI subjects is still not available. Although a recent study in chronic SCI cats (Example 5) showed that intraspinal microstimulation might be applicable to restore bladder function after SCI, a non-invasive clinical approach to either excite or inhibit the bladder activity will still be very useful and could be envisioned based on the results presented in our study.

Example 3

Bladder Inhibition or Excitation by Electrical Perianal Stimulation in the Chronic SCI Cat Example 2 demonstrates that electrical perigenital stimulation could activate a branch of the pudendal nerve to induce either an inhibitory or an excitatory spinal reflex to the bladder at different stimulation frequencies. Since the pudendal nerve also innervates the muscle and skin in the perianal area, we explored in this study if electrical stimulation applied on the perianal skin area could also activate either an inhibitory or an excitatory spinal reflex to the bladder depending on stimulation frequency.

Electrical stimulation applied by ring electrodes located on anal plug can induce contraction of the pelvic floor muscles and inhibition of detrusor overactivity (Godec C, Cass A S, Ayala G F. Bladder inhibition with functional electrical stimulation. Urology 1975: 6:663-666). This technique has been recommended for stress and urge urinary incontinence (Godec C, Cass A S, Ayala G F. Electrical stimulation for incontinence; technique, selection and results. Urology 1976: 7:388-397). However, intra-anal stimulation produced some problems. For example, the anal plug electrodes had to be removed every 2-3 h to pass flatus. In addition, many patients could not use these electrodes because of pain and discomfort or because of a stenotic or closed anus due to previous injury or surgery. In order to provide a solution for these problems, the effect of electrical stimulation of the perianal skin on bladder function was investigated (Nakamura M, Sakurai T, Tsujimoto Y, Tada Y. Bladder inhibition by electrical stimulation of the perianal skin. Urol. Int. 1986: 41:62-63). It was found that perianal electrical stimulation elicited a suppression of detrusor activity and caused poststimulation improvement in frequency, urgency, and incontinence. In this study we further characterized the spinal reflexes from the perianal skin area to the bladder using awake chronic SCI cats.

Methods

Spinal Cord Transection

Three female cats (2.8-3.4 kg) were spinalized under isoflurane anesthesia using aseptic surgical techniques. After performing a dorsal laminectomy at T9-T10 vertebral level, a local anesthetic (lidocaine 1%) was applied to the surface of the spinal cord and then injected into the cord through the dura. The spinal cord was then cut completely, and a piece of gel foam was placed between the cut ends (usually a separation of 2-3 mm). The muscle and skin were then sutured. After full recovery from anesthesia the animal was returned to its cage. Following spinal transection, the bladder was emptied daily by manual expression. If manual expression was not successful, a sterile catheter (3.5 F) was inserted through the urethra to empty the bladder. Ketaprofen (2 mg/kg twice a day for 3 days) and antibiotics (Clavamox, 15-20 mg/kg for 7 days) were given following surgery. Experiments to determine the properties of perianal-to-bladder spinal reflex were conducted after at least 4-5 weeks following spinal cord transaction.

Experimental Setup

A sterile double lumen balloon catheter (7 F) was inserted through the urethra into the bladder of the chronic SCI cats without anesthesia. The balloon was distended by 2 ml of air and then positioned at the bladder neck by gently pulling the catheter back. The balloon prevented leakage of the fluid from the bladder. One lumen of the catheter was connected to a pump to infuse the bladder with sterile saline at a rate of 2 ml/min, and the other lumen was connected to a pressure transducer to measure the pressure change in the bladder. A pair of sterilized hook electrodes (made from 23G needles) was attached to the skin (about 1 mm penetration into the skin with 2-4 mm contact) on the left and right sides of the anus approximately 1-1.5 cm from the anal opening. Due to the complete spinal transection, the animals did not sense either bladder catheterization or electrical stimulation. During the experiment (usually 4-5 hours) the animals rested comfortably in a padded animal transport carrier. Since the animal was free to move in the carrier, bladder pressure recordings that were disrupted by the animal's movements were discarded. At the end of the experiment the catheter was withdrawn and the electrodes were detached. After each experiment the animal was given 150 mg/kg of ampicillin subcutaneously. Multiple experiments were repeated on the same animal on different days.

Stimulation Protocol

Uniphasic pulses (0.2 ms pulse width) of different intensities (1-30 V) and frequencies (0.5-50 Hz) were delivered to the perianal skin area via the attached electrodes using a stimulator (Grass Medical Instruments, S88) with a stimulus isolator (Grass Medical Instruments, SIU5).

In the first group of experiments, the bladder was infused to one of the two different volumes: (1) a volume slightly above the micturition threshold to induce large amplitude (greater than 25 cm $H_2O$) rhythmic bladder contractions (see FIG. 19A); or (2) a volume slightly below the micturition threshold so that no large amplitude rhythmic bladder contractions occurred (see FIG. 21A). During rhythmic bladder contractions, electrical perianal stimulation was applied in order to determine the effective stimulation parameters to inhibit the bladder. The stimulation duration was longer than the period of at least 2 rhythmic bladder contractions in order to confirm the inhibitory effect. The effective stimulation parameters to induce bladder contractions were determined when bladder volume was low and large amplitude rhythmic contractions were absent. Stimulation duration of 30-50 seconds was used so that a full bladder contraction response could be induced which included the peak of the contraction and the gradual return of bladder pressure to the baseline.

In the second group of experiments, the most effective stimulation parameters to inhibit the bladder (7 Hz) identified in the first group of experiments were further tested during a slow infusion of the bladder (i.e., during a cystometrogram-CMG, see FIG. 22A). The CMG was always performed with an initially empty bladder. First, control CMGs were repeated 2-3 times without stimulation to obtain the control values and evaluate the reproducibility. Then, inhibitory perianal stimulation was applied during the CMG to quantify the inhibitory effect by measuring the change in bladder volume to induce the first large amplitude reflex contraction (i.e., bladder capacity). Stimulation and infusion were stopped when the first micturition contraction occurred which was defined as the first large amplitude (greater than 25 cm $H_2O$), long duration (greater than 20 sec) reflex bladder contraction that was accompanied by hindlimb stepping movements. Previous studies showed that hindlimb stepping movement was a useful marker for the occurrence of a micturition reflex in awake chronic SCI cats. Bladder capacity is defined as the bladder volume threshold during a CMG which evokes the first micturition contraction. The bladder was emptied after each CMG and a 5-10 minute waiting period was allowed between CMGs for the bladder reflexes to recover.

In the third group of experiments, the ability of the excitatory electrical stimulation (30 Hz) to induce bladder contractions at different bladder volumes was further evaluated. A short burst (30-50 sec) of stimulus pulses was applied during a CMG after infusion of saline in 4-8 ml increments.

Data Analysis

For the rhythmic bladder activity, the area under bladder pressure curve, the inter-contraction interval (ICI), and the average bladder contraction amplitude were measured during the electrical stimulation and were normalized to the measurements during the same time period prior to the stimulation. The contraction frequency is represented as 1/ICI because ICI is an infinite value when complete bladder inhibition occurs. For the bladder contractions induced by electrical stimulation at a bladder volume below capacity, the areas under the induced bladder pressure curves were measured and normalized to the maximal measurement during each experimental trial. During CMGs small amplitude (10-25 cm $H_2O$), short duration (less than 20 sec) pre-micturition contractions (PMCs) occurred prior to the large amplitude micturition contraction in chronic SCI cats. PMCs indicate the bladder overactivity due to chronic SCI that plays a role in frequent incontinence after SCI. For the CMG recordings, the bladder capacity, the volume threshold to induce the first PMC, the amplitude and the number of PMCs per minute were measured and normalized to the measurements during the first control CMG. For the bladder contractions induced by electrical perianal stimulation at different bladder volumes during a CMG the amplitude of the contractions were measured. The tested bladder volumes were normalized to the bladder capacity, and then they were grouped in bins with every 10% increase of the bladder volume. The normalized data from different experiments are presented as mean±SEM. Both one sample Student t-test and paired Student t-test were used to detect statistical significance (P<0.05). Linear regression analysis (95% confidence interval) and ANOVA analysis were used to determine whether the amplitude of bladder contractions induced by perianal stimulation was increased as the bladder volume increased.

Results

Inhibitory Perianal-to-Bladder Spinal Reflex

Figure 19A:
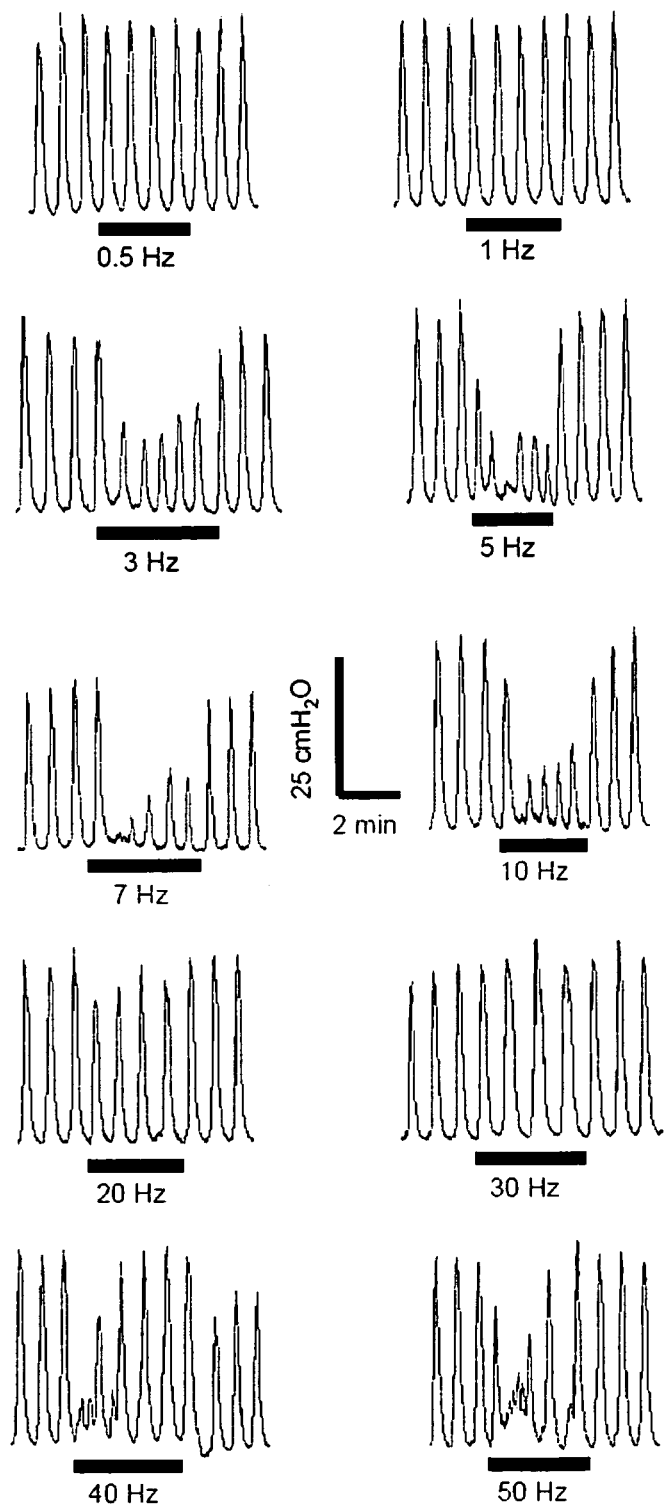
FIG. 19. Frequency dependent inhibition of rhythmic bladder activity induced by electrical perianal stimulation under isovolumetric conditions. A. Effect on bladder pressure recordings at different stimulation frequencies. The black bars under bladder pressure recordings mark the stimulation duration. B. Area under bladder pressure curve during stimulation. C. Average bladder contraction amplitude during stimulation. D. The inverse of inter-contraction interval (1/ICI) during stimulation. Bladder responses during stimulation were normalized to the responses before stimulation in B-D. Stimulation: 30 V in A, but 8-30 V in B-D; 0.2 ms pulse width. *indicates statistical significance (P<0.05). N=6 (2 tests on each cat).
Figure 19B:
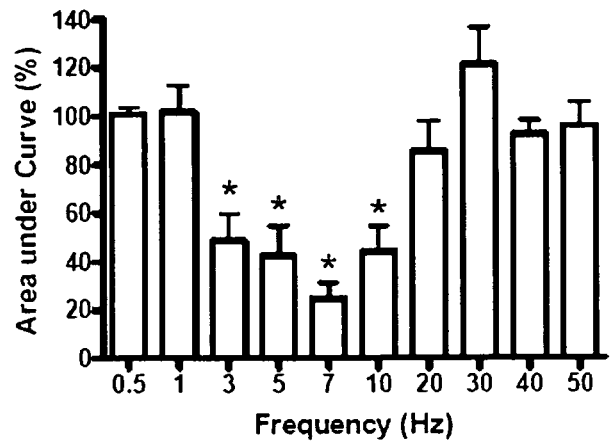
Figure 19C:
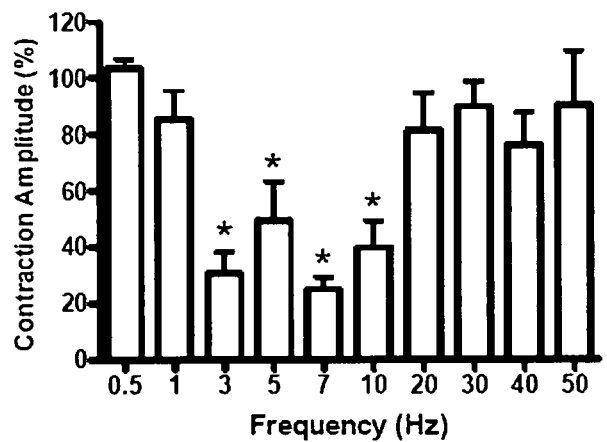

The inhibitory effect of electrical perianal stimulation on rhythmic bladder activity in awake chronic SCI cats was dependent on stimulation frequency. FIG. 19A shows an example of electrical perianal stimulation at different frequencies (0.5-50 Hz) inhibiting rhythmic bladder contractions. The different stimulation frequencies were applied in a random order, but they are shown in ascending order in FIG. 19A for clarity. The inhibitory effect on rhythmic bladder activity was obvious (P<0.05) between 3 Hz and 10 Hz as either a decrease in the contraction amplitude or a reduction in the area under bladder pressure curve (FIGS. 19A and 19B). The stimulation significantly (P<0.05) decreased the average contraction amplitude during the stimulation at 3-10 Hz (FIG.

Figure 19D:
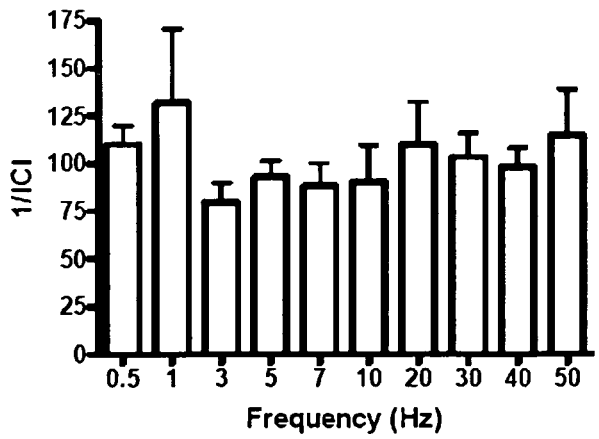

19C), but the frequency of bladder rhythmic contractions was not changed significantly (P>0.05, FIG. 19D).

Figure 20A:
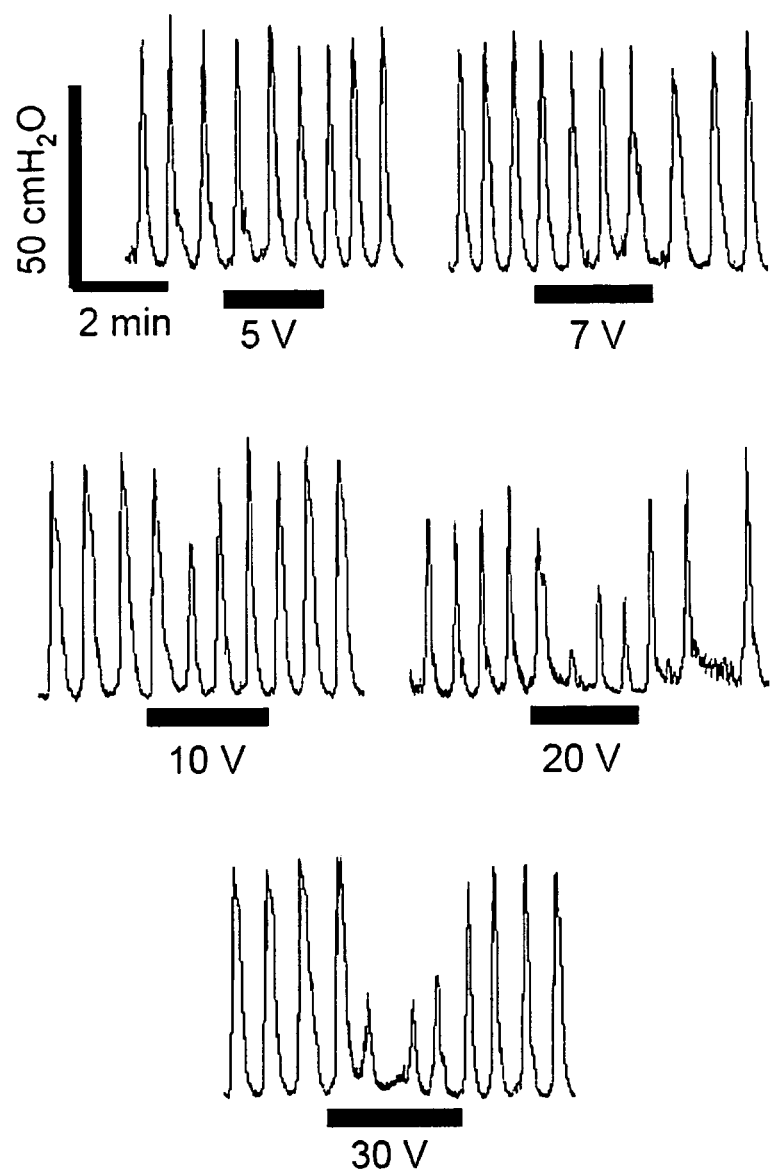
FIG. 20. Intensity dependent inhibition of rhythmic bladder activity induced by electrical perianal stimulation under isovolumetric conditions. A. Effect on bladder pressure recordings at different intensities. The black bars under bladder pressure recordings mark the stimulation duration. B. Area under bladder pressure curve. C. Average bladder contraction amplitude. D. The inverse of intercontraction interval (1/ICI). Bladder responses during stimulation were normalized to the responses before stimulation in B-D. Stimulation: 7 Hz; 0.2 ms pulse width. *indicates statistical significance (P<0.05). N=6 (2 tests on each cat).
Figure 20B:
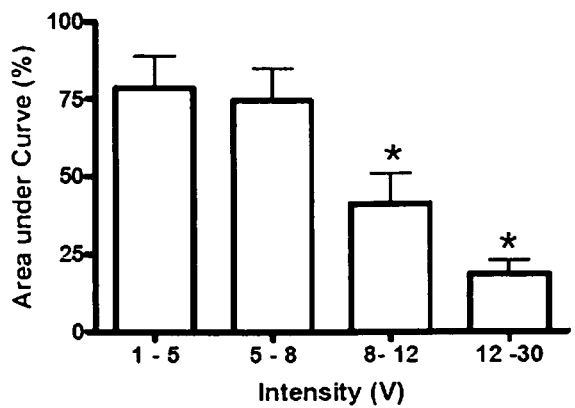
Figure 20C:
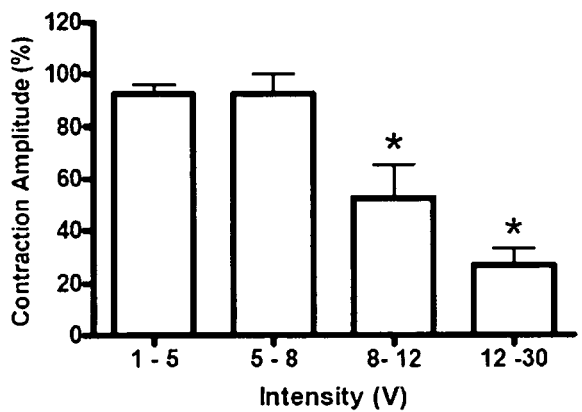
Figure 20D:
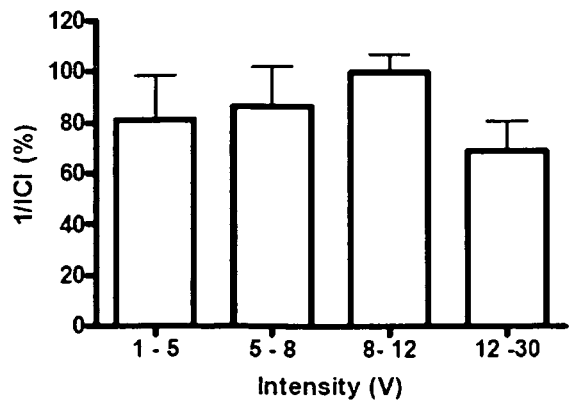

The inhibitory effect on rhythmic bladder activity was also dependent on stimulation intensity. FIG. 20A shows an example of inhibition of rhythmic bladder contractions at different intensities (5-30 V) using a frequency of 7 Hz. The different stimulation intensities were applied in a random order, but they are shown in ascending order in FIG. 20A for clarity. At stimulation intensity above 8 V, the electrical perianal stimulation significantly (P<0.05) reduced the area under the bladder contraction curve during the stimulation compared to the bladder activity prior to the stimulation (FIG. 20B). The stimulation also significantly (P<0.05) decreased the average contraction amplitude during the stimulation at an intensity above 8 V (FIG. 20C), but the frequency of bladder contractions was not changed significantly (P>0.05, FIG. 20D).

2. Excitatory Perianal-to-Bladder Spinal Reflex

Figure 21A:
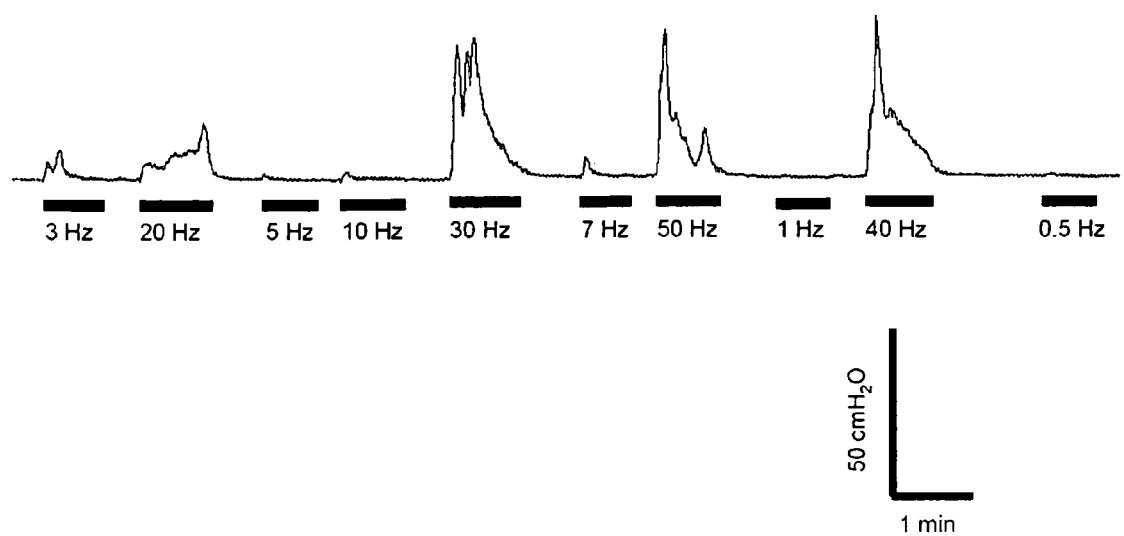
FIG. 21. Bladder contraction induced by electrical perianal stimulation at different frequencies (A) or at different intensities (B). The area under bladder pressure curve is dependent on both stimulation frequency (C) and intensity (D). Stimulation: 15 V in A, but 10-30 V in C; 30 Hz in B and D; 0.2 ms pulse width. The black bars under bladder pressure traces mark the stimulation duration. The responses were normalized to the maximal response during each trial in C-D. *indicates statistical significance (P<0.05). N=6 (2 tests on each cat). Data in A and B are from different animals.
Figure 21B:
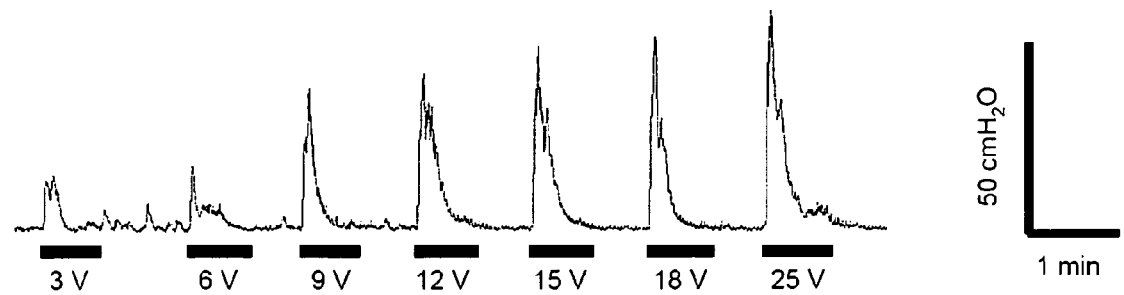
Figure 21C:
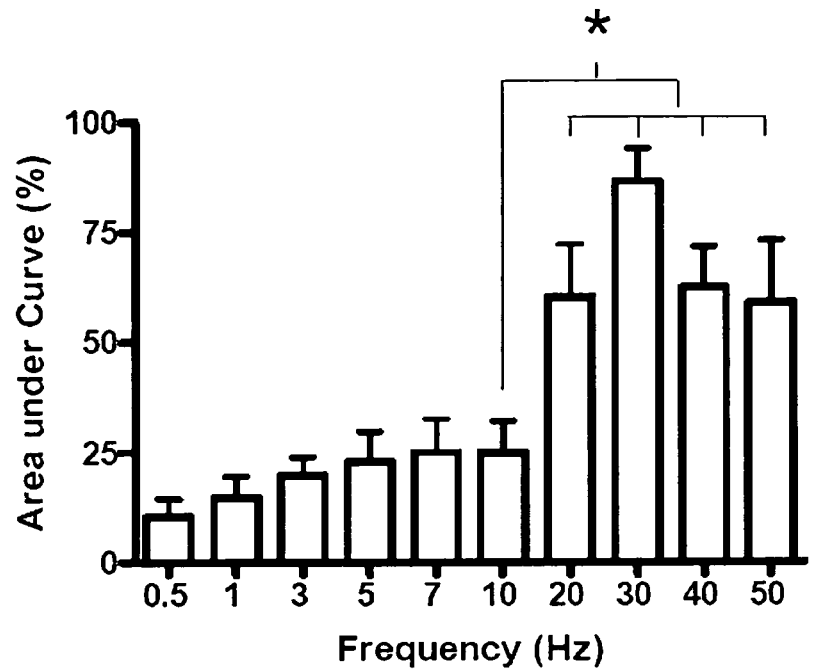
Figure 21D:
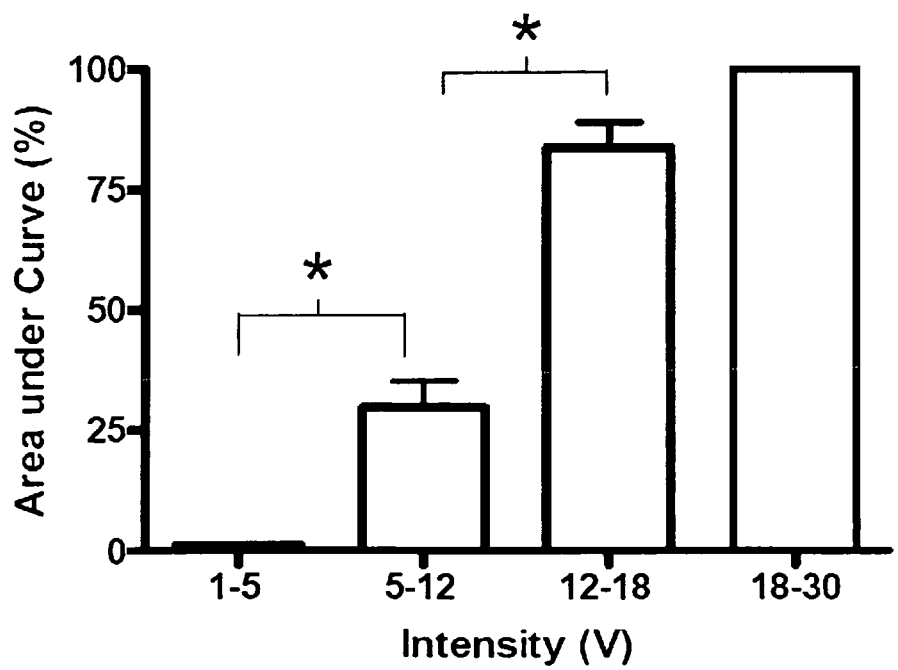

The perianal-to-bladder reflex in awake chronic SCI cats could also be excitatory depending on the electrical stimulation frequency and intensity. FIGS. 21A-B shows examples of bladder contractions induced by electrical perianal stimulation at different frequencies and intensities when bladder volume was below its capacity. Large amplitude (greater than 25 cm $H_2O$), long duration (greater than 20 sec) bladder contractions were induced by stimulation at a frequency between 20 Hz and 50 Hz (FIG. 21A). This excitatory effect was enhanced as the stimulation intensity increased (FIG. 21B). Electrical stimulation at 30 Hz was optimal to induce bladder contractions since it produced the largest area under the bladder contraction curve. The effect of 30 Hz was significantly (P<0.05) larger than the responses produced at a frequency of 10 Hz (see FIG. 21C). In order for 30 Hz stimulation to induce a large bladder contraction greater than 75% of the maximal response, the required stimulation intensity was above 12 V (FIG. 21D).

3. Micturition Volume Threshold Modulated by Perianal Stimulation

The threshold bladder volume (i.e., bladder capacity) to induce a micturition reflex contraction in awake chronic SCI cats was significantly increased by the inhibitory electrical perianal stimulation at 7 Hz. FIG. 22A shows an example of repeated CMG recordings. Compared to the first control CMG, the 7 Hz stimulation delayed the occurrence of both the first micturition contraction and the first pre-micturition contraction (PMC) (FIG. 19A). The bladder capacity was significantly (P<0.05) increased to 140±10% of the control capacity (FIG. 22B) and the volume threshold to induce the first PMC was significantly (P<0.05) increased to 255±60% of the control value (FIG. 22C). The average amplitude and the frequency of the PMCs were also significantly (P<0.05) decreased to 56±3% and 41±5% of the control value (FIG. 22D-E). The amplitude of the first micturition contraction was not influenced by the inhibitory 7 Hz stimulation (see FIG. 22A).

Figure 23A:
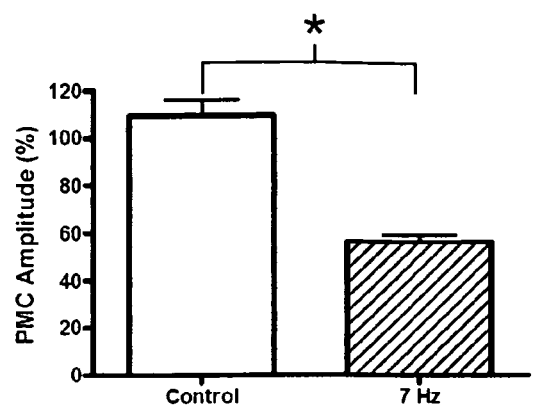
FIG. 23. Bladder contractions induced by electrical perianal stimulation during cystometrogram (CMG). Electrical stimulation: 30 Hz; 25 V in A, but 11-30 V in B; 0.2 ms pulse width. The black bars under bladder pressure traces mark the stimulation duration. Saline infusion was started with the bladder empty. Infusion rate: 4 ml/min. N=6 (2 tests on each cat).
Figure 23A:
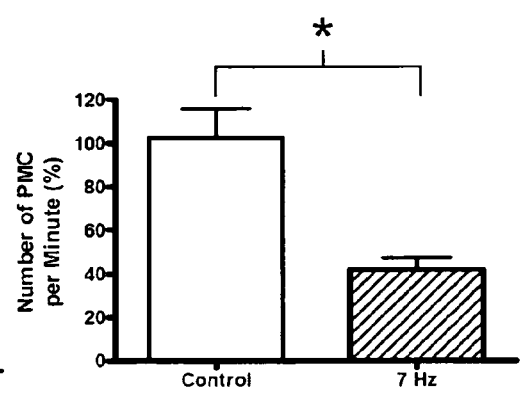
Figure 23A:
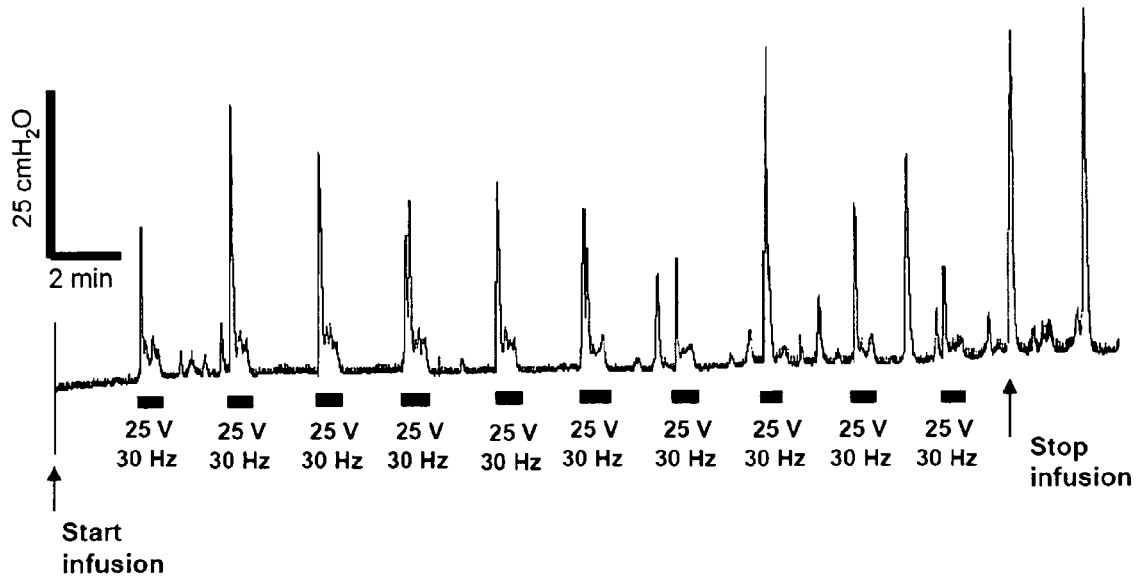
Figure 23B:
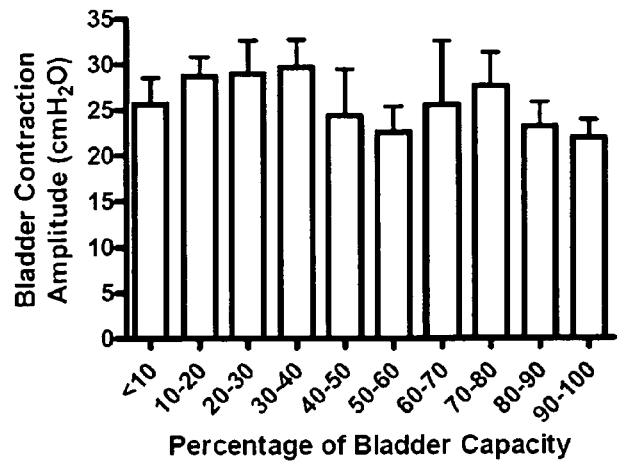

4. Independence of Excitatory Perianal-to-Bladder Spinal Reflex on Bladder Volume In addition to inhibiting the bladder-to-bladder micturition reflex, the perianal afferent input could also induce an excitatory perianal-to-bladder reflex in awake chronic SCI cats, which was not dependent on the bladder volume. FIG. 23A shows a CMG recording where a short burst (40 second duration) of electrical stimulation (25 V, 30 Hz) was repeatedly applied to the perianal area at regular intervals following approximately 4 ml increments in bladder volume. The stimulation induced large (greater than 25 cm $H_2O$) amplitude bladder contractions at a variety of bladder volumes. FIG. 23B shows the average amplitude of bladder contractions induced by electrical (30 Hz) stimulation at different bladder volumes. Both ANOVA analysis and linear regression analysis showed that the amplitude of bladder contractions was not significantly (P>0.05) increased when the bladder volume was increased (FIG. 23B).

Discussion

This study revealed that in awake chronic SCI cats, electrical stimulation of afferent nerves located in the perianal skin area could elicit either an inhibitory or an excitatory spinal reflex to the bladder depending on the frequency of stimulation. The inhibitory effect was significant at a stimulation frequency of 3-10 Hz (FIG. 19), but the excitatory effect was maximal at 30 Hz (FIG. 21C). The inhibitory stimulation at 7 Hz significantly increased bladder capacity and inhibited the pre-micturition contractions (FIG. 22). The excitatory electrical (30 Hz) perianal stimulation induced large bladder contractions that were not dependent on bladder volume (FIG. 23). The results obtained in this study are similar to those obtained from electrical stimulation of perigenital area, described in Example 2, indicating that the pudendal afferents from both anal and genital areas could have the same modulatory role on bladder activity in chronic SCI cats.

Mechanical anal stimulation could also induce either an inhibitory or an excitatory effect on bladder activity. Inhibition of bladder contractions by stretching the anal sphincter was observed in people with or without SCI (Kock N G, Pompeius R. Inhibition of vesical motor activity induced by anal stimulation. Acta Chir Scand 1963: 126:244-250 and Rodriquez A A, Awad E. Detrusor muscle and sphincteric response to anorectal stimulation in spinal cord injury. Arch. Phys. Med. Rehabil. 1979: 60:269-272). Excitation of the bladder was also seen in SCI subjects by light perianal touch, pinprick, introduction of rectal catheter, or alternatively inflation and deflation of a rectal balloon (Rossier A, Bors E. Detrusor responses to perianal and rectal stimulation in patients with spinal cord injuries. Urol. Int. 1964: 18:181-190). It seems that mild stretch or light touch of the anus tends to be excitatory while vigorous stretch tends to cause inhibition. In this study, we further demonstrated that the perianal-to-bladder spinal reflex in awake chronic SCI cats could be either inhibitory or excitatory depending on the frequency of electrical stimulation. Previous studies (Godec C, et al., Urology 1975: 6:663-666; Godec C, et al., Urology 1976: 7:388-397; and Nakamura M, et al., Urol. Int. 1986: 41:62-63) in human SCI subjects using electrical stimulation (20 Hz) of the anal area only demonstrated bladder inhibition. Our study indicated that using perianal stimulation at different frequencies might also induce bladder excitation in people with SCI. Inducing either inhibition or excitation using the same stimulation electrode will be very useful in clinical applications.

Since the skin and muscle around the anal area are innervated by pudendal nerve, the electrical stimulation used in this study must have activated a branch or branches of this nerve. The inhibitory pudendal-to-bladder reflex has been demonstrated in spinal intact and acute SCI cats by intravaginal electrical stimulation. It was suggested that stimulation of pudendal afferents could inhibit bladder activity via activation of hypogastric nerve when bladder volume was low, and via spinal inhibition of parasympathetic activity in the pelvic nerve when bladder volume was high (Fall M, Erlandson B E, Carlsson C A, Lindstrom S. The effect of intravaginal electrical stimulation on the feline urethra and urinary bladder: neuronal mechanisms. Scand. J. Urol. Nephrol. suppl. 1978: 44:19-30 and Fall M, Lindstrom S. Electrical stimulation: A physiologic approach to the treatment of urinary incontinence. Urol. Clin. North Amer. 1991: 18:393-407). A previous study (Wheeler J S, Walter J S, Zaszczurynski P J. Bladder inhibition by penile nerve stimulation in spinal cord injury patients. J. Urol. 1992: 147:100-103) in anesthetized chronic SCI cats also showed the involvement of both hypogastric and pelvic efferent nerves in the inhibitory pudendal-to-bladder spinal reflex. The inhibitory perianal-to-bladder reflex demonstrated in this study in awake chronic SCI cats might involve the same efferent pathways (i.e., hypogastric and pelvic) as revealed previously. Meanwhile, the electrical perianal stimulation can also activate an excitatory perianal-to-bladder spinal reflex to induce large amplitude bladder contractions at both low and high bladder volumes (see FIG. 22), indicating that the excitatory perianal-to-bladder reflex is independent on the afferent input from the bladder. This suggests that the excitatory afferent input from the perianal area may have projections to the parasympathetic preganglionic neurons via spinal circuitry separate from that activated by the pelvic afferent input from the bladder.

The electrical perianal stimulation is inhibitory to the bladder at 3-10 Hz (FIG. 19), but becomes excitatory at 20-50 Hz (FIG. 21). Since at the same stimulation intensity the same afferent nerve fibers are activated, the frequency selection of the perianal-to-bladder spinal reflex must occur in the spinal cord. One possible explanation is that the afferent firing at different frequencies may trigger the release of different neurotransmitters at the first spinal synapse between the primary afferent axons and spinal interneurons resulting in either an inhibitory or an excitatory effect on the bladder activity. Another possible explanation is that the spinal interneuronal networks are optimally tuned at different frequencies for bladder inhibition or excitation. Afferent firing between 20-50 Hz is optimally transmitted through the excitatory spinal neural network, but 3-10 Hz is optimal for the inhibitory network. Frequency tuning of spinal neural networks is also evident in previous studies in cats (Lindstrom S, Fall M, Carlsson C A, Erlandson B E. The neurophysiological basis of bladder inhibition in response to intravaginal electrical stimulation. J. Urol. 1983: 129:405-410 and Fall M, et al., Urol. Clin. North Amer. 1991: 18:393-407). The maximal inhibition via the hypogastric nerve could be obtained when the pudendal afferent pathway was stimulated at 5 Hz, whereas the spinal inhibition via pelvic nerve could be optimally activated at frequencies between 5 and 10 Hz (Lindstrom S, et al., J. Urol. 1983: 129:405-410 and Fall M et al., Urol. Clin. North Amer. 1991: 18:393-407).

Our current study in awake, chronic SCI animals tested the hypothesis that frequency dependent activation of the inhibitory or excitatory pudendal-to-bladder spinal reflex could be induced by applying electrical stimulation to the perianal skin area. A previous study (Walter J S, Wheeler J S, Robinson C J, Wurster R D. Inhibiting the hyperreflexic bladder with electrical stimulation in a spinal animal model. Neurourol. Urodynam. 1993: 12:241-253) using restrained, awake, chronic SCI cat only investigated the inhibitory effect on bladder by inserting fine wire electrodes percutaneously to stimulate the pudendal nerve. Whether the excitatory bladder response induced in this study could produce efficient voiding depends on the relaxation of external urethral sphincter (EUS). Although the EUS activity was not investigated in this study, the perianal stimulation presumably activated the EUS due to the excitatory pudendal-to-pudendal spinal reflex. However, the voiding problem due to dyssynergic EUS contraction could be overcome by inducing post-stimulus voiding (Brindley GS. The first 500 sacral anterior root stimulator implants: general description. Paraplegia 1994: 32:795-805). The approach employed in this study in awake SCI cats to characterize reflexes from the perianal skin to the urinary bladder might provide an alternative and practical clinical method to manage bladder function after SCI.

Example 4

Figure 24:
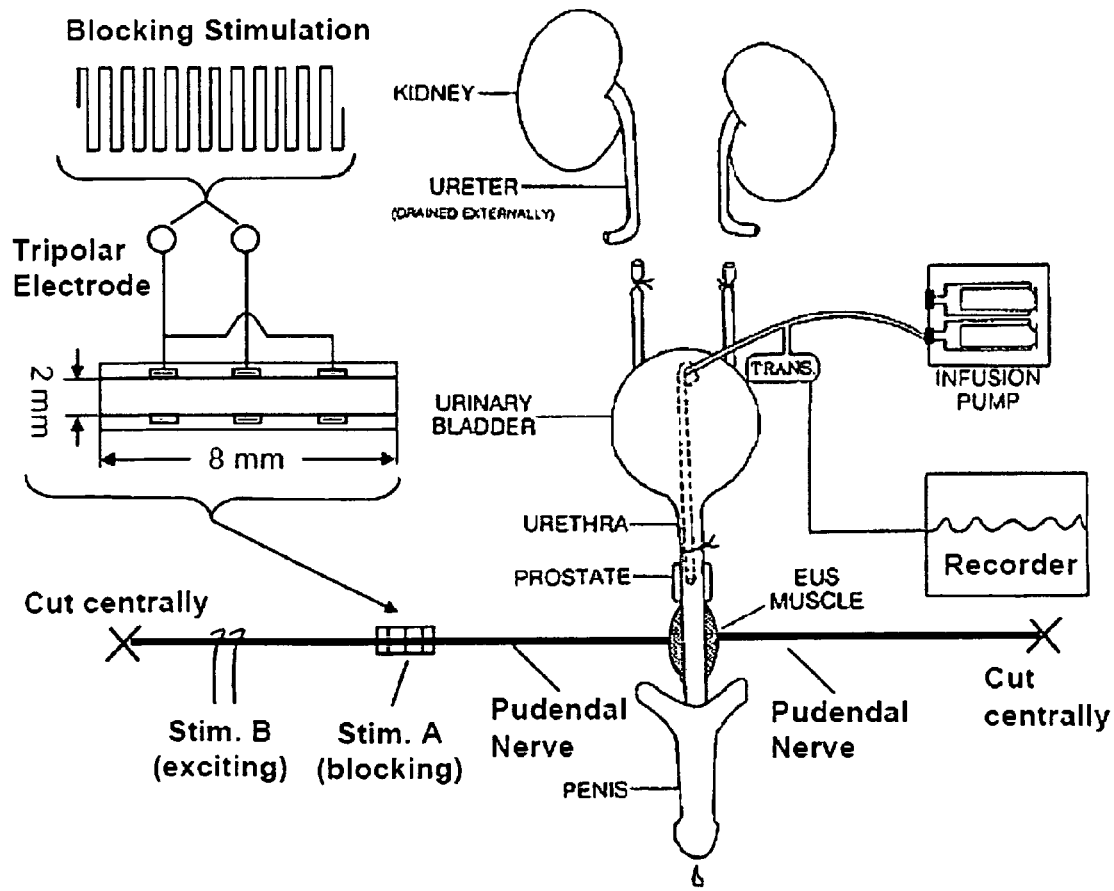
FIG. 24. Experimental setup to test the temperature influence on pudendal nerve block induced by high-frequency biphasic stimulation. EUS—External Urethral Sphincter.

The experimental setup is shown in FIG. 24. One female and two male cats (5.1 to 6.0 kg) were used under α-chloralose anesthesia (60 mg/kg i.v., supplemented as needed). The temperature of the animal was maintained at 35-37° C. using a heating pad. The ureters were cut and drained externally. A catheter (5 F) was inserted through the bladder dome into the proximal urethra and secured by a ligature near the bladder neck. The catheter was attached to both an infusion pump and a pressure transducer via a T-connector. The urethra was infused continuously with saline solution at the rate of 1-2 ml/min. The back pressure in the urethral perfusion system caused by contractions of urethral sphincter was recorded via the pressure transducer. Pudendal nerves were accessed posteriorly in the sciatic notch and cut bilaterally to eliminate any effect of the pudendal-to-pudendal spinal reflex on the experiment results. A small pool was formed around the pudendal nerve (usually on the left side) by retracting skin flaps and the pool was filled with mineral oil. A tripolar cuff electrode [shown as Stim. A in FIG. 24, Micro Probe, Inc., NC223(Pt)] was placed around one pudendal nerve (usually on the left side). The electrode leads were made of platinum wires (diameter 0.25 mm) with a distance of 2 mm between the leads. A second pair of stainless steel hook electrode (shown as Stim. B in FIG. 24) was placed on the pudendal nerve at a location central to the tripolar cuff electrode in order to test whether stimulation A could block the urethral response induced by stimulation B. A digital thermometer was used to monitor the temperature of the small mineral oil pool. The probe of the thermometer was placed adjacent to the cuff electrode and the pudendal nerve. The temperature of the mineral oil pool was adjusted between 14° C. and 37° C. by manually infusing cold or warm mineral oil into the small pool. The temperature of the mineral oil pool was maintained in a range of ±0.5° C. during each electrical stimulation period.

The high-frequency blocking stimulation tested in this study was biphasic, charge-balanced continuous rectangular wave (see FIG. 24). At a certain temperature (15, 20, 27, or 37° C.), the high-frequency stimulation (10 seconds duration) was tested at different frequencies ranging from 1 kHz to 10 kHz in 1 kHz increments to search for the minimal blocking frequency. The intensity of the high-frequency stimulation was set at about 1.5 times of the blocking threshold determined at temperature of 37° C. The determination of blocking threshold was fully described in our previous study (Tai C, Roppolo J R, de Groat W C (2005c). Response of external urethral sphincter to high frequency biphasic electrical stimulation of pudendal nerve. J Urol 174:782-7), which involved testing on both intensity and frequency. After the minimal blocking frequency was determined at different temperatures, stimulation frequency of 4 kHz was chosen to test for a nerve block effect at different temperatures ranging from 14.5° C. to 36.5° C. in 2° C. increments. The same test was repeated 3 times in each animal, and the data were presented as mean±standard error across all animals. The high-frequency, biphasic stimulation waveforms (1-10 kHz) were generated by a computer with a digital-to-analog circuit board (National Instruments, AT-AO-10), which was programmed using LabView programming language (National Instruments). Linear stimulus isolators (World Precision Instruments, A395) were used to deliver the biphasic constant current pulses to the nerve.

Results

Figure 25:
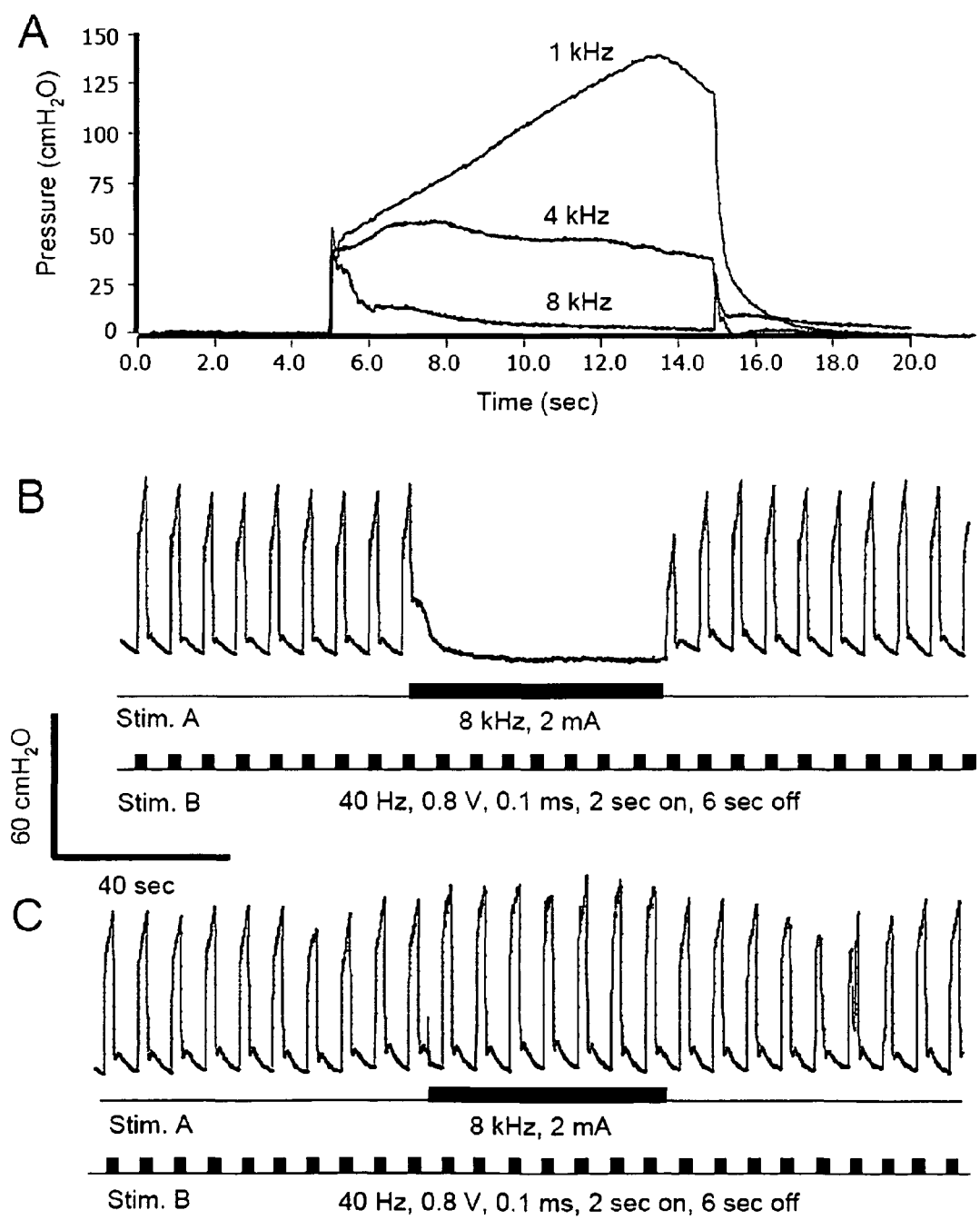
FIG. 25 Pudendal nerve block by biphasic high-frequency stimulation. A. Urethral pressure induced by 10 second blocking stimulation A alone at 2 mA intensity. B. Blocking stimulation A blocked urethral responses induced by stimulation B located centrally to the simulation A (see FIG. 24); C. Blocking stimulation A failed to block urethral responses when stimulation B was moved to a location distal to stimulation A. Black bars in B and C indicate the stimulation durations. Temperature: 37° C.

As shown in FIG. 24, the blocking stimulation A (Stim. A) was used to block the urethral pressure responses induced by the exciting stimulation B (Stim. B). When the intensity of high frequency blocking stimulation was above the blocking threshold, the urethral pressure induced by the high-frequency blocking stimulation alone was gradually reduced as the stimulation frequency increased (see FIG. 25A). During the 10 second high-frequency stimulation, a frequency high enough to suppress the urethral pressure response at the end of the stimulation (for example, 8 kHz as shown in FIG. 25A) could also block the pudendal nerve conduction (see FIG. 25B). FIG. 25B shows that the same stimulation (8 kHz, 2 mA) in the same animal blocked the urethral responses induced by the centrally located stimulation B (see FIG. 24). The urethral pressure responses could not be blocked by stimulation A if the stimulation B was moved to a location on the pudendal nerve distal to the stimulation A (see FIG. 25C). This further indicated that pudendal nerve block rather than urethral muscle fatigue was responsible for the loss of the urethral pressure responses during the high-frequency stimulation (see FIG. 25A). At stimulation intensity of 1.5 times of the blocking threshold as used in this study, FIG. 25A-C, and our previous study (Tai C, et al., J Urol 174:782-7) have shown that nerve conduction block occurred when the urethral pressure response was completely suppressed at the end of 10 second stimulation. Therefore, in this study the urethral pressure at the end of 10 second stimulation was measured to indicate the blocking effect (see FIG. 27B).

Figure 26:
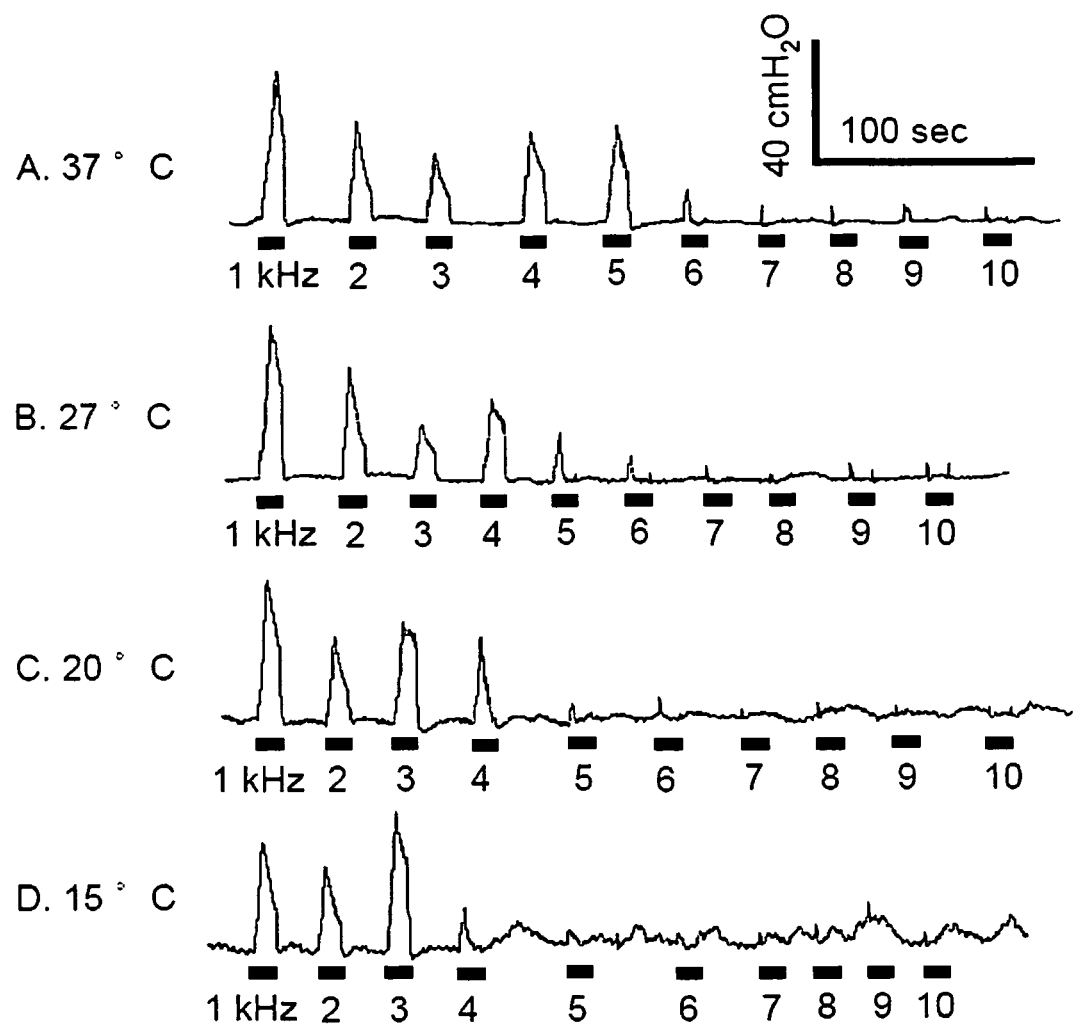
FIG. 26. Urethral responses to high-frequency biphasic electrical stimulation of pudendal nerve at different temperatures. Stimulation: 6 mA intensity, 10 sec duration. Urethral infusion rate: 2 ml/min. The black bars under each trace indicate the stimulation duration. The number under each black bar indicates the stimulation frequency in kHz.
Figure 27A:
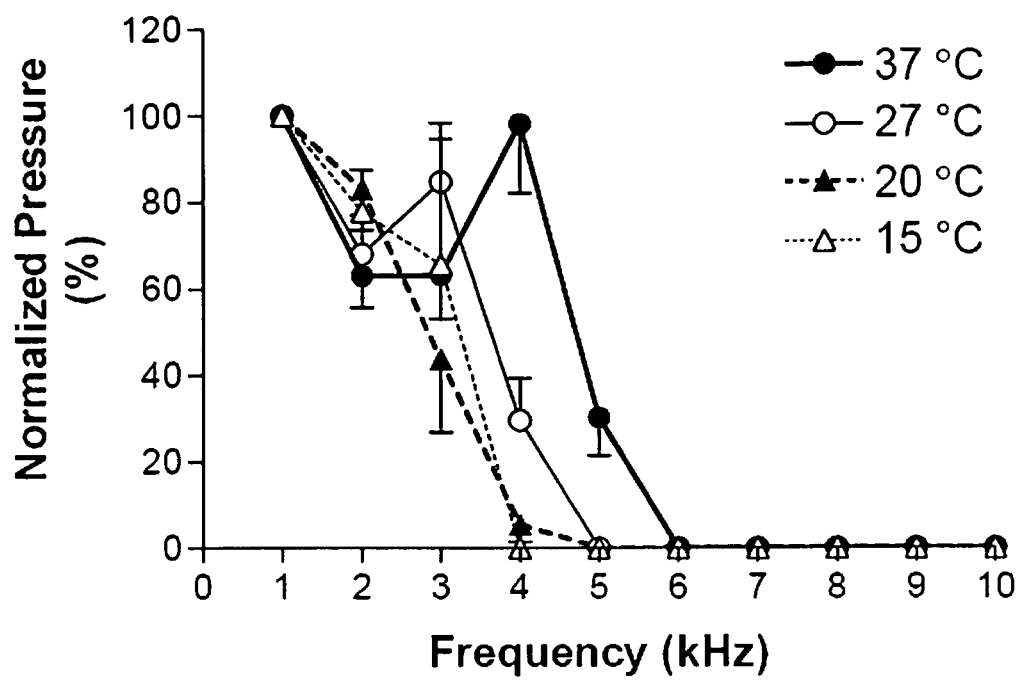
FIG. 27. A. Normalized urethral pressure responses change with stimulation frequency and temperature. Stimulation intensity: 1-6 mA. Urethral infusion rate: 1-2 ml/min. N=9. B. Expanded trace from FIG. 26 A showing that the pressures were measured at the end of 10 second stimulation. The black bars under the pressure trace indicate the 10 second stimulation duration.
Figure 27B:
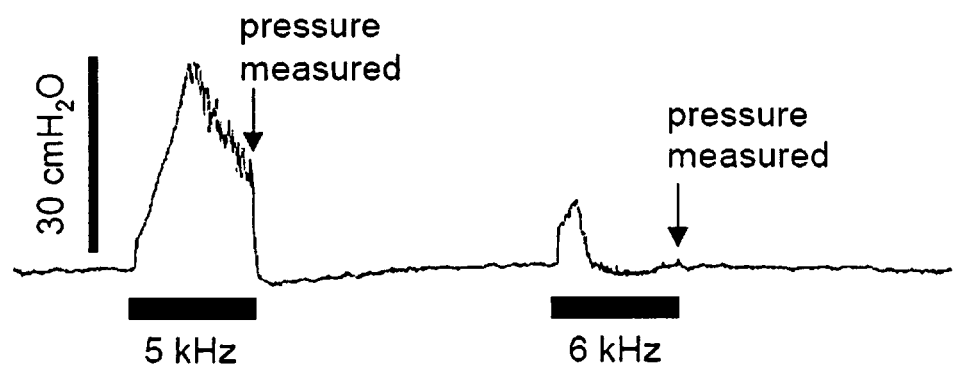

The minimal stimulation frequency required to completely block the pudendal nerve was reduced as the temperature was decreased. FIGS. 26A-D shows the urethral pressure responses to different frequencies of blocking stimulation A at different temperatures. At a temperature of 37° C. (FIG. 26A), the minimal stimulation frequency required to block pudendal nerve conduction during the 10 second stimulation was 6 kHz. This minimal frequency was reduced to 5 kHz when the temperature was decreased to 27° C. (FIG. 26B). At a temperature of 20° C. (FIG. 26C), the block occurred at the end of the 10 second stimulation with frequency of 4 kHz. Further decreasing the temperature to 15° C. (FIG. 26D) resulted in the block occurring at stimulation frequency of 4 kHz in less than 10 seconds. FIGS. 26A-D shows that the minimal blocking frequency changed from 6 kHz at 37° C. to 4 kHz at 15-20° C. The tests as shown in FIGS. 26A-D were repeated 3 times in each animal. FIG. 27A summarizes the experimental results from all 3 animals (N=9). The urethral pressure at the end of 10 second high-frequency stimulation was measured to indicate the blocking effect (see FIG. 27B). At a certain temperature, the urethral pressures induced by stimulation at different frequencies were normalized to the pressure induced by stimulation at 1 kHz. As shown in FIG. 27A, the normalized pressure-frequency curve was shifted toward a lower frequency when the temperature was decreased from 37° C. to 15° C. The minimal stimulation frequency to induce a complete block was reduced from 6 kHz to 4 kHz as the temperature was decreased from 37° C. to 15° C.

Based on the results shown in FIG. 27A stimulation frequency of 4 kHz was chosen to determine more precisely the temperature threshold at which the nerve block occurred. The frequency of 4 kHz was tested because the urethral pressure response at this frequency changed from 0% to almost 100% when the temperature was increased from 15° C. to 37° C. (see FIG. 27A). Therefore, testing 4 kHz could show a full range of responses.

Figure 28:
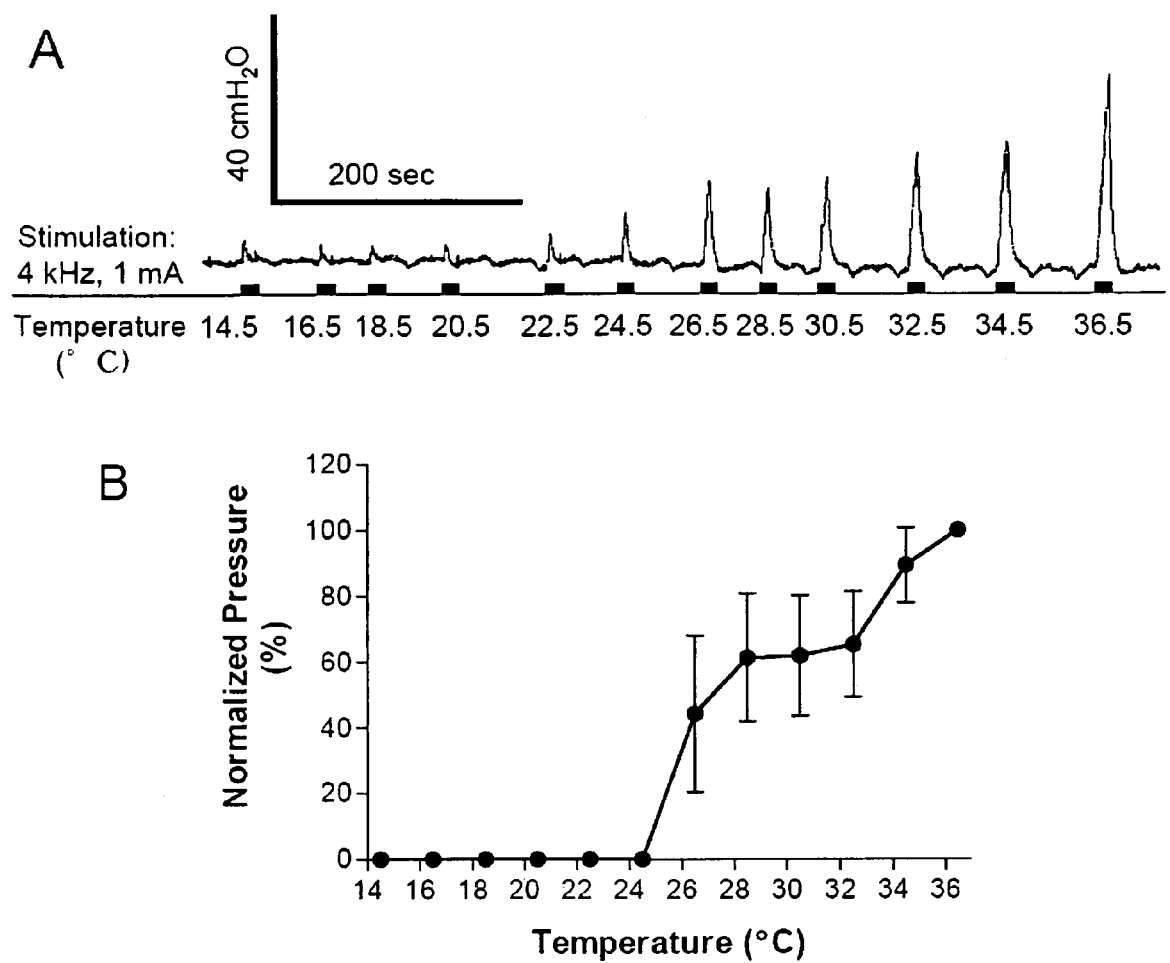
FIG. 28. A. Temperature influence on urethral response to high-frequency biphasic electrical stimulation of pudendal nerve. Stimulation: 4 kHz frequency, 1 mA intensity, 10 sec duration. Urethral infusion rate: 2 ml/min. The black bars indicate the stimulation duration. The number under each black bar indicates the temperature during the time when the stimulation was applied. B. Summary of the temperature influence on the normalized urethral pressure responses. Stimulation: 4 kHz frequency, 1-6 mA intensity. Urethral infusion rate: 1-2 ml/min. N=9.

FIG. 28A shows how the urethral response to the 4 kHz stimulation recovered gradually when the temperature was increased from 14.5° C. to 36.5° C. in 2° C. increments. At temperatures below 24.5° C., stimulation at 4 kHz could completely block the pudendal nerve conduction within the 10 second stimulation. This test was repeated 3 times in each animal. The results are summarized in FIG. 28B (N=9), in which the urethral pressure measurements were normalized to the value induced at a temperature of 36.5° C. FIG. 28B shows that the 4 kHz stimulation could completely block the nerve conduction only when the temperature was below 24.5° C.

In summary, for a certain stimulation frequency there is a corresponding maximal temperature below which the stimulation can completely block the nerve conduction (see FIGS. 28A and B). For a certain temperature there is a corresponding minimal stimulation frequency above which the nerve can be completely blocked (see FIGS. 26A-D and 27A and B). Therefore, the minimal frequency and the maximal temperature are paired in a one-to-one relationship. At a higher temperature, a higher stimulation frequency is required to completely block nerve conduction.

Discussion

The results presented in this study showed that experimental temperature could be one of the factors that influences the minimal blocking frequency, although other factors might also be involved including electrode geometry (bipolar or tripolar), different nerves (sciatic nerve or pudendal nerve), or different species (frog, rat, or cat). Studies using rat sciatic nerves (Bhadra N, Kilgore K L (2005). High-frequency electrical conduction block of mammalian peripheral motor nerve. Muscle Nerve 32:782-790 and Williamson R P, Andrews B J (2005). Localized electrical nerve blocking. IEEE Trans Biomed Eng 52:362-370) showed that consistent nerve block could be achieved at stimulation frequency greater than 10 kHz. However, the experimental temperature was not defined, although Williamson R P, et al. stated that the body of each rat was warmed during the tests by radiant heat from above and a heating pad beneath. In that reference, in the frequency range between 5 kHz and 10 kHz, nerve block was not consistent and variable results were obtained in different rats. This variable result might be partially caused by the un-controlled experimental temperature in different animals. A recent study (Bhadra N, Bhadra N, Kilgore K, Gustafson K J (2006). High frequency electrical conduction block of pudendal nerve. J Neural Eng 3: 180-187) using cat pudendal nerve found that nerve block could be observed between 1 kHz and 30 kHz, but the frequency range to induce a complete block varied significantly between animals. Although in Bhadra N, et al., the animal's body temperature was maintained between 37° C. and 39° C. using a thermal blanket, the method to control the pudendal nerve temperature was not described after the nerve was exposed for electrode placement. Our previous studies using cats (Tai C, Roppolo J R, de Groat W C (2004). Block of external urethral sphincter contraction by high frequency electrical stimulation of pudendal nerve. J Urol 172:2069-2072 and Tai C, et al. (2005c) J Urol 174:782-786) indicated that at temperatures between 35° C. and 37° C. the minimal stimulation frequency to block the pudendal nerve conduction was around 6 kHz. The pudendal nerve temperature in our previous studies Id. was controlled by covering the exposed nerve with warm Krebs solution or mineral oil. The minimal stimulation frequency of 4-5 kHz was reported in other studies using cat sciatic nerves, where the temperature varied between 25° C. and 35° C. or was undefined (presumably at room temperature 20-25° C.) (Bowman B R, McNeal D R (1986). Response of single alpha motoneurons to high-frequency pulse train: firing behavior and conduction block phenomenon. Appl Neurophysiol 49:121-138; Reboul J, Rosenblueth A (1939). The action of alternating currents upon the electrical excitability of nerve. Am J Physiol 125:205-215; and Rosenblueth A, Reboul J (1939) The blocking and deblocking effects of alternating currents on nerve. Am J Physiol 125:251-264).

More recently, a study using isolated frog sciatic nerve reported that nerve block could be observed at a stimulation frequency as low as 1 kHz at room temperature (Kilgore K L, Bhadra N (2004). Nerve conduction block utilising high-frequency alternating current. Med Biol Eng Comput 42:394-406). But more effective or consistent block could be achieved between 3 kHz and 5 kHz. It is unfortunate that the specific room temperature was not defined in this study. It is worthy noting that the temperature influence could only partially explain the discrepancy of minimal blocking frequency (1-10 kHz) presented in previous animal studies, since it only caused the minimal blocking frequency changing from 6 kHz to 4 kHz in the temperature range of 15-37° C. based on the results from this study.

Due to the high frequency electrical artifacts during the stimulation, it is very difficult to investigate the possible mechanisms underlying the nerve conduction block in animal experiments using electrophysiology techniques. However, our previous studies using axonal models and computer simulation (Zhang X, Roppolo J R, de Groat W C, Tai C (2006b). Mechanism of Nerve Conduction Block Induced by High-Frequency Biphasic Electrical Currents. IEEE Trans Biomed Eng, 53:2445-2454 and Wang J, Shen B, Roppolo J R, de Groat W C, Tai C (2007). Influence of frequency and temperature on the mechanisms of nerve conduction block induced by high-frequency biphasic electrical current. J Comp Neurosci, in press) have shown that the constant activation of potassium channels under the block electrode is a possible mechanism underlying the nerve conduction block. As the stimulation frequency increases, the potassium channel changes from opening and closing alternatively to opening constantly when the stimulation frequency reaches the threshold level (i.e. the minimal blocking frequency). The dynamics of potassium channel activation is temperature dependent. As the temperature decreases, the potassium channel opens and closes much slower requiring a lower minimal blocking frequency to keep the potassium channel open constantly. The results from this animal study agree with the conclusion from our previous computer simulation studies.

Nerve damage will always be a concern when electrical stimulation is applied chronically. However, a biphasic, charge-balanced stimulation waveform was used in this study which is safer than uniphasic, charge-unbalanced stimulation. Also, when the blocking stimulation is applied to treat detrusor sphincter dyssynergia, it will only last 1-2 minutes at the time of voiding for 4-7 times per day. This short stimulation time is also relatively safe for peripheral nerves (See, e.g., Agnew W F, McCreery DH (1990). Neural Prostheses: Fundamental Studies. Prentice Hall, Englewood Cliffs, N.J.). Our previous study also showed that the biphasic blocking stimulation (1 minute in duration), which was repeatedly (12 times) applied to the same site on the pudendal nerve during a period of 43 minutes, did not influence the ability of pudendal nerve to induce sphincter contractions in the absence of blocking stimulation (Tai C, et al. (2005c) J Urol 174:782-786). This suggested that little damage to the pudendal nerve occurred during this period. Furthermore, a stimulation frequency of 4.8 kHz was safely applied in human cochlear implants (Rubinstein J T, Tyler R S, Johnson A, brown C J (2003). Electrical suppression of tinnitus with high-rate pulse trains. Otol Neurotol 24:478-485). The duration of auditory nerve stimulation is much longer than what is needed to block external urethral sphincter contraction during voiding. Therefore, the nerve blocking method employing a biphasic, charge-balanced stimulation waveform is very promising for use in applications to treat detrusor sphincter dyssynergia and facilitate voiding.

This study was aimed at designing a neural prosthetic device to reversibly block pudendal nerve conduction and facilitate voiding in spinal cord injured people. Since human body temperature is about 37.5° C., a stimulation frequency of, without limitation, in the range of from 6 kHz to 10 kHz may be preferred in many instances to block the pudendal nerve in humans. Therefore, in one non-limiting embodiment, a neural prosthetic device may be designed to deliver stimulation frequencies ranging from 4-6 kHz to 10 kHz in order to have additional flexibility. As indicated above, optimal blocking frequencies may vary from individual-to-individual and for each optimal individual, stimulation and blocking frequencies may be determined by voiding efficiency, (e.g., voiding rate).

Example 5

Materials and Methods

Voiding reflexes induced by electrical stimulation of the pudendal nerve were evaluated in three female, chronic SCI cats (3.7-4.3 kg). Spinal cord transection was performed (3-11 months prior to the experiment) at T9-T10 vertebral level by a dorsal laminectomy under isoflurane anesthesia and aseptic conditions. After injection of a local anesthetic (lidocaine, 1%) first on the spinal cord surface and then into the cord through the dura, the spinal cord was cut completely. A piece of gel foam was placed between the cut ends (usually a separation of 2-3 mm). The muscle and skin were then sutured and after full recovery from anesthesia the animal was returned to its cage. Antibiotic (Amoxicillin Trihydrate/Clavulanate Potassium, 15-20 mg/kg) was administered at the time of surgery and again the day following surgery. The bladder was manually expressed twice a day to prevent bladder over-distension and infection. Approximately 3-4 weeks after spinal cord transection, spinal micturition reflexes in response to bladder distension or tactile stimulation of the perigenital region were prominent. At the time of experiments 3-11 months after spinal cord transection, the bladder function had been stabilized in all of the animals.

During the experiments animals were anesthetized with α-chloralose (60 mg/kg i.v., supplemented as needed). A double lumen catheter (5 French) was inserted into the bladder via the dome and secured by a ligature. One lumen of the catheter was attached to a pump to infuse the bladder with saline, and the other lumen was connected to a pressure transducer to monitor the bladder activity. A funnel was used to collect the voided volume into a beaker that was attached to a force transducer to record the volume. The pudendal nerve (usually on the left side) was accessed posteriorly between the sciatic notch and the tail. A tripolar cuff electrode [Micro Probe, Inc., Gaithersburgh, Md., USA, NC223(Pt)] was placed around the pudendal nerve at a location central to the deep perineal branch. The electrode leads were made of platinum wires (diameter 0.25 mm) with a 2 mm distance between the leads. After implanting the pudendal nerve electrode, the muscle and skin were closed by sutures. The temperature of the animal was maintained at 35-37° C. using a heating pad.

Uniphasic pulses (pulse width 0.2 msec) of 2-10 V intensity were used to stimulate the pudendal nerve at frequency of 3 or 20 Hz. The stimulation intensity was determined at the beginning of each experiment by a preliminary test of its effectiveness to induce voiding at the frequency of 20 Hz. Stimulation intensity was gradually increased during the preliminary test until it could generate peak bladder pressure above 40 cmH$_2$O. At this intensity post-stimulus voiding could be induced. Once the intensity was determined, it was used for both 3- and 20-Hz stimulation throughout the same experiment. Anal sphincter contractions were clearly observable at the stimulation intensities used. A Grass S88 stimulator (Grass Medical Instruments) with stimulus isolator (Grass Medical Instruments, SIU5) was used to generate stimulus pulses. In order to instill saline into the bladder and induce voiding reflexes, slow infusion (2-4 ml/min) of the bladder was always started with the bladder empty (i.e., a cystometrogram—CMG). Multiple CMGs were performed in each animal. During some of the CMGs when the bladder was filled to half of its control capacity, continuous stimulation of the pudendal nerve at 3 Hz was applied in order to suppress reflex bladder activity and increase bladder capacity. Bladder capacity was defined as the infused volume at which a bladder contraction was induced and fluid was released from the bladder, or when fluid leaked from the bladder in the absence of bladder contraction. When fluid was released from bladder, the infusion was stopped immediately. Then, the bladder was either allowed to contract spontaneously several times to evaluate voiding efficiency, or 20-Hz stimulation was applied to the pudendal nerve to induce a voiding reflex and bladder emptying. Bladder capacities and number of non-voiding contractions were measured during CMGs with or without 3-Hz pudendal nerve stimulation to determine the inhibitory effect on bladder induced by pudendal nerve stimulation. Voiding efficiency, residual bladder volume, peak bladder pressure, and average flow rate were also measured in order to evaluate the effectiveness of 20-Hz pudendal nerve stimulation to induce voiding. Voiding efficiency is defined as the total voided volume divided by the total infused volume. Parameters measured from multiple trials in the same animal were averaged, and the final data are presented as mean±standard error (SE) for three animals. Paired T-test was used to determine statistical significance (P<0.05).

Results

Voiding Induced by Bladder Distension

In chronic SCI cats, voiding induced by bladder distension was very inefficient. As shown in FIG. 29A, when the bladder was slowly filled at the rate of 4 ml/min, several reflex bladder contractions appeared first, but no voiding occurred. These initial reflex bladder contractions were defined as non-voiding contractions. When bladder volume increased, a reflex bladder contraction defined as a voiding contraction could elicit the release of saline from bladder. As shown in FIG. 29A the voiding contraction occurred just before stopping the infusion after a total of 86 ml was infused. Although several additional reflex bladder contractions occurred after the infusion was stopped, no further release of saline from the bladder was observed. The voided volume was only 3 ml and the residual volume remaining in the bladder was 83 ml (voiding efficiency=3.5%). Repeated tests in three cats (Table 2) revealed a consistent low voiding efficiency (range 5.7%-8.7%, average 7.3%, FIG. 30C) and large residual volume (92.7%, FIG. 30D).

TABLE 2

Measurements from each cat under different experimental conditions

| | | Cat #1 | Cat #2 | Cat #3 |
|---|---|---|---|---|
| Control | Bladder capacity (ml) | 79.3 ± 2.4 (6) | 22.6 ± 0.6 (11) | 25.0 ± 1.3 (6) |
| | Voiding efficiency (%) | 5.7 ± 0.7 (6) | 7.6 ± 0.9 (8) | 8.7 ± 2.4 (3) |
| | Bladder pressure (cmH$_2$O) | 26.1 ± 2.0 (18) | 23.0 ± 1.0 (18) | 20.2 ± 1.9 (12) |
| | Flow rate (ml/sec) | 0.29 ± 0.05 (18) | 0.30 ± 0.03 (18) | 0.09 ± 0.04 (12) |
| | Number of non-voiding contractions | 6.0 ± 0.6 (6) | 3.1 ± 0.4 (8) | 7.7 ± 0.6 (6) |
| 3 Hz | Normalized capacity (%) | 150.5 ± 3.0 (3) | 155.7 ± 2.2 (6) | 135.3 ± 11.2 (6) |
| | Voiding efficiency (%) | 22.6 ± 1.4 (3) | 37.1 ± 0.0 (1) | 16.5 ± 1.5 (3) |
| | Number of non-voiding contractions | 0.3 ± 0.3 (3) | 0.7 ± 0.3 (6) | 2.5 ± 0.8 (6) |
| 20 Hz | Voiding efficiency (%) | 94.2 ± 2.8 (2) | 90.3 ± 4.1 (4) | 90.4 ± 1.9 (6) |
| | Bladder pressure (cmH$_2$O) | 36.0 ± 2.3 (12) | 30.6 ± 1.0 (30) | 51.4 ± 1.9 (36) |
| | Flow rate (ml/sec) | 0.96 ± 0.04 (12) | 0.98 ± 0.03 (30) | 0.85 ± 0.03 (36) |
| 3 + 20 Hz | Voiding efficiency (%) | 78.4 ± 2.6 (2) | 88.9 ± 3.4 (6) | 91.1 ± 1.6 (6) |

Control—Voiding induced by bladder distension alone without any stimulation.
3 Hz—3-Hz pudendal nerve stimulation applied during a slow bladder filling.
20 Hz—20-Hz pudendal nerve stimulation applied at the end of bladder filling.
3 + 20 Hz—Voiding induced by 20-Hz stimulation with prior 3-Hz stimulation. Bladder pressure-peak pressure during voiding contractions. At the end of each CMG, voiding occurred with several voiding contractions. Bladder pressure and flow rate were measured from individual voiding contractions, but the voiding efficiency was calculated from the total voided volume for each CMG. The numbers in parentheses indicate the number of measurements in each animal.

Pudendal nerve stimulation at 3 Hz inhibited reflex bladder activity and increased bladder capacity. As shown in FIG. 30B the 3 Hz stimulation (8 V, 0.2 msec) was applied to the pudendal nerve when the infused volume was about half of the control capacity. At the start of the stimulation, it induced a small bladder contraction without voiding. The 3-Hz stimulation completely inhibited non-voiding bladder contractions, and increased bladder capacity to 116 ml at which point fluid leaked from the bladder due to the relatively high baseline pressure. When the nerve stimulation was stopped, several reflex bladder contractions occurred accompanied by voiding of small volumes. A total of 26 ml was voided leaving a residual volume of 90 ml in the bladder. Although a larger volume (26 vs. 3 ml) was voided after termination of the 3 Hz inhibitory pudendal nerve stimulation and voiding efficiency was increased (22.4% vs. 3.5%), the 3 Hz stimulation did not reduce the residual bladder volume (90 vs. 83 ml) due to a larger bladder capacity.

Table 2 and FIG. 30A summarize the increase in bladder capacity in three animals induced by 3 Hz stimulation of the pudendal nerve. In each animal bladder capacities were normalized to the averaged capacity measured during the control period (i.e., without 3 Hz stimulation). The 3 Hz stimulation significantly (P<0.05) increased bladder capacity to 147.2%±6.1% of the control capacity. Meanwhile, it also inhibited reflex bladder activity and significantly (P<0.05) reduced the total number of non-voiding bladder contractions from 5.6±1.3 to 1.2±0.7 (see FIG. 30B). FIG. 30C summarizes the efficiency of voiding induced by bladder distension in three animals. CMGs in the absence of 3-Hz pudendal nerve stimulation induced a low voiding efficiency (7.3%±0.9%). The 3-Hz stimulation not only increased the bladder capacity (see FIG. 30A) but also slightly increased voiding efficiency to 25.4%±6.1% (not significant, P>0.05). Residual bladder volumes after reflex bladder contractions with or without 3-Hz pudendal nerve stimulation are shown in FIG. 30D. The residual volumes were normalized to the averaged control capacity in each animal. Under control conditions, 92.7%±0.9% of the infused volume remained in the bladder after the voiding. Although 3-Hz stimulation of the pudendal nerve significantly increased bladder capacity (see FIG. 30A), it did not reduce the absolute residual volume, but rather slightly increased it by approximately 10% (see FIG. 30D).

Voiding Induced by 20-Hz Stimulation of Pudendal Nerve

Figure 31:
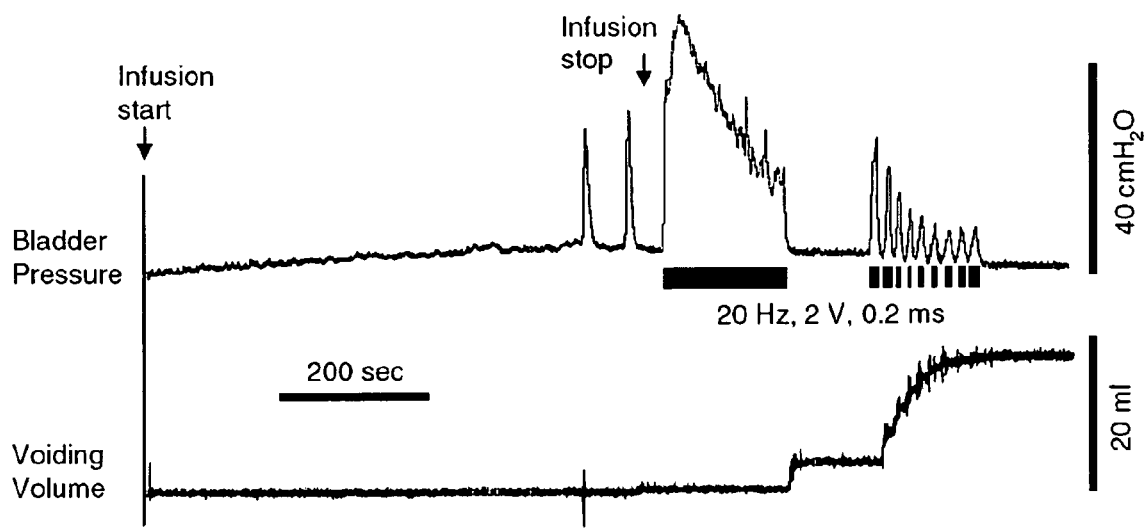
FIG. 31. Voiding induced by 20-Hz stimulation of the pudendal nerve in a chronic SCI cat (9 months). Total 23 ml was infused into the bladder and 18 ml was voided. The black bars under the bladder pressure trace indicate stimulation durations. Stimulation: 20-Hz frequency, 2 V intensity, 0.2 msec pulse width. Infusion rate: 2 ml/min.

Electrical stimulation of the pudendal nerve at 20 Hz applied at the end of the CMG induced a large amplitude, long-lasting bladder contraction (FIG. 31). However, voiding only occurred after the stimulation was terminated (i.e., post-stimulus voiding, see FIG. 31 lower trace) because the external urethral sphincter, which is innervated by the pudendal nerve, was also activated during the 20-Hz stimulation. When the stimulation was stopped, the external urethral sphincter (striated muscle) relaxed faster than the detrusor (smooth muscle) allowing bladder pressure to exceed urethral pressure, and thereby inducing post-stimulus voiding.

As shown in FIG. 31, intermittent, short burst, pudendal nerve stimulation at 20 Hz could induce a series of poststimulus voiding responses, which resulted in a total of 18 ml voided out of the 23 ml infused (voiding efficiency=78.3%). In this study, the intermittent stimulation was generated manually by switching on/off the stimulator while visually monitoring the bladder pressure. With the bladder gradually emptying, the intermittent 20 Hz stimulation generated a series of gradually decreasing bladder pressures, and voiding eventually stopped.

Figure 32:
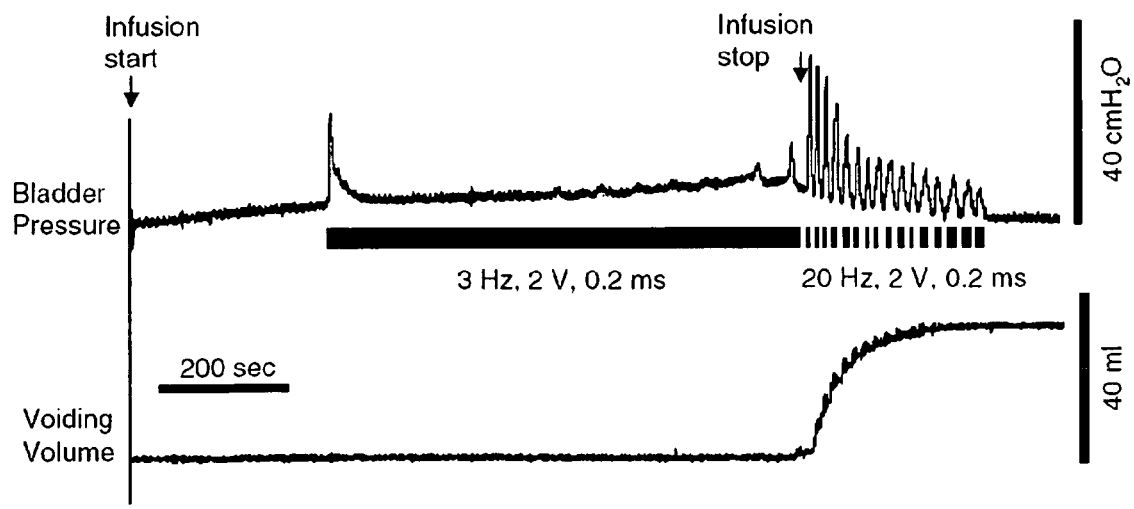
FIG. 32. Voiding induced by intermittent 20-Hz pudendal nerve stimulation following 3-Hz continuous stimulation in a chronic SCI cat (9 months). Thirty-four milliliter was infused into the bladder and 32 ml was voided. The black bars under the bladder pressure trace indicate stimulation durations. Stimulation: 2 V intensity, 0.2 msec pulse width. Infusion rate: 2 ml/min.

The post-stimulus voiding induced by intermittent, short burst, 20-Hz stimulation was also evaluated after the bladder capacity was significantly increased by 3 Hz stimulation. As shown in FIG. 32, the 3-Hz stimulation increased the bladder capacity from 23 to 34 ml (FIGS. 31 and 32 show results from the same animal). The intermittent 20-Hz stimulation produced a total voided volume of 32 ml resulting in a voiding efficiency of 94.1%.

Figure 33:
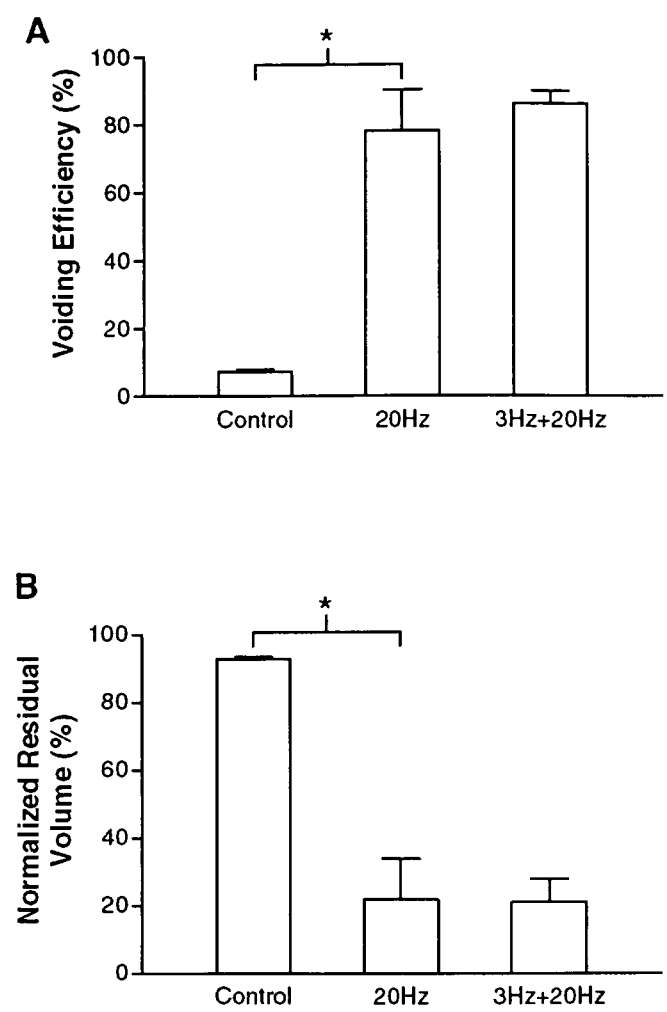
FIG. 33. Voiding efficiency (A) and residual bladder volume (B) induced by intermittent 20-Hz pudendal nerve stimulation in three chronic SCI cats (N=3). Control—Voiding induced by bladder distension alone. 20 Hz—Voiding induced by intermittent 20-Hz stimulation without prior 3-Hz continuous stimulation. 3 Hz+20 Hz—Voiding induced by intermittent 20-Hz stimulation with prior 3-Hz continuous stimulation. Stimulation: 2-10 V intensity, 0.2 msec pulse width. Infusion rate: 2-4 ml/min. *indicates statistical significance (P<0.05).

Table 2 and FIG. 33A summarize the voiding efficiencies induced by intermittent 20 Hz stimulation of the pudendal nerve in all animals. Compared to the efficiency of voiding induced by bladder distension alone, intermittent 20 Hz stimulation of the pudendal nerve significantly (P<0.05) increased the voiding efficiency from 7.3%±0.9% to 78.3%±12.1%. When 3-Hz stimulation was applied during bladder filling to increase bladder capacity, the intermittent 20-Hz stimulation produced a voiding efficiency of 86.1%±3.9% (see FIG. 33A), which was not significantly different from 20-Hz stimulation alone (P>0.05). FIG. 33B summarizes the residual bladder volumes in all animals after voiding induced by the intermittent 20-Hz stimulation with or without the prior 3-Hz stimulation. The residual volume was normalized to the averaged control capacity in each animal. Compared to the residual volumes after the voiding induced by bladder distension alone, the intermittent 20-Hz stimulation significantly (P<0.05) reduced the bladder residual volumes from 92.7%±0.9% to 21.7%±12.1%. However, the 3-Hz stimulation applied prior to the intermittent 20-Hz stimulation did not further reduce the residual volumes (21.0%±6.8%, see FIG. 33B).

Figure 34:
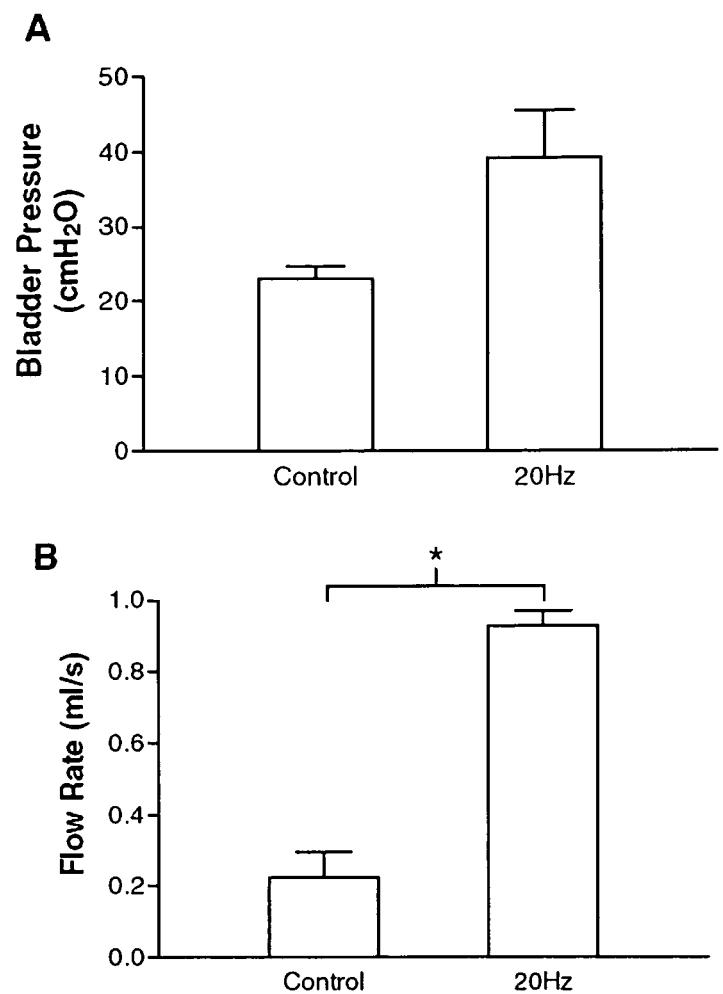
FIG. 34. Peak bladder pressure (A) and average flow rate (B) induced by bladder distension or by intermittent 20-Hz stimulation in three chronic SCI cats (N=3). Control—Voiding induced by bladder distension. 20 Hz—Voiding induced by intermittent 20-Hz stimulation. Only the peak bladder pressures and the average flow rates of the first three voids during a series of voids induced by intermittent 20-Hz stimulation were measured. Stimulation: 2-10 V intensity, 0.2 msec pulse width. Infusion rate: 2-4 ml/min. *indicates statistical significance (P<0.05).

FIG. 34A compares the peak bladder pressures during voiding induced by bladder distension (see FIG. 29) with the averaged peak bladder pressures during the first three voidings induced by the intermittent 20-Hz stimulation (see FIG. 32). The average peak bladder pressure (39.3±6.3 cmH$_2$O) induced by intermittent 20-Hz stimulation of the pudendal nerve was not significantly higher than the average peak bladder pressure (23.1±1.7 cmH$_2$O) induced by bladder distension (FIG. 34A, P>0.05). FIG. 34B compares the average flow rates during the voidings induced by bladder distension and by intermittent 20-Hz stimulation of the pudendal nerve. The average flow rates during intermittent 20-Hz stimulation were also measured during the first three short bursts of stimulation (see FIG. 32) when the bladder volume was still large and comparable to the bladder volume during the voiding induced by bladder distension (see FIG. 29). The intermittent 20-Hz stimulation of the pudendal nerve increased the voiding flow rate significantly (P<0.05) from 0.23±0.07 to 0.93±0.04 ml/sec (FIG. 34B).

Discussion

Figure 29:
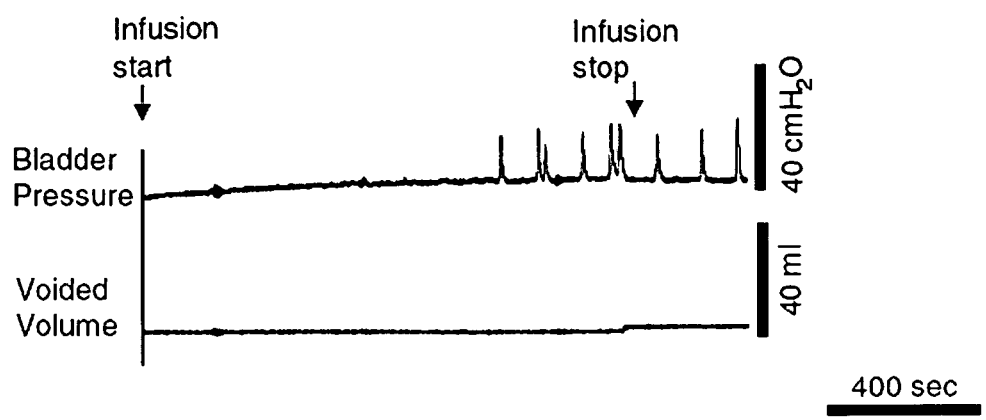
FIG. 29. Voiding induced by slow infusion of saline into the bladder in a chronic SCI cat (11 months). A: CMG without nerve stimulation. Total 86 ml was infused into the bladder, but only 3 ml was voided. B: CMG with 3-Hz stimulation of the pudendal nerve shows a suppression of non-voiding contractions and an increase in bladder capacity. Total 116 ml was infused into the bladder, and 26 ml was voided. The black bar in B under the bladder pressure trace indicates stimulation duration. Stimulation: 3 Hz frequency, 8 V intensity, 0.2 msec pulse width. Infusion rate: 4 ml/min.
Figure 29:
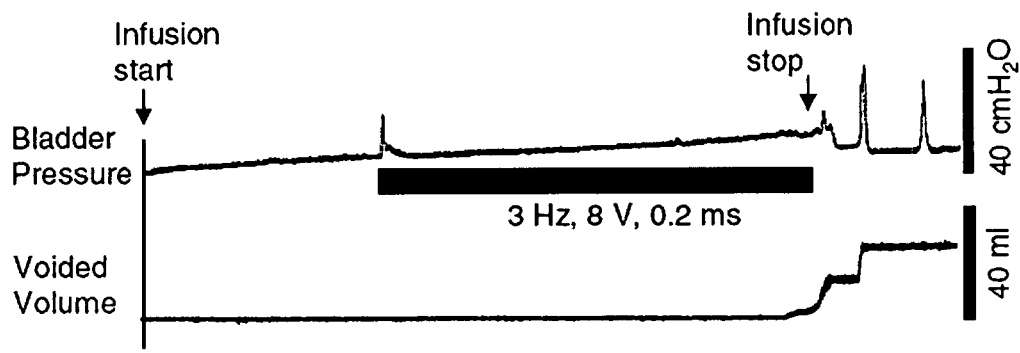
Figure 30:
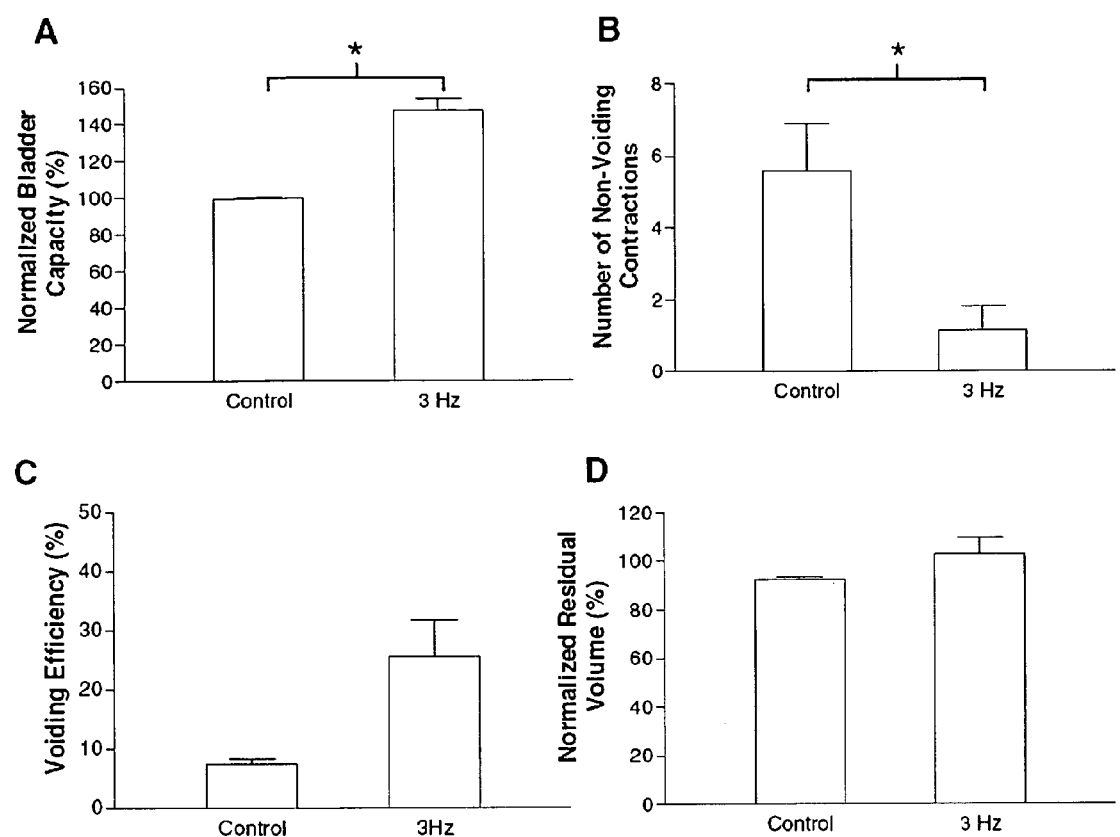
FIG. 30. Bladder capacity (A), number of non-voiding contractions (B), voiding efficiency (C), and residual volume (D) with or without 3-Hz pudendal nerve stimulation in three chronic SCI cats (N=3). Control—without 3 Hz nerve stimulation. 3 Hz—with 3-Hz nerve stimulation. Stimulation: 2-10 V intensity, 0.2 msec pulse width. Infusion rate: 2-4 ml/min. *indicates statistical significance (P<0.05).

This study in anesthetized chronic SCI cats has shown that storage and voiding functions of the lower urinary tract, which are impaired after SCI, could be improved by activation of the somatic afferent pathways in the pudendal nerve. Electrical stimulation of the pudendal nerve at 3 Hz inhibited non-voiding contractions during bladder filling, suppressed reflex voiding, and increased bladder capacity (FIGS. 29 and 30). Thus the 3 Hz pudendal nerve stimulation converted the overactive bladder (small capacity with many non-voiding contractions during storage phase, see FIG. 29A) to a quiescent larger capacity bladder (see FIG. 29B). Furthermore, voiding efficiency which is very low in chronic SCI cats was significantly increased by intermittent 20-Hz stimulation of the pudendal nerve (see FIG. 33A). Although the peak bladder pressures induced by intermittent 20-Hz stimulation of the pudendal nerve were not significantly higher than those induced by bladder distension alone (FIG. 34A), the average flow rates were significant faster with the stimulation (FIG. 34C). This study shows that after SCI the spinal voiding reflex in cats can be either inhibited or activated depending on the frequency of pudendal nerve stimulation (i.e., 3 or 20 Hz).

In anesthetized cats with an intact spinal cord, reflex micturition is mediated by a spinobulbspinal reflex involving a control center located in the rostral pons—Pontine Micturition Center (PMC). The PMC coordinates the activity of bladder and urethra, so that during storage the bladder is quiescent and the urethra is closed, whereas during voiding the bladder contracts and the urethra relaxes. After SCI, this coordination is lost due to the absence of supraspinal control. However, a few weeks after SCI, a spinal micturition reflex emerges. This spinal reflex results in frequent bladder contractions during storage (i.e., neurogenic detrusor overactivity), inefficient voiding, and a large residual bladder volume (see FIGS. 29 and 30).

As indicated above, a recent study showed that intermittent pudendal nerve stimulation at 33 Hz induced a voiding reflex in cats with an intact spinal cord. However, it is very difficult to attribute this voiding effect solely to a spinal reflex in normal cats, since the spinobulbospinal micturition reflex is intact and the PMC coordinates voiding once the bladder contraction is initiated by pudendal nerve stimulation. After SCI the spinal reflexes of the lower urinary tract undergo significant plasticity. Our previous study (Tai C, Smerin SE, de Groat W C, et al. Pudendal-to-bladder reflex in chronic spinal-cord-injury cats. Exp Neurol 2006; 197:225-34) using chronic SCI cats showed that the property of pudendal-to-bladder spinal reflex was frequency dependent (inhibitory at 3 Hz, but excitatory at 20 Hz). Here, we further showed that although the parasympathetic bladder-to-bladder spinal reflex after SCI could not induce efficient voiding, the pudendal-to-bladder spinal reflex could either increase bladder capacity or induce efficient voiding when the pudendal nerve (somatic pathway) was stimulated at frequency of 3 or 20 Hz.

In our previous study of chronic SCI cats, a large amplitude, long-lasting, rebound bladder contraction was observed at the termination of the inhibitory 3-Hz pudendal nerve stimulation when the urethral outlet was closed. Therefore, it was expected that this large rebound bladder contraction might be able to induce efficient voiding if the urethral outlet was open. However, here we failed to induce this large rebound bladder contraction with an open urethra. Instead, several small, short-lasting bladder contractions followed the termination of the inhibitory 3-Hz pudendal nerve stimulation (FIG. 29B), which slightly increased the voiding efficiency (FIG. 30C), but the absolute residual volume was still large (FIG. 30D). Similar short-lasting bladder contractions were also observed in awake, chronic SCI cats (Walter J S, Wheeler J S, Cai W Y, et al. Direct bladder stimulation with suture electrodes promotes voiding in a spinal animal model: A technical report. J Rehab Res Dev 1997; 34:72-81). This very different bladder response might be related to the condition of the urethra, that is, either open or closed. The bladder volume was much larger than its control capacity at the end of inhibitory pudendal nerve stimulation (see FIG. 29). Once the inhibition was removed, the excitatory parasympathetic bladder-to-bladder spinal reflex would induce a bladder contraction. If the urethra was closed at this moment, no bladder volume could be released and the increased tension on the bladder wall would further enhance the bladder-to-bladder spinal reflex, which would result in a large amplitude, long-lasting, rebound bladder contraction. However, if the urethra was open as in this study, the bladder contraction induced by the removal of inhibitory pudendal nerve stimulation would cause a release of bladder content. This would reduce tension in the bladder wall, and in turn reduce mechano-sensitive afferent firing and excitatory input to the bladder-to-bladder spinal reflex pathway. Therefore, only small, short-lasting bladder contractions and release of saline from the bladder occurred (see FIG. 29B). The different results due to open or closed urethral conditions indicates that the spinal micturition reflex emerging after SCI is very different from the spinobulbospinal micturition reflex that is under the control of the PMC. Prolonged activation of the spinal micturition reflex that would be necessary for complete bladder emptying seems to require a persistent afferent excitatory input driven by a maintained bladder wall tension. On the other hand, the spinobulbospinal micturition reflex, once it is activated, can be kept active by the PMC even when the bladder is emptying and its volume becomes progressively smaller.

Intermittent 20-Hz stimulation induced post-stimulus voiding and increased voiding efficiency dramatically (FIG. 33A). During the intermittent pudendal nerve stimulation the bladder pressure induced by each burst of stimulation gradually decreased with time (FIGS. 31 and 32) indicating that the effect of pudendal nerve stimulation was gradually attenuated by the progressive decrease of bladder volume. The post-stimulus voiding is attributable to the persistence of the bladder contractions after termination of the stimulation in contrast to the rapid relaxation of the urethral sphincter striated muscles. However, as the bladder pressure induced by each stimulus burst progressively decreased (see FIGS. 31 and 32), it eventually failed to overcome the urethral outlet resistance resulting in a residual volume. The residual volumes were almost same (FIG. 33B) even when the initial bladder volumes were different (see FIG. 30A) indicating that the ability of pudendal nerve stimulation to empty the bladder was determined by urethral outlet resistance rather than the initial tension in the bladder wall. This also explains why 3-Hz stimulation increased bladder capacity, but did not reduce the absolute residual volume (see FIG. 30D and FIG. 33B).

The peak bladder pressures induced by intermittent 20-Hz stimulation were not significantly higher than those induced by the bladder distension (FIG. 34A). However, the average flow rate induced by the intermittent 20-Hz stimulation was significantly greater than that induced by bladder distension (see FIG. 34B). This indicated that the urethral outlet resistance was significantly lower during the post-stimulus voidings than during the voidings induced by bladder distension alone. One of the possible explanations is that the 20-Hz pudendal nerve stimulation inhibited the bladder-to-sphincter spinal reflex while it was activating the pudendal-to-bladder spinal reflex.

Here, the intermittent pudendal nerve stimulation was timed by manually switching on/off the stimulator while visually monitoring the induced bladder pressure. The duration of and the interval between the short burst stimulations could influence voiding efficiency (see FIGS. 31 and 32). Meanwhile, the stimulation intensity could also influence the result, because higher intensities could induce stronger contractions of the external urethral sphincter resulting in higher urethral resistance. However, a higher stimulation intensity might also cause the bladder pressure to rise faster and require a shorter burst duration to reach the bladder pressure effective for voiding. The influence of stimulation parameters (stimulation duration, interval, and intensity) on voiding efficiency may be studied in the future. The effectiveness of 3-Hz (inhibitory) or 20-Hz (excitatory) chronic pudendal nerve stimulation may be tested in humans to evaluate the potential clinical benefits of this therapy. In people with SCI electrical stimulation of dorsal penis/clitoris nerve using surface electrodes at frequencies ranging from 5 to 10 Hz can inhibit the hyperreflexic bladder activity (Vodusek D B, Light J K, Libby J M. Detrusor inhibition induced by stimulation of pudendal nerve afferents. Neurourol Urodyn 1986; 5:381-9 and Wheeler J S, Walter J S, Zaszczurynski P J. Bladder inhibition by penile nerve stimulation in spinal cord injury patients. J Urol 1992; 147:100-3). Since these nerves are branches of the pudendal nerve, the results with surface stimulation indicate that pudendal nerve stimulation at a frequency between 5 and 10 Hz might have to be employed in humans instead of 3 Hz. In complete SCI subjects, intra-urethral electrical stimulation at a frequency of 20 Hz excited the bladder (Gustafson K J, Creasey G H, Grill W M. A catheter based method to activate urethral sensory nerve fibers. J Urol 2003; 170:126-9 and Gustafson K J, Creasey G H, Grill W M. A urethral afferent mediated excitatory bladder reflex exists in humans. Neurosci Lett 2004; 360:9-12). Since the urethra is innervated by pudendal nerve, the 20-Hz pudendal nerve stimulation might be also effective in humans to activate bladder reflexes.

This study using chronic SCI cats has shown that a neural prosthetic device based on pudendal nerve stimulation might be developed to restore micturition function after SCI. This neural prosthetic device will not require a sacral posterior root rhizotomy which is needed in Brindley's method (Brindley G S, Rushton D N. Long-term follow-up of patients with sacral anterior root stimulator implants. Paraplegia 1990; 28:469-75; Creasey G H. Electrical stimulation of sacral roots for micturition after spinal cord injury. Spinal Cord Injury 1993; 20:505-15; and van Kerrebroeck P E V, Koldewijn E L, Rosier P F W M, et al. Results of the treatment of neurogenic bladder dysfunction in spinal cord injury by sacral posterior root rhizotomy and anterior sacral root stimulation. J Urol 1996; 155:1378-81). Therefore, it will preserve the remaining spinal reflexes for defecation and sexual functions after SCI. The surgery needed to access the pudendal nerve is also less invasive than Brindley's method that requires a spinal laminectory to access the sacral anterior and posterior roots. Although considerable study is still needed to fully implement the design of a pudendal nerve-stimulating device, further analysis of the pudendal-to-bladder spinal reflexes could provide substantial benefits for people with lower urinary tract dysfunctions after SCI.

Having described this invention above, it will be understood to those of ordinary skill in the art that the same can be performed within a wide and equivalent range of conditions, formulations and other parameters without affecting the scope of the invention or any embodiment thereof.

We claim:

1. A method of controlling one or both of micturition and defecation in a subject, comprising:
inducing one or both of micturition and defecation in the subject by applying an electrical signal to a pudendal nerve or a branch thereof of a subject at a first point on the pudendal nerve or branch thereof, the electrical signal having an amplitude and frequency able to create a reflex that results in one or both of bladder contractions and rectal contractions; and applying a blocking electrical signal distal to the first point on the pudendal nerve of the subject or a branch thereof and on a contralateral pudendal nerve or branch thereof, the blocking electrical signal having an amplitude and frequency able to block pudendal nerve conduction for inhibiting contraction of one or both of the external urethral sphincter and the anal sphincter of the subject.

2. The method of claim 1, further comprising prior to producing one or both of micturition and defecation in the subject, applying an electrical signal to a pudendal nerve or a branch thereof of the subject, the electrical signal having an amplitude and frequency able to create a reflex that inhibits one or both of bladder contractions and rectal contractions in the subject.

3. The method of claim 1, wherein the frequency of the electric signal having an amplitude and frequency able to create a reflex that inhibits one or both of bladder contractions and rectal contractions in the subject ranges from 0.5 Hz to 15 Hz.

4. The method of claim 1, in which the electrical signals are biphasic.

5. The method of claim 4, in which the electrical signals are biphasic and charge-balanced.

6. The method of claim 1, in which the frequency of the electric signal having an amplitude and frequency able to create a reflex that results in one or both of bladder contractions and rectal contractions in the subject ranges from 15 Hz to 50 Hz.

7. The method of claim 1, in which the frequency of the blocking electric signal having an amplitude and frequency able to block the pudendal nerve conduction for inhibiting contraction of one or both of the external urethral sphincter and the anal sphincter of the subject is greater than 4 kHz.

8. The method of claim 7, in which the electric signals are biphasic.

9. The method of claim 8, in which the electrical signals are biphasic and charge-balanced.

10. The method of claim 1, wherein an implanted microprocessor-controlled pulse generator is used to apply the electric signal to the pudendal nerve of the subject or a branch thereof.

11. The method of claim 10, wherein the pulse generator comprises at least three output channels that are independently adjustable with respect to one or more of output pulse voltage, amperage and frequency.

12. The method of claim 11, wherein the pulse generator comprises an antenna and one or more of the output pulse voltage, amperage and frequency of the electric signal produced by the output channels are controllable by an external transmitter that transmits a signal that is received by the antenna of the pulse generator and data can be transmitted from the pulse generator to an external receiver.

13. The method of claim 12, wherein the external receiver is contained in a device comprising the transmitter.

14. The method of claim 12, in which the external transmitter transmits an identification signal to the pulse generator, the pulse generator requiring an appropriate identification signal from the transmitter to control one or more of the output pulse voltage, amperage, wave shape and frequency of the electric signal produced by the output channels.

15. The method of claim 12, in which one of the pulse generator and the transmitter comprises an RFID tag and the other of the pulse generator and the transmitter comprises an RFID reader and verification of the identity of the pulse generator and transmitter by RFID is required to control one or more of the output pulse voltage, amperage, wave shape and frequency of the electric signal produced by the output channels.

16. The method of claim 12, in which signals from the transmitter are encrypted and can only be decrypted by a matching pulse generator.

17. The method of claim 12, wherein one of the pulse generator and the transmitter require identification of the other before the transmitter can control one or more of the output pulse voltage, amperage, wave shape and frequency of the electric signal produced by the output channels.

18. A method of controlling one or both of micturition and defecation in a subject, comprising:
inducing one or both of micturition and defecation in the subject by applying an electrical signal to a pudendal nerve or a branch thereof of a subject at a first point on the pudendal nerve or branch thereof, the electrical signal having an amplitude and frequency able to create a reflex that results in one or both of bladder contractions and rectal contractions; and applying a blocking electrical signal ipsilaterally to the pudendal nerve of the subject or a branch thereof distal to the first point, or ipsilaterally distal to the first point and on a contralateral pudendal nerve or branch thereof, the blocking electrical signal having an amplitude and frequency able to block pudendal nerve conduction for inhibiting contraction of one or both of the external urethral sphincter and the anal sphincter of the subject, wherein the frequency of the blocking electrical signal is about 4 kHz or higher.

* * * * *

UNITED STATES PATENT AND TRADEMARK OFFICE
CERTIFICATE OF CORRECTION

| | | |
|---|---|---|
| PATENT NO. | : 8,805,510 B2 | Page 1 of 1 |
| APPLICATION NO. | : 12/184518 | |
| DATED | : August 12, 2014 | |
| INVENTOR(S) | : Michael B. Chancellor et al. | |

It is certified that error appears in the above-identified patent and that said Letters Patent is hereby corrected as shown below:

In the Claims,

Column 53, Line 47, Claim 3, delete "claim 1," and insert -- claim 2, --

Column 53, Line 53, Claim 4, delete "claim 1," and insert -- claim 2, --

Column 54, Line 3, Claim 8, delete "claim 7," and insert -- claim 1, --

Signed and Sealed this
Seventh Day of April, 2015

Michelle K. Lee
*Director of the United States Patent and Trademark Office*